(12) United States Patent
Angermann et al.

(10) Patent No.: US 8,367,873 B2
(45) Date of Patent: Feb. 5, 2013

(54) PHENYL-SUBSTITUTED BICYCLOOCTANE-1,3-DIONE DERIVATIVES

(75) Inventors: Alfred Angermann, Kriftel (DE); Guido Bojack, Wiesbaden-Naurod (DE); Reiner Fischer, Monheim (DE); Stefan Lehr, Liederbach (DE); Jan Dittgen, Frankfurt (DE); Dieter Feucht, Eschborn (DE); Isolde Häuser-Hahn, Leverkusen (DE); Christopher Hugh Rosinger, Hofheim (DE); Arnd Voerste, Köln (DE)

(73) Assignee: Bayer Cropscience AG, Monheim (DE)

( * ) Notice: Subject to any disclaimer, the term of this patent is extended or adjusted under 35 U.S.C. 154(b) by 286 days.

(21) Appl. No.: 12/750,336

(22) Filed: Mar. 30, 2010

(65) Prior Publication Data

US 2011/0039701 A1 Feb. 17, 2011

Related U.S. Application Data

(63) Continuation-in-part of application No. 12/576,371, filed on Oct. 9, 2009, now abandoned.

(30) Foreign Application Priority Data

Oct. 10, 2008 (EP) .................................... 08166352

(51) Int. Cl.
*C07C 49/00* (2006.01)
*A01N 43/60* (2006.01)

(52) U.S. Cl. ....................................... 568/327; 504/136
(58) Field of Classification Search ................... None
See application file for complete search history.

(56) References Cited

U.S. PATENT DOCUMENTS

| | | | |
|---|---|---|---|
| 2,842,476 A | 7/1958 | Schreiber et al. |
| 4,091,006 A | 5/1978 | Durden, Jr. et al. |
| 4,283,348 A | 8/1981 | Wheeler |
| 4,338,122 A | 7/1982 | Wheeler |
| 4,436,666 A | 3/1984 | Wheeler |
| 4,526,723 A | 7/1985 | Wheeler et al. |
| 4,551,547 A | 11/1985 | Wheeler |
| 4,623,727 A | 11/1986 | Hübele |
| 4,632,698 A | 12/1986 | Wheeler |
| 4,639,266 A | 1/1987 | Heubach et al. |
| 4,844,734 A | 7/1989 | Iwasaki et al. |
| 4,881,966 A | 11/1989 | Nyffeler et al. |
| 4,888,049 A | 12/1989 | Iwasaki et al. |
| 4,891,057 A | 1/1990 | Sohn et al. |
| 4,902,340 A | 2/1990 | Hubele |
| 4,944,790 A | 7/1990 | Moser et al. |
| 5,013,659 A | 5/1991 | Bedbrook et al. |
| 5,215,570 A | 6/1993 | Burckhardt et al. |
| 5,314,863 A | 5/1994 | Löher et al. |
| 5,380,852 A | 1/1995 | Schütze et al. |
| 5,401,700 A | 3/1995 | Sohn et al. |
| 5,462,912 A | 10/1995 | Hioki et al. |
| 5,500,367 A | 3/1996 | Hain et al. |
| 5,516,750 A | 5/1996 | Willms et al. |
| 5,538,937 A | 7/1996 | Hasebe et al. |
| 5,689,046 A | 11/1997 | Schröder et al. |
| 5,700,758 A | 12/1997 | Rösch et al. |
| 5,705,476 A | 1/1998 | Hoffarth |
| 5,739,079 A | 4/1998 | Holdgrün et al. |
| 5,792,755 A | 8/1998 | Sagenmüller et al. |
| 5,808,135 A | 9/1998 | Fischer et al. |
| 5,840,661 A | 11/1998 | Fischer et al. |
| 5,972,839 A | 10/1999 | Ziemer et al. |
| 6,235,680 B1 | 5/2001 | Ziemer et al. |
| 6,251,827 B1 | 6/2001 | Ziemer et al. |
| 6,251,833 B1 | 6/2001 | Erdelen et al. |

(Continued)

FOREIGN PATENT DOCUMENTS

| | | |
|---|---|---|
| AU | 3495189 A | 11/1987 |
| CA | 1 162 071 A1 | 2/1984 |

(Continued)

OTHER PUBLICATIONS

Bandgar, B.P. and Bettigeri, S.V., "Efficient and Selective Halogenation of Allylic and Benzylic Alcohols under Mild Conditions," *Monatshefte Fur Chemie*, 135:1251-1255, Springer-Verlag GmbH, Germany (2004).

(Continued)

*Primary Examiner* — Johann Richter
*Assistant Examiner* — Jennifer C Sawyer
(74) *Attorney, Agent, or Firm* — Sterne, Kessler, Goldstein & Fox P.L.L.C.

(57) ABSTRACT

The invention relates to novel compounds of the formula (I)

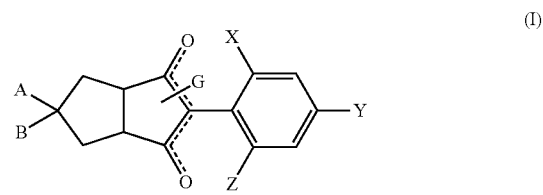

in which X, Y, Z, A, B and G have the meanings given above, to a plurality of processes and intermediates for their preparation and to their use as pesticides and/or herbicides.

Moreover, the invention relates to selective herbicidal compositions comprising, firstly, the phenyl-substituted bicyclooctane-1,3-dione derivates 33 and, secondly, a crop plant compatibility-improving compound.

The present invention furthermore relates to increasing the activity of crop protection compositions comprising in particular phenyl-substituted bicyclooctane-1,3-dione derivates by adding ammonium salts or phosphonium salts and, if appropriate, penetrants, to the corresponding compositions, to processes for their preparation and to their use in crop protection as insecticides and/or acaricides and/or for preventing unwanted plant growth.

18 Claims, No Drawings

U.S. PATENT DOCUMENTS

| | | |
|---|---|---|
| 6,417,370 B1 | 7/2002 | Lieb et al. |
| 6,451,843 B1 | 9/2002 | Lieb et al. |
| 6,458,965 B1 | 10/2002 | Lieb et al. |
| 6,515,184 B1 | 2/2003 | Fischer et al. |
| 6,602,823 B1 | 8/2003 | Röchling et al. |
| 6,645,914 B1 | 11/2003 | Woznica et al. |
| 6,894,005 B1 | 5/2005 | Maetzke et al. |
| 2003/0216260 A1 | 11/2003 | Ruther et al. |
| 2003/0224939 A1 | 12/2003 | Miles |
| 2004/0224844 A1 | 11/2004 | Bickers et al. |
| 2005/0009880 A1 | 1/2005 | Cottrell et al. |
| 2005/0037922 A1 | 2/2005 | Bickers et al. |
| 2005/0049145 A1 | 3/2005 | Bickers et al. |
| 2005/0090399 A1 | 4/2005 | Friedmann et al. |
| 2005/0096386 A1 | 5/2005 | Cottrell et al. |
| 2005/0256000 A1 | 11/2005 | Schaper et al. |
| 2006/0166829 A1 | 7/2006 | Fischer et al. |
| 2007/0015664 A1 | 1/2007 | Fischer et al. |
| 2007/0298968 A1 | 12/2007 | Bretschneider et al. |
| 2009/0127393 A1 | 5/2009 | Fischer et al. |
| 2009/0209513 A1 | 8/2009 | Fischer et al. |
| 2009/0227563 A1 | 9/2009 | Fischer et al. |
| 2010/0009850 A1 | 1/2010 | Fischer et al. |

FOREIGN PATENT DOCUMENTS

| | | |
|---|---|---|
| CA | 2 077 896 A1 | 9/1991 |
| CA | 2 668 138 A1 | 10/2007 |
| EP | 0 142 924 A2 | 5/1985 |
| EP | 0 193 259 A1 | 9/1986 |
| EP | 0 221 044 A1 | 5/1987 |
| EP | 0 242 236 A1 | 10/1987 |
| EP | 0 242 246 A1 | 10/1987 |
| EP | 0 257 993 A2 | 3/1988 |
| EP | 0 453 086 A2 | 10/1991 |
| JP | 60 087 254 A2 | 5/1985 |
| WO | WO 92/16108 A1 | 10/1902 |
| WO | WO 8402919 A1 | 8/1984 |
| WO | WO 91/19806 A1 | 12/1991 |
| WO | WO 92/00377 A1 | 1/1992 |
| WO | WO 92/11376 A1 | 7/1992 |
| WO | WO 92/14827 A1 | 9/1992 |
| WO | WO 95/17817 A1 | 7/1995 |
| WO | WO 98/13361 A1 | 4/1998 |
| WO | WO 98/35553 A1 | 8/1998 |
| WO | WO 98/38856 A1 | 9/1998 |
| WO | WO 02/34048 A1 | 5/2002 |
| WO | WO 2007/023719 A1 | 3/2007 |
| WO | WO 2007/023764 A1 | 3/2007 |
| WO | WO 2009/019005 A2 | 2/2009 |
| WO | WO 2009/019015 A1 | 2/2009 |
| ZA | 9805601 A | 1/1999 |

OTHER PUBLICATIONS

Baur, P., et al., "Polydisperse Ethoxylated Fatty Alcohol Surfactants as Accelerators of Cuticular Penetration. 1. Effects of Ethoxy Chain Length and the Size of the Penetrants," *Pesticide Science*, 51:131-152, SCI, United Kingdom (1997).

Braun, H.-P., et al., "The General Mitochondrial Processing Peptidase from Potato is an Integral Part of Cytochrome C Reductase of the Respiratory Chain," *The EMBO Journal*, 11:3219-3227, Oxford University Press, United Kingdom (1992).

Chambers, M.S., et al., "An Asymmetric Synthesis of Thiotetronic Acids using Chirality Transfer *via* an Allyl Xanthate-to-Dithiocarbonate Rearrangement. X-Ray Crystal Structure of (5*R*)-2,5-Dihydro-4-Hydroxy-5-methyl-3-phenyl-5-prop-1' -enyl-2-oxothiophene," *Journal of the Chemical Society, Chemical Communications*, 16:1228-1230, Royal Society of Chemistry, United Kingdom (1987).

Edwards, R.L., et al., "Constituents of the Higher Fungi. Part IV. Involutin, a Diphenyl-cyclopenteneone from *Paxillus involutus* (Oeder ex Fries)," *Journal of the Chemical Society, Organic Articles*, 6:405-409, Royal Society of Chemistry, United Kingdom (1967).

Fuchs, B., et al., "Struktur und Magnetische Anisotropie Mesitylsubstituierter Ferrocene," *Chemische Berichte*, 118:1968-1982, Wiley-VCH Verlags GmbH, Weinheim (1985).

Hevesy, G., "Life Span of Tissue Cells," *Acta Chemica Scandinavica*, 17. 1):S17-S22, Chemical Societies of Denmark, Finland, Norway and Sweden, Sweden (1963).

Knochel, P. and Singer, R.D., "Preparation and Reactions of Polyfunctional Organozinc Reagents in Organic Synthesis," *Chemical Reviews*, 93:2117-2188, American Chemical Society, United States (1993).

Majid, T.N., et al., "Synthesis and Reactivity of Open-Chain and Cyclic 2-Cyano Zinc and Copper Organometallics," *Tetrahedron Letters*, 30:5069-5072, Pergamon Press plc, United Kingdom (1989).

Metzger, A., et al., "Polyfunctional Benzylic Zinc Chlorides by the Direct Insertion of Magnesium into Benzylic Chlorides in the Presence of LiCl and $ZnCl_2$," *Journal of the Chemical Society, Chemical Communications*, 40:5824-5826, Royal Society of Chemistry, United Kingdom (2008).

Micklefield, J., et al., "Alkylation and Acylation of 5-Phenylsulphonyl and 5-Cyanobutyrolactones," *Tetrahedron*, 48:7519-7526, Pegamon Press Ltd, United Kingdom (1992).

Sonnewald, U., et al., "Transgenic Tobacco Plants Expressing Yeast-derived Invertase in either the Cytosol, Vacuole or Apoplast: a Powerful Tool for Studying Sucrose Metabolism and Sink/Source Interactions," *The Plant Journal*, 1:96-106, Wiley-Blackwell in association with the Society for Experimental Biology, United Kingdom (1991).

Sousa, A.A., et al., "Esters of 3-Hydroxy-2-Arylindones, a New Class of Acaricide," *Journal of Economic Entomology*, 66:584-586, Entomological Society of America, United States (1973).

Wolter, F.P., et al., "*rbcS* Genes in *Solanum tuberosum*: Conservation of Transit Peptide and Exon Shuffling during Evolution," *Proc. Natl. Acad. Sci.*, 5:846-850, National Academy of Sciences of the United States of America, United States (1988).

English language Abstract of PCT Publication No. WO 07/023719 A1 (2007).

English language Abstract of PCT Publication No. WO 07/023764 A1 (2007).

English language Abstract of Japanese Patent Publication No. JP 60-087254 A (1985).

International Search Report for Application No. EP 08 166 352, European Patent Office, Munich, mailed on Sep. 3, 2009.

PHENYL-SUBSTITUTED BICYCLOOCTANE-1,3-DIONE DERIVATIVES

The present invention relates to novel phenyl-substituted bicyclooctane-1,3-dione derivatives, to a plurality of processes for their preparation and to their use as pesticides and/or herbicides.

Moreover, the invention relates to novel selective herbicidal active compound combinations comprising, firstly, phenyl-substituted bicyclooctane-1,3-dione derivates and, secondly, at least one crop plant compatibility-improving compound, which combinations can be used with particularly good results for the selective control of weeds and various crops of useful plants.

The present invention furthermore relates to increasing the activity of crop protection compositions comprising in particular phenyl-substituted bicyclooctane-1,3-dione derivates by adding ammonium salts or phosphonium salts and, if appropriate, penetrants, to the corresponding compositions, to processes for their preparation and to their use in crop protection as insecticides and/or for preventing unwanted plant growth.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO99/48869, WO 99/55673, WO 01/17972, WO 01/74770, WO 03/062244, WO 04/080962, WO04/111042, WO05/092897, WO06/029799, WO07/080,066, WO07/096,058, WO 09/019,005 and WO 09/019,015). Also known are compounds which are substituted in a similar way: 3-hydroxy-5,5-dimethyl-2-phenylcyclopent-2-en-1-one from the publication Micklefield et. al., Tetrahedron, (1992), 7519-26 and the natural product Involution (−)-cis-5-(3,4-dihydroxyphenyl)-3,4-dihydroxy-2-(4-hydroxyphenyl)-cyclopent-2-enone from the publication Edwards et al., J. Chem. Soc. S, (1967), 405-9. An insecticidal or acaricidal action is not described. Moreover, 2-(2,4,6-trimethylphenyl)-1,3-indanedione is known from the publication J. Economic Entomology, 66 (1973), 584 and the laid-open publication DE-A 2 361 084, with herbicidal and acaricidal actions being stated.

However, in particular at low application rates and concentrations, the activity and activity spectrum of these compounds is not always fully satisfactory. Furthermore, the compatibility of these compounds with plants is not always sufficient.

This invention now provides novel compounds of the formula (I)

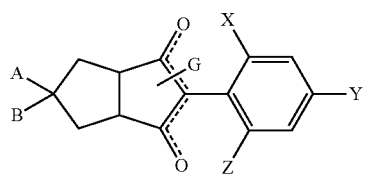

in which
X represents alkyl, cycloalkyl or alkoxy,
Y represents hydrogen, alkyl or alkoxy,
Z represents hydrogen, alkyl or cycloalkyl, where
A and B together with the carbon atom to which they are attached represent a saturated or unsaturated unsubstituted or substituted cycle which optionally contains at least one heteroatom,
or
A and B together with the carbon atom to which they are attached represent a carbonyl group, a $C_1$-$C_4$-alkylene group or a =N—$OR^9$ group,
G represents hydrogen (a) or represents one of the groups

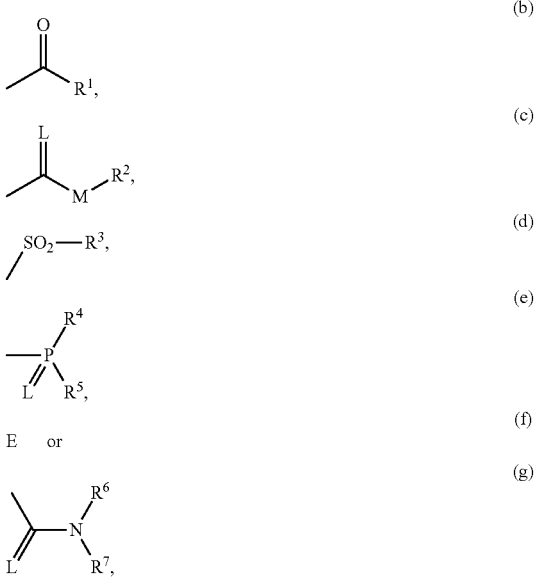

in which
E represents a metal ion equivalent or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio,
$R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur,
$R^9$ represents hydrogen, represents in each case optionally substituted alkyl, cycloalkyl, $CH_2$-cycloalkyl, alkenyl, alkinyl, arylalkyl or hetarylalkyl.

Depending inter alia on the nature of the substituents, the compounds of the formula (I) may be present as geometric and/or optical isomers or isomer mixtures of varying composition which, if appropriate, may be separated in a customary manner. The present invention provides both the pure isomers and the isomer mixtures, their preparation and use and compositions comprising them. However, for the sake of simplicity, hereinbelow only compounds of the formula (I) are referred to, although what is meant is both the pure compounds and, if appropriate, mixtures having various proportions of isomeric compounds.

Depending on the position of the substituent G, the compounds of the formula (I) can be present in the two isomeric forms of the formulae (I-A) and (I-B)

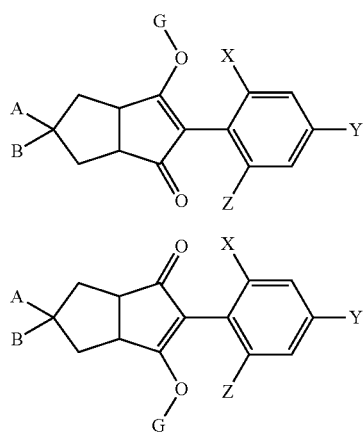

(I-A)

(I-B)

which is meant to be indicated by the broken line in formula (I).

The compounds of the formulae (I-A) and (I-B) can be present both as mixtures and in the form of their pure isomers. If appropriate, mixtures of the compounds of the formulae (I-A) and (I-B) can be separated by physical methods, for example by way of chromatographic methods.

For reasons of clarity, hereinbelow only one of the possible isomers is shown in each case. This does not exclude that, if appropriate, the compounds may be present in the form of the isomer mixtures or in the respective other isomeric form.

Including the different meanings (a), (b), (c), (d), (e), (f) and (g) of group G, the following principle structures (I-a) to (I-g) result:

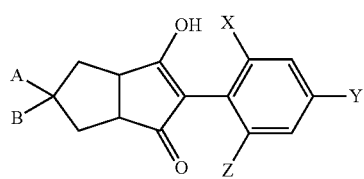

(I-a)

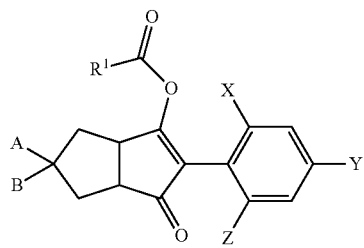

(I-b)

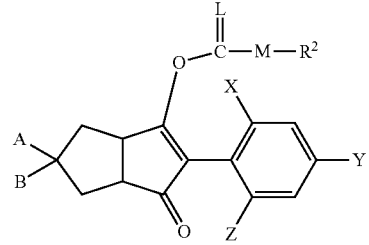

(I-c)

(I-d):

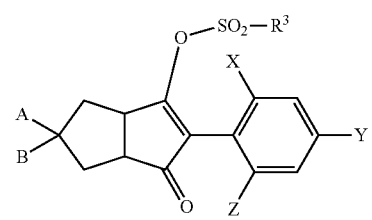

(I-d)

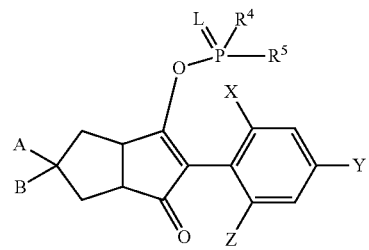

(I-e)

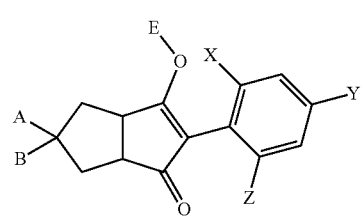

(I-f)

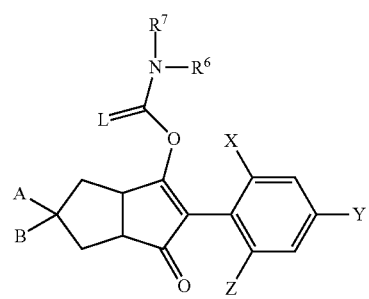

(I-g)

in which

A, B, E, L, M, X, Y, Z, $R^1$, $R^2$, $R^3$, $R^4$, $R^5$, $R^6$ and $R^7$ have the meanings given above.

A further form of stereoisomerism results from the cis-attachment of the two carbacyclic five-membered rings, namely in the case where specifically the two substituents A and B in formula (Ia) are not identical.

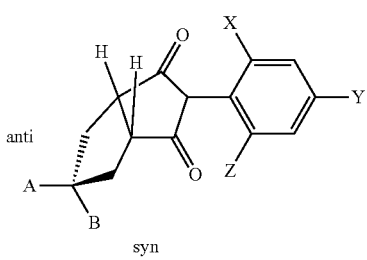

Hereinbelow, the isomers encountered in this case are referred to as "syn" and "anti", respectively, depending on whether the substituent A or B to be prioritized according to the Cahn-Ingold-Prelog rules is in the anti- or syn-position to the cyclopentanedione ring. Two examples of such forms of isomerism in the compounds of the formula (I-a) are mentioned below:

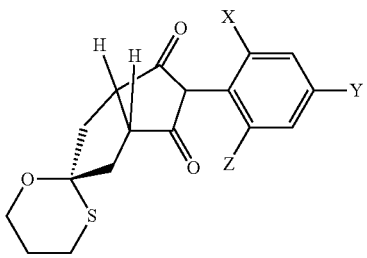

syn-isomer

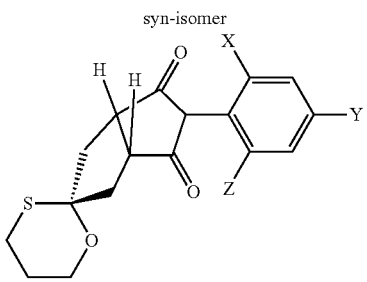

anti-isomer

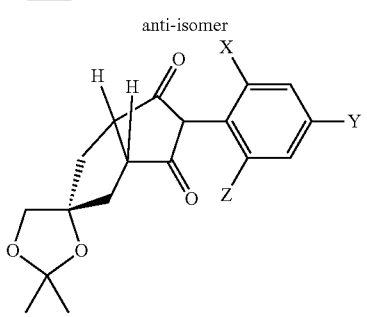

syn-isomer

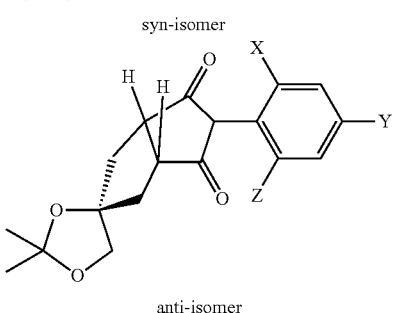

anti-isomer

Furthermore, it has been found that the novel compounds of the formula (I) are obtained by one of the processes described below:

(A) Compounds of the formula (I-a)

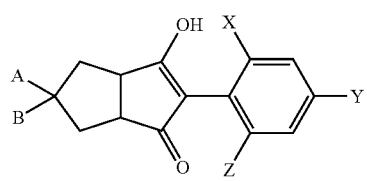

in which
A, B, X, Y and Z have the meaning given above
are obtained when
ketocarboxylic esters of the formula (II)

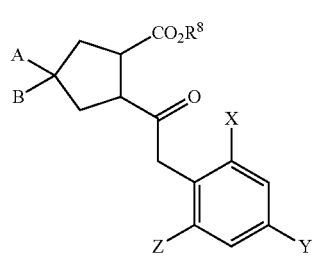

in which
A, B, X, Y and Z have the meaning given above and
$R^8$ represents alkyl (in particular $C_1$-$C_8$-alkyl)
are cyclized intramolecularly, if appropriate in the presence of a diluent and in the presence of a base.

Moreover, it has been found (B) that the compounds of the formula (I-b) shown above in which A, B, $R^1$, X, Y and Z have the meanings given above are obtained when compounds of the formula (I-a) shown above in which A, B, X, Y and Z have the meanings given above are in each case reacted (α) with acid halides of the formula (III)

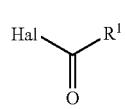

in which
$R^1$ has the meaning given above and
Hal represents halogen (in particular chlorine or bromine)
or (β) with carboxylic anhydrides of the formula (IV)

$R^1$—CO—O—CO—$R^1$ (IV)

in which
$R^1$ has the meaning given above,
if appropriate in the presence of a diluent and if appropriate in the presence of an acid binder;

(C) that the compounds of the formula (I-c) shown above in which A, B, $R^2$, M, X, Y and Z have the meanings given above and L represents oxygen are obtained when the compounds of the formula (I-a) shown above in which A, B, X, Y and Z have the meanings given above are in each case reacted
with chloroformic esters or chloroformic thio esters of the formula (V)

  (V)

in which
R² and M have the meanings given above,
if appropriate in the presence of a diluent and if appropriate in the presence of an acid binder;

(D) that compounds of the formula (I-c) shown above in which A, B, R², M, X, Y and Z have the meanings given above and L represents sulphur are obtained when compounds of the formula (I-a) shown above in which A, B, X, Y and Z have the meanings given above are in each case reacted
with chloromonothioformic esters or chlordithioformic esters of the formula (VI)

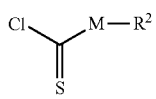  (VI)

in which
M and R² have the meanings given above,
if appropriate in the presence of a diluent and if appropriate in the presence of an acid binder;

(E) that compounds of the formula (I-d) shown above in which A, B, R³, X, Y and Z have the meanings given above are obtained when compounds of the formula (I-a) shown above in which A, B, X, Y and Z have the meanings given above are in each case reacted
with sulphonyl chlorides of the formula (VII)

  (VII)

in which
R³ has the meaning given above,
if appropriate in the presence of a diluent and if appropriate in the presence of an acid binder, (F) that compounds of the formula (I-e) shown above in which A, B, L, R⁴, R⁵, X, Y and Z have the meanings given above are obtained when compounds of the formula (I-a) shown above in which A, B, X, Y and Z have the meanings given above are in each case reacted
with phosphorus compounds of the formula (VIII)

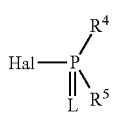  (VIII)

in which
L, R⁴ and R⁵ have the meanings given above and
Hal represents halogen (in particular chlorine or bromine),
if appropriate in the presence of a diluent and if appropriate in the presence of an acid binder, (G) that compounds of the formula (I-f) shown above in which A, B, E, X, Y and Z have the meanings given above are obtained when compounds of the formula (I-a) in which A, B, X, Y and Z have the meanings given above are in each case reacted
with metal compounds or amines of the formulae (IX) or (X), respectively

  (IX)

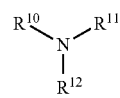  (X)

in which
Me represents a mono- or divalent metal (preferably an alkali metal or alkaline earth metal, such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl),
if appropriate in the presence of a diluent, (H) that compounds of the formula (I-g) shown above in which A, B, L, R⁶, R⁷, X, Y and Z have the meanings given above are obtained
when compounds of the formula (I-a) shown above in which A, B, X, Y and Z have the meanings given above are in each case reacted
(α) with isocyanates or isothiocyanates of the formula (XI)

  (XI)

in which
R⁶ and L have the meanings given above,
if appropriate in the presence of a diluent and if appropriate in the presence of a catalyst, or
(β) with carbamoyl chlorides or thiocarbamoyl chlorides of the formula (XII)

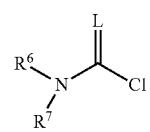  (XII)

in which
L, R⁶ and R⁷ have the meanings given above,
if appropriate in the presence of a diluent and if appropriate in the presence of an acid binder.

Furthermore, it has been found that the novel compounds of the formula (I) are very effective as pesticides, preferably as insecticides, acaricides and herbicides.

Surprisingly, it has now also been found that certain substituted cyclic ketoenoles, when used together with the crop plant compatibility-improving compounds (safener/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, potatoes, soya beans and rice.

The invention also provides selective herbicidal compositions comprising an effective amount of an active compound combination comprising, as components,
a') at least one compound of the formula (I), in which A, B, G, X, Y and Z have the meaning given above and
(b') at least one crop plant compatibility-improving compound (safener).

The safeners are preferably selected from the group consisting of:

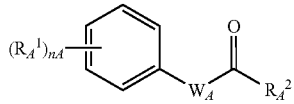
(S1)

S1) Compounds of the formula (S1)
where the symbols and indices have the following meanings:
$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group consisting of partially unsaturated or aromatic five-membered heterocycles having 1 to 3 hetero ring atoms from the group consisting of N and O, where at least one nitrogen atom and at most one oxygen atom is present in the ring, preferably a radical from the group consisting of $(W_A^1)$ to $(W_A^4)$,

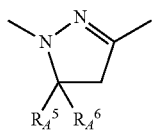
($W_A^1$)

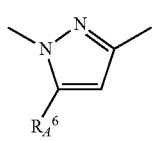
($W_A^2$)

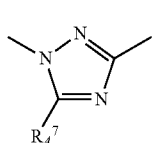
($W_A^3$)

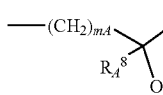
($W_A^4$)

$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S1) and which is unsubstituted or substituted by radicals from the group consisting of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;
$R_A^3$ is hydrogen or an unsubstituted or substituted aliphatic hydrocarbon radical having preferably a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;
$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;
preferably:
a) compounds of the type of the dichlorophenylpyrazoline-3-carboxylic acid (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;
b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;
c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;
d) compounds of the type of the triazolecarboxylic acids (S1$^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;
e) compounds of the type of the 5-benzyl- or 5-phenyl-2-isoxazoline-3-carboxylic acid or the 5,5-diphenyl-2-isoxazoline-3-carboxylic acid (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in the patent application WO-A-95/07897.

S2) Quinoline derivatives of the formula (S2)

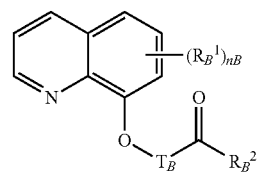
(S2)

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of $(C_1-C_4)$-alkyl, $(C_1-C_4)$-alkoxy and optionally substituted phenyl, preferably a radical of the formula $OR_B^3$, $NHR_B^4$ or $N(CH_3)_2$, in particular of the formula $OR_B^3$;

$R_B^3$ is hydrogen or an unsubstituted or substituted aliphatic hydrocarbon radical having preferably a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$- or $C_2)$-alkanediyl chain which is unsubstituted or substituted by one or two $(C_1-C_4)$-alkyl radicals or by $[(C_1-C_3)$-alkoxy]carbonyl;

preferably:
a) compounds of the type of the 8-quinolinoxyacetic acid $(S2^a)$, preferably 1-methylhexyl (5-chloro-8-quinolinoxy)acetate ("cloquintocet-mexyl") (S2-1), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl (5-chloro-8-quinolinoxy) acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminium, iron, ammonium, quaternary ammonium, sulphonium or phosphonium salts, as described in WO-A-2002/34048;
b) compounds of the type of the (5-chloro-8-quinolinoxy) malonic acid $(S2^b)$, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

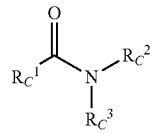

(S3)

where the symbols and indices have the following meanings:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:
active compounds of the type of the dichloroacetamides which are frequently used as pre-emergence safeners (soil-acting safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl] dichloroacetamide) from PPG Industries (S3-5), "DKA-24" (N-allyl-N-[(allylaminocarbonyl)methyl] dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8)

"diclonon" (dicyclonon) or "BAS145138" or "LAB145138" (S3-9) (3-dichloroacetyl-2,5,5-trimethyl-1,3-diazabicyclo[4.3.0]nonane) from BASF, "furilazole" or "MON 13900" ((RS)-3-dichloroacetyl-5-(2-furyl)-2,2-dimethyloxazolidine) (S3-10) and also its (R)-isomer (S3-11).

S4) N-Acylsulphonamides of the formula (S4) and their salts

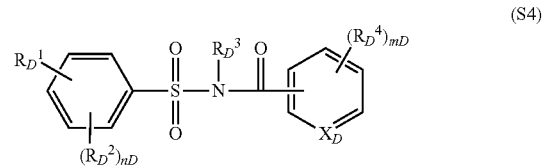

(S4)

where the symbols and indices have the following meanings:

$X_D$ is CH or N;

$R_D^1$ is CO—$NR_D^5R_D^6$ or NHCO—$R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;

$R_D^3$ is hydrogen, $(C_1-C_4)$-alkyl, $(C_1-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three last-mentioned radicals are substituted by $v_D$ radicals from the group consisting of halogen, hydroxy, $(C_1-C_4)$-alkyl, $(C_1-C_4)$-alkoxy and $(C_1-C_4)$-alkylthio, or $R_D^7$ and $R_D^6$ together with the nitrogen atom carrying them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;
$m_D$ is 1 or 2;
$v_D$ is 0, 1, 2 or 3;

from among these, preference is given to compounds of the type of the N-acylsulphonamides, for example of the formula (S4$^a$) below, which are known, for example, from WO-A-97/4subchamber16

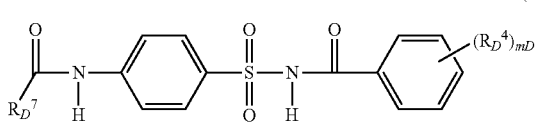

(S4a)

in which $R_D^7$ is $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$,
$m_D$ 1 or 2;
$v_D$ is 0, 1, 2 or 3;
and also acylsulphamoylbenzamides, for example of the formula (S4$^b$) below, which are known, for example, from WO-A-99/16744,

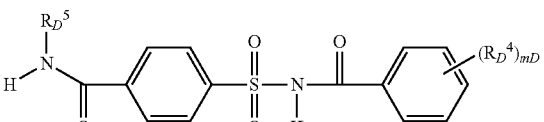

(S4b)

for example those in which $R_D^5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)

and also compounds of the type of the N-acylsulphamoylphenylureas of the formula (S4$^c$), which are known, for example, from EP-A-365484,

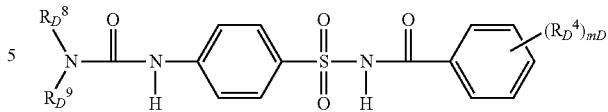

(S4c)

in which $R_D^8$ and $R_D^9$ independently of one another are hydrogen, $(C_1-C_8)$-alkyl, $(C_3-C_8)$-cycloalkyl, $(C_3-C_6)$-alkenyl, $(C_3-C_6)$-alkynyl, $R_D^4$ is halogen, $(C_1-C_4)$-alkyl, $(C_1-C_4)$-alkoxy, $CF_3$,
$m_D$ is 1 or 2;
for example 1-[4-(N-2-methoxybenzoylsulphamoyl)phenyl]-3-methylurea,
1-[4-(N-2-methoxybenzoylsulphamoyl)phenyl]-3,3-dimethylurea,
1-[4-(N-4,5-dimethylbenzoyl sulphamoyl)phenyl]-3-methylurea S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

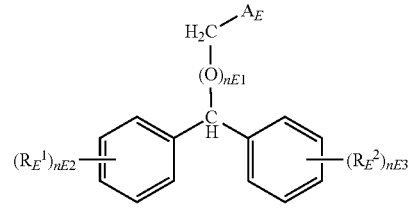

(S7)

where the symbols and indices have the following meanings:

$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ is $COOR_E^3$ or $COSR_E^4$ $R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ is 0 or 1;
$n_E^2$, $n_E^3$ independently of one another are 0, 1 or 2, preferably:
diphenylmethoxyacetic acid,
ethyl diphenylmethoxyacetate,
methyl diphenylmethoxyacetate (CAS Reg. No.: 41858-19-9) (S7-1).

S8) Compounds of the formula (S8), as described in WO-A-98/27049,

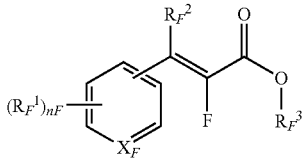
(S8)

in which
$X_F$ is CH or N,
$n_F$ is, if $X_F$=N, an integer from 0 to 4 and is, if $X_F$=CH, an integer from 0 to 5,
$R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_1-C_4)$-alkynyl or aryl, where each of the carbon-containing radicals mentioned above is unsubstituted or substituted by one or more, preferably by up to three, identical or different radicals from the group consisting of halogen and alkoxy; or salts thereof,
preferably compounds in which
$X_F$ is CH,
$n_F$ is an integer from 0 to 2,
$R_F^1$ is halogen, $(C_1-C_4)$-alkyl, $(C_1-C_4)$-haloalkyl, $(C_1-C_4)$-alkoxy, $(C_1-C_4)$-haloalkoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy;
or salts thereof, S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999/000020.

S10) Compounds of the formula (S10$^a$) or (S10$^b$)
as described in WO-A-2007/023719 and WO-A-2007/023764

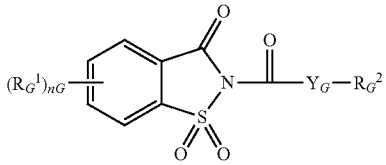
(S10a)

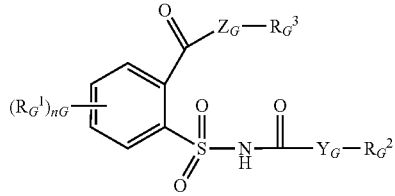
(S10b)

in which
$R_G^1$ is halogen, $(C_1-C_4)$-alkyl, methoxy, nitro, cyano, $CF_3$, $OCF_3$
$Y_G$, $Z_G$ independently of one another are O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.

S11) Active compounds of the type of the oxyimino compounds (S11), which are known as seed dressings, such as, for example, "oxabetrinil" ((Z)-1,3-dioxolan-2-ylmethoxyimino(phenyl)acetonitrile) (S11-1), which is known as seed dressing safener for millet against metolachlor damage,
"fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and
"cyometrinil" or "CGA-43089" ((Z)-cyanomethoxyimino(phenyl)acetonitrile) (S11-3), which is known as seed dressing safener for millet against metolachlor damage.

S12) Active compounds from the class of the isothiochromanones (S12), such as, for example, methyl [(3-oxo-1H-2-benzothiopyran-4(3H)-ylidene)methoxy]acetate (CAS Reg. No.: 205121-04-6) (S12-1) and related compounds from WO-A-1998/13361.

S13) One or more compounds from group (S13):
"naphthalic anhydride" (1,8-naphthalenedicarboxylic anhydride) (S13-1), which is known as seed dressing safener for corn against thiocarbamate herbicide damage,
"fenclorim" (4,6-dichloro-2-phenylpyrimidine) (S13-2), which is known as safener for pretilachlor in sown rice,
"flurazole" (benzyl 2-chloro-4-trifluoromethyl-1,3-thiazole-5-carboxylate) (S13-3), which is known as seed dressing safener for millet against alachlor and metolachlor damage,
"CL-304415" (CAS Reg. No.: 31541-57-8) (4-carboxy-3,4-dihydro-2H-1-benzopyran-4-acetic acid) (S13-4) from American Cyanamid, which is known as safener for corn against imidazolinone damage,
"MG-191" (CAS Reg. No.: 96420-72-3) (2-dichloromethyl-2-methyl-1,3-dioxolane) (S13-5) from Nitrokemia, which is known as safener for corn,
"MG-838" (CAS Reg. No.: 133993-74-5) (2-propenyl 1-oxa-4-azaspiro[4.5]decane-4-carbodithioate) (S13-6) from Nitrokemia,
"disulfoton" (O,O-diethyl S-2-ethylthioethyl phosphorodithioate) (S13-7),
"dietholate" (O,O-diethyl O-phenyl phosphorothioate) (S13-8),
"mephenate" (4-chlorophenyl methylcarbamate) (S13-9).

S14) Active compounds which, besides a herbicidal effect against harmful plants, also have a safener effect on crop plants such as rice, such as, for example; "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulphuron herbicide damage, "cumyluron"="JC-940" (3-(2-chlorophenylmethyl)-1-(1-methyl-1-phenyl-ethyl)urea, see JP-A-60087254), which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulphonyl)benzene) from Kumiai, (CAS Reg. No. 54091-06-4), which is known as safener against some herbicide damage in rice.

S15) Active compounds which are primarily used as herbicides, but also have safener effect on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Most preferred crop plant compatibility-improving compounds [component (b')] are cloquintocet-mexyl, fenchlorazole-ethyl, isoxadifen-ethyl, mefenpyr-diethyl, fenclorim, cumyluron, S4-1 and S4-5, and particular emphasis is given to cloquintocet-mexyl and mefenpyr-diethyl. Emphasis is also given to cyprosulphamide (S4-1).

Examples of the selective herbicidal combinations according to the invention comprising in each case one active compound of the formula (I) and in each case one of the safeners defined above are listed below:

| Active compound of the formula | Safener |
|---|---|
| I-a-1 | cloquintocet-mexyl |
| I-a-1 | fenchlorazole-ethyl |
| I-a-1 | isoxadifen-ethyl |
| I-a-1 | mefenpyr-diethyl |
| I-a-1 | fenclorim |
| I-a-1 | cumyluron |
| I-a-1 | S4-1 |
| I-a-1 | S4-5 |
| I-a-2 | cloquintocet-mexyl |
| I-a-2 | fenchlorazole-ethyl |
| I-a-2 | isoxadifen-ethyl |
| I-a-2 | mefenpyr-diethyl |
| I-a-2 | fenclorim |
| I-a-2 | cumyluron |
| I-a-2 | S4-1 |
| I-a-2 | S4-5 |
| I-a-3 | cloquintocet-mexyl |
| I-a-3 | fenchlorazole-ethyl |
| I-a-3 | isoxadifen-ethyl |
| I-a-3 | mefenpyr-diethyl |
| I-a-3 | fenclorim |
| I-a-3 | cumyluron |
| I-a-3 | S4-1 |
| I-a-3 | S4-5 |
| I-a-4 | cloquintocet-mexyl |
| I-a-4 | fenchlorazole-ethyl |
| I-a-4 | isoxadifen-ethyl |
| I-a-4 | mefenpyr-diethyl |
| I-a-4 | fenclorim |
| I-a-4 | cumyluron |
| I-a-4 | S4-1 |
| I-a-4 | S4-5 |
| I-a-5 | cloquintocet-mexyl |
| I-a-5 | fenchlorazole-ethyl |
| I-a-5 | isoxadifen-ethyl |
| I-a-5 | mefenpyr-diethyl |
| I-a-5 | fenclorim |
| I-a-5 | cumyluron |
| I-a-5 | S4-1 |
| I-a-5 | S4-5 |
| I-a-6 | cloquintocet-mexyl |
| I-a-6 | fenchlorazole-ethyl |
| I-a-6 | isoxadifen-ethyl |
| I-a-6 | mefenpyr-diethyl |
| I-a-6 | fenclorim |
| I-a-6 | cumyluron |
| I-a-6 | S4-1 |
| I-a-6 | S4-5 |
| I-a-7 | cloquintocet-mexyl |
| I-a-7 | fenchlorazole-ethyl |
| I-a-7 | isoxadifen-ethyl |
| I-a-7 | mefenpyr-diethyl |
| I-a-7 | fenclorim |
| I-a-7 | cumyluron |
| I-a-7 | S4-1 |
| I-a-7 | S4-5 |
| I-a-8 | cloquintocet-mexyl |
| I-a-8 | fenchlorazole-ethyl |
| I-a-8 | isoxadifen-ethyl |
| I-a-8 | mefenpyr-diethyl |
| I-a-8 | fenclorim |
| I-a-8 | cumyluron |
| I-a-8 | S4-1 |
| I-a-8 | S4-5 |
| I-a-9 | cloquintocet-mexyl |
| I-a-9 | fenchlorazole-ethyl |
| I-a-9 | isoxadifen-ethyl |
| I-a-9 | mefenpyr-diethyl |
| I-a-9 | fenclorim |
| I-a-9 | cumyluron |
| I-a-9 | S4-1 |
| I-a-9 | S4-5 |
| I-a-10 | cloquintocet-mexyl |
| I-a-10 | fenchlorazole-ethyl |
| I-a-10 | isoxadifen-ethyl |
| I-a-10 | mefenpyr-diethyl |
| I-a-10 | fenclorim |
| I-a-10 | cumyluron |
| I-a-10 | S4-1 |
| I-a-10 | S4-5 |
| I-a-11 | cloquintocet-mexyl |
| I-a-11 | fenchlorazole-ethyl |
| I-a-11 | isoxadifen-ethyl |
| I-a-11 | mefenpyr-diethyl |
| I-a-11 | fenclorim |
| I-a-11 | cumyluron |
| I-a-11 | S4-1 |
| I-a-11 | S4-5 |
| I-a-12 | cloquintocet-mexyl |
| I-a-12 | fenchlorazole-ethyl |
| I-a-12 | isoxadifen-ethyl |
| I-a-12 | mefenpyr-diethyl |
| I-a-12 | fenclorim |
| I-a-12 | cumyluron |
| I-a-12 | S4-1 |
| I-a-12 | S4-5 |
| I-a-13 | cloquintocet-mexyl |
| I-a-13 | fenchlorazole-ethyl |
| I-a-13 | isoxadifen-ethyl |

-continued

| Active compound of the formula | Safener |
|---|---|
| I-a-13 | mefenpyr-diethyl |
| I-a-13 | fenclorim |
| I-a-13 | cumyluron |
| I-a-13 | S4-1 |
| I-a-13 | S4-5 |
| I-a-14 | cloquintocet-mexyl |
| I-a-14 | fenchlorazole-ethyl |
| I-a-14 | isoxadifen-ethyl |
| I-a-14 | mefenpyr-diethyl |
| I-a-14 | fenclorim |
| I-a-14 | cumyluron |
| I-a-14 | S4-1 |
| I-a-14 | S4-5 |
| I-a-15 | cloquintocet-mexyl |
| I-a-15 | fenchlorazole-ethyl |
| I-a-15 | isoxadifen-ethyl |
| I-a-15 | mefenpyr-diethyl |
| I-a-15 | fenclorim |
| I-a-15 | cumyluron |
| I-a-15 | S4-1 |
| I-a-15 | S4-5 |
| I-a-16 | cloquintocet-mexyl |
| I-a-16 | fenchlorazole-ethyl |
| I-a-16 | isoxadifen-ethyl |
| I-a-16 | mefenpyr-diethyl |
| I-a-16 | fenclorim |
| I-a-16 | cumyluron |
| I-a-16 | S4-1 |
| I-a-16 | S4-5 |
| I-a-17 | cloquintocet-mexyl |
| I-a-17 | fenchlorazole-ethyl |
| I-a-17 | isoxadifen-ethyl |
| I-a-17 | mefenpyr-diethyl |
| I-a-17 | fenclorim |
| I-a-17 | cumyluron |
| I-a-17 | S4-1 |
| I-a-17 | S4-5 |
| I-a-18 | cloquintocet-mexyl |
| I-a-18 | fenchlorazole-ethyl |
| I-a-18 | isoxadifen-ethyl |
| I-a-18 | mefenpyr-diethyl |
| I-a-18 | fenclorim |
| I-a-18 | cumyluron |
| I-a-18 | S4-1 |
| I-a-18 | S4-5 |
| I-a-19 | cloquintocet-mexyl |
| I-a-19 | fenchlorazole-ethyl |
| I-a-19 | isoxadifen-ethyl |
| I-a-19 | mefenpyr-diethyl |
| I-a-19 | fenclorim |
| I-a-19 | cumyluron |
| I-a-19 | S4-1 |
| I-a-19 | S4-5 |
| I-a-20 | cloquintocet-mexyl |
| I-a-20 | fenchlorazole-ethyl |
| I-a-20 | isoxadifen-ethyl |
| I-a-20 | mefenpyr-diethyl |
| I-a-20 | fenclorim |
| I-a-20 | cumyluron |
| I-a-20 | S4-1 |
| I-a-20 | S4-5 |
| I-a-21 | cloquintocet-mexyl |
| I-a-21 | fenchlorazole-ethyl |
| I-a-21 | isoxadifen-ethyl |
| I-a-21 | mefenpyr-diethyl |
| I-a-21 | fenclorim |
| I-a-21 | cumyluron |
| I-a-21 | S4-1 |
| I-a-21 | S4-5 |
| I-a-22 | cloquintocet-mexyl |
| I-a-22 | fenchlorazole-ethyl |
| I-a-22 | isoxadifen-ethyl |
| I-a-22 | mefenpyr-diethyl |
| I-a-22 | fenclorim |
| I-a-22 | cumyluron |
| I-a-22 | S4-1 |
| I-a-22 | S4-5 |

-continued

| Active compound of the formula | Safener |
|---|---|
| I-a-23 | cloquintocet-mexyl |
| I-a-23 | fenchlorazole-ethyl |
| I-a-23 | isoxadifen-ethyl |
| I-a-23 | mefenpyr-diethyl |
| I-a-23 | fenclorim |
| I-a-23 | cumyluron |
| I-a-23 | S4-1 |
| I-a-23 | S4-5 |
| I-a-24 | cloquintocet-mexyl |
| I-a-24 | fenchlorazole-ethyl |
| I-a-24 | isoxadifen-ethyl |
| I-a-24 | mefenpyr-diethyl |
| I-a-24 | fenclorim |
| I-a-24 | cumyluron |
| I-a-24 | S4-1 |
| I-a-24 | S4-5 |
| I-a-25 | cloquintocet-mexyl |
| I-a-25 | fenchlorazole-ethyl |
| I-a-25 | isoxadifen-ethyl |
| I-a-25 | mefenpyr-diethyl |
| I-a-25 | fenclorim |
| I-a-25 | cumyluron |
| I-a-25 | S4-1 |
| I-a-25 | S4-5 |
| I-a-26 | cloquintocet-mexyl |
| I-a-26 | fenchlorazole-ethyl |
| I-a-26 | isoxadifen-ethyl |
| I-a-26 | mefenpyr-diethyl |
| I-a-26 | fenclorim |
| I-a-26 | cumyluron |
| I-a-26 | S4-1 |
| I-a-26 | S4-5 |
| I-a-27 | cloquintocet-mexyl |
| I-a-27 | fenchlorazole-ethyl |
| I-a-27 | isoxadifen-ethyl |
| I-a-27 | mefenpyr-diethyl |
| I-a-27 | fenclorim |
| I-a-27 | cumyluron |
| I-a-27 | S4-1 |
| I-a-27 | S4-5 |
| I-a-28 | cloquintocet-mexyl |
| I-a-28 | fenchlorazole-ethyl |
| I-a-28 | isoxadifen-ethyl |
| I-a-28 | mefenpyr-diethyl |
| I-a-28 | fenclorim |
| I-a-28 | cumyluron |
| I-a-28 | S4-1 |
| I-a-28 | S4-5 |
| I-a-29 | cloquintocet-mexyl |
| I-a-29 | fenchlorazole-ethyl |
| I-a-29 | isoxadifen-ethyl |
| I-a-29 | mefenpyr-diethyl |
| I-a-29 | fenclorim |
| I-a-29 | cumyluron |
| I-a-29 | S4-1 |
| I-a-29 | S4-5 |
| I-a-30 | cloquintocet-mexyl |
| I-a-30 | fenchlorazole-ethyl |
| I-a-30 | isoxadifen-ethyl |
| I-a-30 | mefenpyr-diethyl |
| I-a-30 | fenclorim |
| I-a-30 | cumyluron |
| I-a-30 | S4-1 |
| I-a-30 | S4-5 |
| I-a-31 | cloquintocet-mexyl |
| I-a-31 | fenchlorazole-ethyl |
| I-a-31 | isoxadifen-ethyl |
| I-a-31 | mefenpyr-diethyl |
| I-a-31 | fenclorim |
| I-a-31 | cumyluron |
| I-a-31 | S4-1 |
| I-a-31 | S4-5 |
| I-a-32 | cloquintocet-mexyl |
| I-a-32 | fenchlorazole-ethyl |
| I-a-32 | isoxadifen-ethyl |
| I-a-32 | mefenpyr-diethyl |
| I-a-32 | fenclorim |

| Active compound of the formula | Safener |
|---|---|
| I-a-32 | cumyluron |
| I-a-32 | S4-1 |
| I-a-32 | S4-5 |
| I-a-33 | cloquintocet-mexyl |
| I-a-33 | fenchlorazole-ethyl |
| I-a-33 | isoxadifen-ethyl |
| I-a-33 | mefenpyr-diethyl |
| I-a-33 | fenclorim |
| I-a-33 | cumyluron |
| I-a-33 | S4-1 |
| I-a-33 | S4-5 |
| I-a-34 | cloquintocet-mexyl |
| I-a-34 | fenchlorazole-ethyl |
| I-a-34 | isoxadifen-ethyl |
| I-a-34 | mefenpyr-diethyl |
| I-a-34 | fenclorim |
| I-a-34 | cumyluron |
| I-a-34 | S4-1 |
| I-a-34 | S4-5 |
| I-a-35 | cloquintocet-mexyl |
| I-a-35 | fenchlorazole-ethyl |
| I-a-35 | isoxadifen-ethyl |
| I-a-35 | mefenpyr-diethyl |
| I-a-35 | fenclorim |
| I-a-35 | cumyluron |
| I-a-35 | S4-1 |
| I-a-35 | S4-5 |
| I-a-36 | cloquintocet-mexyl |
| I-a-36 | fenchlorazole-ethyl |
| I-a-36 | isoxadifen-ethyl |
| I-a-36 | mefenpyr-diethyl |
| I-a-36 | fenclorim |
| I-a-36 | cumyluron |
| I-a-36 | S4-1 |
| I-a-36 | S4-5 |
| I-a-37 | cloquintocet-mexyl |
| I-a-37 | fenchlorazole-ethyl |
| I-a-37 | isoxadifen-ethyl |
| I-a-37 | mefenpyr-diethyl |
| I-a-37 | fenclorim |
| I-a-37 | cumyluron |
| I-a-37 | S4-1 |
| I-a-37 | S4-5 |
| I-a-38 | cloquintocet-mexyl |
| I-a-38 | fenchlorazole-ethyl |
| I-a-38 | isoxadifen-ethyl |
| I-a-38 | mefenpyr-diethyl |
| I-a-38 | fenclorim |
| I-a-38 | cumyluron |
| I-a-38 | S4-1 |
| I-a-38 | S4-5 |
| I-a-39 | cloquintocet-mexyl |
| I-a-39 | fenchlorazole-ethyl |
| I-a-39 | isoxadifen-ethyl |
| I-a-39 | mefenpyr-diethyl |
| I-a-39 | fenclorim |
| I-a-39 | cumyluron |
| I-a-39 | S4-1 |
| I-a-39 | S4-5 |
| I-a-40 | cloquintocet-mexyl |
| I-a-40 | fenchlorazole-ethyl |
| I-a-40 | isoxadifen-ethyl |
| I-a-40 | mefenpyr-diethyl |
| I-a-40 | fenclorim |
| I-a-40 | cumyluron |
| I-a-40 | S4-1 |
| I-a-40 | S4-5 |
| I-a-41 | cloquintocet-mexyl |
| I-a-41 | fenchlorazole-ethyl |
| I-a-41 | isoxadifen-ethyl |
| I-a-41 | mefenpyr-diethyl |
| I-a-41 | fenclorim |
| I-a-41 | cumyluron |
| I-a-41 | S4-1 |
| I-a-41 | S4-5 |
| I-a-42 | cloquintocet-mexyl |
| I-a-42 | fenchlorazole-ethyl |
| I-a-42 | isoxadifen-ethyl |
| I-a-42 | mefenpyr-diethyl |
| I-a-42 | fenclorim |
| I-a-42 | cumyluron |
| I-a-42 | S4-1 |
| I-a-42 | S4-5 |
| I-a-43 | cloquintocet-mexyl |
| I-a-43 | fenchlorazole-ethyl |
| I-a-43 | isoxadifen-ethyl |
| I-a-43 | mefenpyr-diethyl |
| I-a-43 | fenclorim |
| I-a-43 | cumyluron |
| I-a-43 | S4-1 |
| I-a-43 | S4-5 |
| I-a-44 | cloquintocet-mexyl |
| I-a-44 | fenchlorazole-ethyl |
| I-a-44 | isoxadifen-ethyl |
| I-a-44 | mefenpyr-diethyl |
| I-a-44 | fenclorim |
| I-a-44 | cumyluron |
| I-a-44 | S4-1 |
| I-a-44 | S4-5 |
| I-a-45 | cloquintocet-mexyl |
| I-a-45 | fenchlorazole-ethyl |
| I-a-45 | isoxadifen-ethyl |
| I-a-45 | mefenpyr-diethyl |
| I-a-45 | fenclorim |
| I-a-45 | cumyluron |
| I-a-45 | S4-1 |
| I-a-45 | S4-5 |
| I-a-46 | cloquintocet-mexyl |
| I-a-46 | fenchlorazole-ethyl |
| I-a-46 | isoxadifen-ethyl |
| I-a-46 | mefenpyr-diethyl |
| I-a-46 | fenclorim |
| I-a-46 | cumyluron |
| I-a-46 | S4-1 |
| I-a-46 | S4-5 |
| I-a-47 | cloquintocet-mexyl |
| I-a-47 | fenchlorazole-ethyl |
| I-a-47 | isoxadifen-ethyl |
| I-a-47 | mefenpyr-diethyl |
| I-a-47 | fenclorim |
| I-a-47 | cumyluron |
| I-a-47 | S4-1 |
| I-a-47 | S4-5 |
| I-a-48 | cloquintocet-mexyl |
| I-a-48 | fenchlorazole-ethyl |
| I-a-48 | isoxadifen-ethyl |
| I-a-48 | mefenpyr-diethyl |
| I-a-48 | fenclorim |
| I-a-48 | cumyluron |
| I-a-48 | S4-1 |
| I-a-48 | S4-5 |
| I-a-49 | cloquintocet-mexyl |
| I-a-49 | fenchlorazole-ethyl |
| I-a-49 | isoxadifen-ethyl |
| I-a-49 | mefenpyr-diethyl |
| I-a-49 | fenclorim |
| I-a-49 | cumyluron |
| I-a-49 | S4-1 |
| I-a-49 | S4-5 |
| I-a-50 | cloquintocet-mexyl |
| I-a-50 | fenchlorazole-ethyl |
| I-a-50 | isoxadifen-ethyl |
| I-a-50 | mefenpyr-diethyl |
| I-a-50 | fenclorim |
| I-a-50 | cumyluron |
| I-a-50 | S4-1 |
| I-a-50 | S4-5 |
| I-a-51 | cloquintocet-mexyl |
| I-a-51 | fenchlorazole-ethyl |
| I-a-51 | isoxadifen-ethyl |
| I-a-51 | mefenpyr-diethyl |
| I-a-51 | fenclorim |
| I-a-51 | cumyluron |
| I-a-51 | S4-1 |

| Active compound of the formula | Safener |
|---|---|
| I-a-51 | S4-5 |
| I-a-52 | cloquintocet-mexyl |
| I-a-52 | fenchlorazole-ethyl |
| I-a-52 | isoxadifen-ethyl |
| I-a-52 | mefenpyr-diethyl |
| I-a-52 | fenclorim |
| I-a-52 | cumyluron |
| I-a-52 | S4-1 |
| I-a-52 | S4-5 |
| I-a-53 | cloquintocet-mexyl |
| I-a-53 | fenchlorazole-ethyl |
| I-a-53 | isoxadifen-ethyl |
| I-a-53 | mefenpyr-diethyl |
| I-a-53 | fenclorim |
| I-a-53 | cumyluron |
| I-a-53 | S4-1 |
| I-a-53 | S4-5 |
| I-a-54 | cloquintocet-mexyl |
| I-a-54 | fenchlorazole-ethyl |
| I-a-54 | isoxadifen-ethyl |
| I-a-54 | mefenpyr-diethyl |
| I-a-54 | fenclorim |
| I-a-54 | cumyluron |
| I-a-54 | S4-1 |
| I-a-54 | S4-5 |
| I-a-55 | cloquintocet-mexyl |
| I-a-55 | fenchlorazole-ethyl |
| I-a-55 | isoxadifen-ethyl |
| I-a-55 | mefenpyr-diethyl |
| I-a-55 | fenclorim |
| I-a-55 | cumyluron |
| I-a-55 | S4-1 |
| I-a-55 | S4-5 |
| I-a-56 | cloquintocet-mexyl |
| I-a-56 | fenchlorazole-ethyl |
| I-a-56 | isoxadifen-ethyl |
| I-a-56 | mefenpyr-diethyl |
| I-a-56 | fenclorim |
| I-a-56 | cumyluron |
| I-a-56 | S4-1 |
| I-a-56 | S4-5 |
| I-a-57 | cloquintocet-mexyl |
| I-a-57 | fenchlorazole-ethyl |
| I-a-57 | isoxadifen-ethyl |
| I-a-57 | mefenpyr-diethyl |
| I-a-57 | fenclorim |
| I-a-57 | cumyluron |
| I-a-57 | S4-1 |
| I-a-57 | S4-5 |
| I-a-58 | cloquintocet-mexyl |
| I-a-58 | fenchlorazole-ethyl |
| I-a-58 | isoxadifen-ethyl |
| I-a-58 | mefenpyr-diethyl |
| I-a-58 | fenclorim |
| I-a-58 | cumyluron |
| I-a-58 | S4-1 |
| I-a-58 | S4-5 |
| I-a-59 | cloquintocet-mexyl |
| I-a-59 | fenchlorazole-ethyl |
| I-a-59 | isoxadifen-ethyl |
| I-a-59 | mefenpyr-diethyl |
| I-a-59 | fenclorim |
| I-a-59 | cumyluron |
| I-a-59 | S4-1 |
| I-a-59 | S4-5 |
| I-a-60 | cloquintocet-mexyl |
| I-a-60 | fenchlorazole-ethyl |
| I-a-60 | isoxadifen-ethyl |
| I-a-60 | mefenpyr-diethyl |
| I-a-60 | fenclorim |
| I-a-60 | cumyluron |
| I-a-60 | S4-1 |
| I-a-60 | S4-5 |
| I-a-61 | cloquintocet-mexyl |
| I-a-61 | fenchlorazole-ethyl |
| I-a-61 | isoxadifen-ethyl |
| I-a-61 | mefenpyr-diethyl |
| I-a-61 | fenclorim |
| I-a-61 | cumyluron |
| I-a-61 | S4-1 |
| I-a-61 | S4-5 |
| I-a-62 | cloquintocet-mexyl |
| I-a-62 | fenchlorazole-ethyl |
| I-a-62 | isoxadifen-ethyl |
| I-a-62 | mefenpyr-diethyl |
| I-a-62 | fenclorim |
| I-a-62 | cumyluron |
| I-a-62 | S4-1 |
| I-a-62 | S4-5 |
| I-a-63 | cloquintocet-mexyl |
| I-a-63 | fenchlorazole-ethyl |
| I-a-63 | isoxadifen-ethyl |
| I-a-63 | mefenpyr-diethyl |
| I-a-63 | fenclorim |
| I-a-63 | cumyluron |
| I-a-63 | S4-1 |
| I-a-63 | S4-5 |
| I-a-64 | cloquintocet-mexyl |
| I-a-64 | fenchlorazole-ethyl |
| I-a-64 | isoxadifen-ethyl |
| I-a-64 | mefenpyr-diethyl |
| I-a-64 | fenclorim |
| I-a-64 | cumyluron |
| I-a-64 | S4-1 |
| I-a-64 | S4-5 |
| I-a-65 | cloquintocet-mexyl |
| I-a-65 | fenchlorazole-ethyl |
| I-a-65 | isoxadifen-ethyl |
| I-a-65 | mefenpyr-diethyl |
| I-a-65 | fenclorim |
| I-a-65 | cumyluron |
| I-a-65 | S4-1 |
| I-a-65 | S4-5 |
| I-a-66 | cloquintocet-mexyl |
| I-a-66 | fenchlorazole-ethyl |
| I-a-66 | isoxadifen-ethyl |
| I-a-66 | mefenpyr-diethyl |
| I-a-66 | fenclorim |
| I-a-66 | cumyluron |
| I-a-66 | S4-1 |
| I-a-66 | S4-5 |
| I-a-67 | cloquintocet-mexyl |
| I-a-67 | fenchlorazole-ethyl |
| I-a-67 | isoxadifen-ethyl |
| I-a-67 | mefenpyr-diethyl |
| I-a-67 | fenclorim |
| I-a-67 | cumyluron |
| I-a-67 | S4-1 |
| I-a-67 | S4-5 |
| I-a-68 | cloquintocet-mexyl |
| I-a-68 | fenchlorazole-ethyl |
| I-a-68 | isoxadifen-ethyl |
| I-a-68 | mefenpyr-diethyl |
| I-a-68 | fenclorim |
| I-a-68 | cumyluron |
| I-a-68 | S4-1 |
| I-a-68 | S4-5 |
| I-a-69 | cloquintocet-mexyl |
| I-a-69 | fenchlorazole-ethyl |
| I-a-69 | isoxadifen-ethyl |
| I-a-69 | mefenpyr-diethyl |
| I-a-69 | fenclorim |
| I-a-69 | cumyluron |
| I-a-69 | S4-1 |
| I-a-69 | S4-5 |
| I-a-70 | cloquintocet-mexyl |
| I-a-70 | fenchlorazole-ethyl |
| I-a-70 | isoxadifen-ethyl |
| I-a-70 | mefenpyr-diethyl |
| I-a-70 | fenclorim |
| I-a-70 | cumyluron |
| I-a-70 | S4-1 |
| I-a-70 | S4-5 |
| I-a-71 | cloquintocet-mexyl |

| Active compound of the formula | Safener |
|---|---|
| I-a-71 | fenchlorazole-ethyl |
| I-a-71 | isoxadifen-ethyl |
| I-a-71 | mefenpyr-diethyl |
| I-a-71 | fenclorim |
| I-a-71 | cumyluron |
| I-a-71 | S4-1 |
| I-a-71 | S4-5 |
| I-a-72 | cloquintocet-mexyl |
| I-a-72 | fenchlorazole-ethyl |
| I-a-72 | isoxadifen-ethyl |
| I-a-72 | mefenpyr-diethyl |
| I-a-72 | fenclorim |
| I-a-72 | cumyluron |
| I-a-72 | S4-1 |
| I-a-72 | S4-5 |
| I-a-73 | cloquintocet-mexyl |
| I-a-73 | fenchlorazole-ethyl |
| I-a-73 | isoxadifen-ethyl |
| I-a-73 | mefenpyr-diethyl |
| I-a-73 | fenclorim |
| I-a-73 | cumyluron |
| I-a-73 | S4-1 |
| I-a-73 | S4-5 |
| I-a-74 | cloquintocet-mexyl |
| I-a-74 | fenchlorazole-ethyl |
| I-a-74 | isoxadifen-ethyl |
| I-a-74 | mefenpyr-diethyl |
| I-a-74 | fenclorim |
| I-a-74 | cumyluron |
| I-a-74 | S4-1 |
| I-a-74 | S4-5 |
| I-a-75 | cloquintocet-mexyl |
| I-a-75 | fenchlorazole-ethyl |
| I-a-75 | isoxadifen-ethyl |
| I-a-75 | mefenpyr-diethyl |
| I-a-75 | fenclorim |
| I-a-75 | cumyluron |
| I-a-75 | S4-1 |
| I-a-75 | S4-5 |
| I-b-1 | cloquintocet-mexyl |
| I-b-1 | fenchlorazole-ethyl |
| I-b-1 | isoxadifen-ethyl |
| I-b-1 | mefenpyr-diethyl |
| I-b-1 | fenclorim |
| I-b-1 | cumyluron |
| I-b-1 | S4-1 |
| I-b-1 | S4-5 |
| I-b-2 | cloquintocet-mexyl |
| I-b-2 | fenchlorazole-ethyl |
| I-b-2 | isoxadifen-ethyl |
| I-b-2 | mefenpyr-diethyl |
| I-b-2 | fenclorim |
| I-b-2 | cumyluron |
| I-b-2 | S4-1 |
| I-b-2 | S4-5 |
| I-b-3 | cloquintocet-mexyl |
| I-b-3 | fenchlorazole-ethyl |
| I-b-3 | isoxadifen-ethyl |
| I-b-3 | mefenpyr-diethyl |
| I-b-3 | fenclorim |
| I-b-3 | cumyluron |
| I-b-3 | S4-1 |
| I-b-3 | S4-5 |
| I-b-4 | cloquintocet-mexyl |
| I-b-4 | fenchlorazole-ethyl |
| I-b-4 | isoxadifen-ethyl |
| I-b-4 | mefenpyr-diethyl |
| I-b-4 | fenclorim |
| I-b-4 | cumyluron |
| I-b-4 | S4-1 |
| I-b-4 | S4-5 |
| I-b-5 | cloquintocet-mexyl |
| I-b-5 | fenchlorazole-ethyl |
| I-b-5 | isoxadifen-ethyl |
| I-b-5 | mefenpyr-diethyl |
| I-b-5 | fenclorim |
| I-b-5 | cumyluron |
| I-b-5 | S4-1 |
| I-b-5 | S4-5 |
| I-b-6 | cloquintocet-mexyl |
| I-b-6 | fenchlorazole-ethyl |
| I-b-6 | isoxadifen-ethyl |
| I-b-6 | mefenpyr-diethyl |
| I-b-6 | fenclorim |
| I-b-6 | cumyluron |
| I-b-6 | S4-1 |
| I-b-6 | S4-5 |
| I-b-7 | cloquintocet-mexyl |
| I-b-7 | fenchlorazole-ethyl |
| I-b-7 | isoxadifen-ethyl |
| I-b-7 | mefenpyr-diethyl |
| I-b-7 | fenclorim |
| I-b-7 | cumyluron |
| I-b-7 | S4-1 |
| I-b-7 | S4-5 |
| I-b-8 | cloquintocet-mexyl |
| I-b-8 | fenchlorazole-ethyl |
| I-b-8 | isoxadifen-ethyl |
| I-b-8 | mefenpyr-diethyl |
| I-b-8 | fenclorim |
| I-b-8 | cumyluron |
| I-b-8 | S4-1 |
| I-b-8 | S4-5 |
| I-b-9 | cloquintocet-mexyl |
| I-b-9 | fenchlorazole-ethyl |
| I-b-9 | isoxadifen-ethyl |
| I-b-9 | mefenpyr-diethyl |
| I-b-9 | fenclorim |
| I-b-9 | cumyluron |
| I-b-9 | S4-1 |
| I-b-9 | S4-5 |
| I-b-10 | cloquintocet-mexyl |
| I-b-10 | fenchlorazole-ethyl |
| I-b-10 | isoxadifen-ethyl |
| I-b-10 | mefenpyr-diethyl |
| I-b-10 | fenclorim |
| I-b-10 | cumyluron |
| I-b-10 | S4-1 |
| I-b-10 | S4-5 |
| I-b-11 | cloquintocet-mexyl |
| I-b-11 | fenchlorazole-ethyl |
| I-b-11 | isoxadifen-ethyl |
| I-b-11 | mefenpyr-diethyl |
| I-b-11 | fenclorim |
| I-b-11 | cumyluron |
| I-b-11 | S4-1 |
| I-b-11 | S4-5 |
| I-b-12 | cloquintocet-mexyl |
| I-b-12 | fenchlorazole-ethyl |
| I-b-12 | isoxadifen-ethyl |
| I-b-12 | mefenpyr-diethyl |
| I-b-12 | fenclorim |
| I-b-12 | cumyluron |
| I-b-12 | S4-1 |
| I-b-12 | S4-5 |
| I-b-13 | cloquintocet-mexyl |
| I-b-13 | fenchlorazole-ethyl |
| I-b-13 | isoxadifen-ethyl |
| I-b-13 | mefenpyr-diethyl |
| I-b-13 | fenclorim |
| I-b-13 | cumyluron |
| I-b-13 | S4-1 |
| I-b-13 | S4-5 |
| I-b-14 | cloquintocet-mexyl |
| I-b-14 | fenchlorazole-ethyl |
| I-b-14 | isoxadifen-ethyl |
| I-b-14 | mefenpyr-diethyl |
| I-b-14 | fenclorim |
| I-b-14 | cumyluron |
| I-b-14 | S4-1 |
| I-b-14 | S4-5 |
| I-b-15 | cloquintocet-mexyl |
| I-b-15 | fenchlorazole-ethyl |
| I-b-15 | isoxadifen-ethyl |

| Active compound of the formula | Safener |
|---|---|
| I-b-15 | mefenpyr-diethyl |
| I-b-15 | fenclorim |
| I-b-15 | cumyluron |
| I-b-15 | S4-1 |
| I-b-15 | S4-5 |
| I-b-16 | cloquintocet-mexyl |
| I-b-16 | fenchlorazole-ethyl |
| I-b-16 | isoxadifen-ethyl |
| I-b-16 | mefenpyr-diethyl |
| I-b-16 | fenclorim |
| I-b-16 | cumyluron |
| I-b-16 | S4-1 |
| I-b-16 | S4-5 |
| I-b-17 | cloquintocet-mexyl |
| I-b-17 | fenchlorazole-ethyl |
| I-b-17 | isoxadifen-ethyl |
| I-b-17 | mefenpyr-diethyl |
| I-b-17 | fenclorim |
| I-b-17 | cumyluron |
| I-b-17 | S4-1 |
| I-b-17 | S4-5 |
| I-b-18 | cloquintocet-mexyl |
| I-b-18 | fenchlorazole-ethyl |
| I-b-18 | isoxadifen-ethyl |
| I-b-18 | mefenpyr-diethyl |
| I-b-18 | fenclorim |
| I-b-18 | cumyluron |
| I-b-18 | S4-1 |
| I-b-18 | S4-5 |
| I-b-19 | cloquintocet-mexyl |
| I-b-19 | fenchlorazole-ethyl |
| I-b-19 | isoxadifen-ethyl |
| I-b-19 | mefenpyr-diethyl |
| I-b-19 | fenclorim |
| I-b-19 | cumyluron |
| I-b-19 | S4-1 |
| I-b-19 | S4-5 |
| I-b-20 | cloquintocet-mexyl |
| I-b-20 | fenchlorazole-ethyl |
| I-b-20 | isoxadifen-ethyl |
| I-b-20 | mefenpyr-diethyl |
| I-b-20 | fenclorim |
| I-b-20 | cumyluron |
| I-b-20 | S4-1 |
| I-b-20 | S4-5 |
| I-b-21 | cloquintocet-mexyl |
| I-b-21 | fenchlorazole-ethyl |
| I-b-21 | isoxadifen-ethyl |
| I-b-21 | mefenpyr-diethyl |
| I-b-21 | fenclorim |
| I-b-21 | cumyluron |
| I-b-21 | S4-1 |
| I-b-21 | S4-5 |
| I-b-22 | cloquintocet-mexyl |
| I-b-22 | fenchlorazole-ethyl |
| I-b-22 | isoxadifen-ethyl |
| I-b-22 | mefenpyr-diethyl |
| I-b-22 | fenclorim |
| I-b-22 | cumyluron |
| I-b-22 | S4-1 |
| I-b-22 | S4-5 |
| I-b-23 | cloquintocet-mexyl |
| I-b-23 | fenchlorazole-ethyl |
| I-b-23 | isoxadifen-ethyl |
| I-b-23 | mefenpyr-diethyl |
| I-b-23 | fenclorim |
| I-b-23 | cumyluron |
| I-b-23 | S4-1 |
| I-b-23 | S4-5 |
| I-b-24 | cloquintocet-mexyl |
| I-b-24 | fenchlorazole-ethyl |
| I-b-24 | isoxadifen-ethyl |
| I-b-24 | mefenpyr-diethyl |
| I-b-24 | fenclorim |
| I-b-24 | cumyluron |
| I-b-24 | S4-1 |
| I-b-24 | S4-5 |
| I-b-25 | cloquintocet-mexyl |
| I-b-25 | fenchlorazole-ethyl |
| I-b-25 | isoxadifen-ethyl |
| I-b-25 | mefenpyr-diethyl |
| I-b-25 | fenclorim |
| I-b-25 | cumyluron |
| I-b-25 | S4-1 |
| I-b-25 | S4-5 |
| I-b-26 | cloquintocet-mexyl |
| I-b-26 | fenchlorazole-ethyl |
| I-b-26 | isoxadifen-ethyl |
| I-b-26 | mefenpyr-diethyl |
| I-b-26 | fenclorim |
| I-b-26 | cumyluron |
| I-b-26 | S4-1 |
| I-b-26 | S4-5 |
| I-b-27 | cloquintocet-mexyl |
| I-b-27 | fenchlorazole-ethyl |
| I-b-27 | isoxadifen-ethyl |
| I-b-27 | mefenpyr-diethyl |
| I-b-27 | fenclorim |
| I-b-27 | cumyluron |
| I-b-27 | S4-1 |
| I-b-27 | S4-5 |
| I-b-28 | cloquintocet-mexyl |
| I-b-28 | fenchlorazole-ethyl |
| I-b-28 | isoxadifen-ethyl |
| I-b-28 | mefenpyr-diethyl |
| I-b-28 | fenclorim |
| I-b-28 | cumyluron |
| I-b-28 | S4-1 |
| I-b-28 | S4-5 |
| I-b-29 | cloquintocet-mexyl |
| I-b-29 | fenchlorazole-ethyl |
| I-b-29 | isoxadifen-ethyl |
| I-b-29 | mefenpyr-diethyl |
| I-b-29 | fenclorim |
| I-b-29 | cumyluron |
| I-b-29 | S4-1 |
| I-b-29 | S4-5 |
| I-b-30 | cloquintocet-mexyl |
| I-b-30 | fenchlorazole-ethyl |
| I-b-30 | isoxadifen-ethyl |
| I-b-30 | mefenpyr-diethyl |
| I-b-30 | fenclorim |
| I-b-30 | cumyluron |
| I-b-30 | S4-1 |
| I-b-30 | S4-5 |
| I-b-31 | cloquintocet-mexyl |
| I-b-31 | fenchlorazole-ethyl |
| I-b-31 | isoxadifen-ethyl |
| I-b-31 | mefenpyr-diethyl |
| I-b-31 | fenclorim |
| I-b-31 | cumyluron |
| I-b-31 | S4-1 |
| I-b-31 | S4-5 |
| I-b-32 | cloquintocet-mexyl |
| I-b-32 | fenchlorazole-ethyl |
| I-b-32 | isoxadifen-ethyl |
| I-b-32 | mefenpyr-diethyl |
| I-b-32 | fenclorim |
| I-b-32 | cumyluron |
| I-b-32 | S4-1 |
| I-b-32 | S4-5 |
| I-b-33 | cloquintocet-mexyl |
| I-b-33 | fenchlorazole-ethyl |
| I-b-33 | isoxadifen-ethyl |
| I-b-33 | mefenpyr-diethyl |
| I-b-33 | fenclorim |
| I-b-33 | cumyluron |
| I-b-33 | S4-1 |
| I-b-33 | S4-5 |
| I-b-34 | cloquintocet-mexyl |
| I-b-34 | fenchlorazole-ethyl |
| I-b-34 | isoxadifen-ethyl |
| I-b-34 | mefenpyr-diethyl |
| I-b-34 | fenclorim |

| Active compound of the formula | Safener |
|---|---|
| I-b-34 | cumyluron |
| I-b-34 | S4-1 |
| I-b-34 | S4-5 |
| I-b-35 | cloquintocet-mexyl |
| I-b-35 | fenchlorazole-ethyl |
| I-b-35 | isoxadifen-ethyl |
| I-b-35 | mefenpyr-diethyl |
| I-b-35 | fenclorim |
| I-b-35 | cumyluron |
| I-b-35 | S4-1 |
| I-b-35 | S4-5 |
| I-b-36 | cloquintocet-mexyl |
| I-b-36 | fenchlorazole-ethyl |
| I-b-36 | isoxadifen-ethyl |
| I-b-36 | mefenpyr-diethyl |
| I-b-36 | fenclorim |
| I-b-36 | cumyluron |
| I-b-36 | S4-1 |
| I-b-36 | S4-5 |
| I-b-37 | cloquintocet-mexyl |
| I-b-37 | fenchlorazole-ethyl |
| I-b-37 | isoxadifen-ethyl |
| I-b-37 | mefenpyr-diethyl |
| I-b-37 | fenclorim |
| I-b-37 | cumyluron |
| I-b-37 | S4-1 |
| I-b-37 | S4-5 |
| I-b-38 | cloquintocet-mexyl |
| I-b-38 | fenchlorazole-ethyl |
| I-b-38 | isoxadifen-ethyl |
| I-b-38 | mefenpyr-diethyl |
| I-b-38 | fenclorim |
| I-b-38 | cumyluron |
| I-b-38 | S4-1 |
| I-b-38 | S4-5 |
| I-b-39 | cloquintocet-mexyl |
| I-b-39 | fenchlorazole-ethyl |
| I-b-39 | isoxadifen-ethyl |
| I-b-39 | mefenpyr-diethyl |
| I-b-39 | fenclorim |
| I-b-39 | cumyluron |
| I-b-39 | S4-1 |
| I-b-39 | S4-5 |
| I-b-40 | cloquintocet-mexyl |
| I-b-40 | fenchlorazole-ethyl |
| I-b-40 | isoxadifen-ethyl |
| I-b-40 | mefenpyr-diethyl |
| I-b-40 | fenclorim |
| I-b-40 | cumyluron |
| I-b-40 | S4-1 |
| I-b-40 | S4-5 |
| I-b-41 | cloquintocet-mexyl |
| I-b-41 | fenchlorazole-ethyl |
| I-b-41 | isoxadifen-ethyl |
| I-b-41 | mefenpyr-diethyl |
| I-b-41 | fenclorim |
| I-b-41 | cumyluron |
| I-b-41 | S4-1 |
| I-b-41 | S4-5 |
| I-b-42 | cloquintocet-mexyl |
| I-b-42 | fenchlorazole-ethyl |
| I-b-42 | isoxadifen-ethyl |
| I-b-42 | mefenpyr-diethyl |
| I-b-42 | fenclorim |
| I-b-42 | cumyluron |
| I-b-42 | S4-1 |
| I-b-42 | S4-5 |
| I-b-43 | cloquintocet-mexyl |
| I-b-43 | fenchlorazole-ethyl |
| I-b-43 | isoxadifen-ethyl |
| I-b-43 | mefenpyr-diethyl |
| I-b-43 | fenclorim |
| I-b-43 | cumyluron |
| I-b-43 | S4-1 |
| I-b-43 | S4-5 |
| I-b-44 | cloquintocet-mexyl |
| I-b-44 | fenchlorazole-ethyl |
| I-b-44 | isoxadifen-ethyl |
| I-b-44 | mefenpyr-diethyl |
| I-b-44 | fenclorim |
| I-b-44 | cumyluron |
| I-b-44 | S4-1 |
| I-b-44 | S4-5 |
| I-b-45 | cloquintocet-mexyl |
| I-b-45 | fenchlorazole-ethyl |
| I-b-45 | isoxadifen-ethyl |
| I-b-45 | mefenpyr-diethyl |
| I-b-45 | fenclorim |
| I-b-45 | cumyluron |
| I-b-45 | S4-1 |
| I-b-45 | S4-5 |
| I-b-46 | cloquintocet-mexyl |
| I-b-46 | fenchlorazole-ethyl |
| I-b-46 | isoxadifen-ethyl |
| I-b-46 | mefenpyr-diethyl |
| I-b-46 | fenclorim |
| I-b-46 | cumyluron |
| I-b-46 | S4-1 |
| I-b-46 | S4-5 |
| I-b-47 | cloquintocet-mexyl |
| I-b-47 | fenchlorazole-ethyl |
| I-b-47 | isoxadifen-ethyl |
| I-b-47 | mefenpyr-diethyl |
| I-b-47 | fenclorim |
| I-b-47 | cumyluron |
| I-b-47 | S4-1 |
| I-b-47 | S4-5 |
| I-b-48 | cloquintocet-mexyl |
| I-b-48 | fenchlorazole-ethyl |
| I-b-48 | isoxadifen-ethyl |
| I-b-48 | mefenpyr-diethyl |
| I-b-48 | fenclorim |
| I-b-48 | cumyluron |
| I-b-48 | S4-1 |
| I-b-48 | S4-5 |
| I-b-49 | cloquintocet-mexyl |
| I-b-49 | fenchlorazole-ethyl |
| I-b-49 | isoxadifen-ethyl |
| I-b-49 | mefenpyr-diethyl |
| I-b-49 | fenclorim |
| I-b-49 | cumyluron |
| I-b-49 | S4-1 |
| I-b-49 | S4-5 |
| I-b-50 | cloquintocet-mexyl |
| I-b-50 | fenchlorazole-ethyl |
| I-b-50 | isoxadifen-ethyl |
| I-b-50 | mefenpyr-diethyl |
| I-b-50 | fenclorim |
| I-b-50 | cumyluron |
| I-b-50 | S4-1 |
| I-b-50 | S4-5 |
| I-b-51 | cloquintocet-mexyl |
| I-b-51 | fenchlorazole-ethyl |
| I-b-51 | isoxadifen-ethyl |
| I-b-51 | mefenpyr-diethyl |
| I-b-51 | fenclorim |
| I-b-51 | cumyluron |
| I-b-51 | S4-1 |
| I-b-51 | S4-5 |
| I-b-52 | cloquintocet-mexyl |
| I-b-52 | fenchlorazole-ethyl |
| I-b-52 | isoxadifen-ethyl |
| I-b-52 | mefenpyr-diethyl |
| I-b-52 | fenclorim |
| I-b-52 | cumyluron |
| I-b-52 | S4-1 |
| I-b-52 | S4-5 |
| I-b-53 | cloquintocet-mexyl |
| I-b-53 | fenchlorazole-ethyl |
| I-b-53 | isoxadifen-ethyl |
| I-b-53 | mefenpyr-diethyl |
| I-b-53 | fenclorim |
| I-b-53 | cumyluron |
| I-b-53 | S4-1 |

| Active compound of the formula | Safener |
|---|---|
| I-b-53 | S4-5 |
| I-b-54 | cloquintocet-mexyl |
| I-b-54 | fenchlorazole-ethyl |
| I-b-54 | isoxadifen-ethyl |
| I-b-54 | mefenpyr-diethyl |
| I-b-54 | fenclorim |
| I-b-54 | cumyluron |
| I-b-54 | S4-1 |
| I-b-54 | S4-5 |
| I-b-55 | cloquintocet-mexyl |
| I-b-55 | fenchlorazole-ethyl |
| I-b-55 | isoxadifen-ethyl |
| I-b-55 | mefenpyr-diethyl |
| I-b-55 | fenclorim |
| I-b-55 | cumyluron |
| I-b-55 | S4-1 |
| I-b-55 | S4-5 |
| I-b-56 | cloquintocet-mexyl |
| I-b-56 | fenchlorazole-ethyl |
| I-b-56 | isoxadifen-ethyl |
| I-b-56 | mefenpyr-diethyl |
| I-b-56 | fenclorim |
| I-b-56 | cumyluron |
| I-b-56 | S4-1 |
| I-b-56 | S4-5 |
| I-b-57 | cloquintocet-mexyl |
| I-b-57 | fenchlorazole-ethyl |
| I-b-57 | isoxadifen-ethyl |
| I-b-57 | mefenpyr-diethyl |
| I-b-57 | fenclorim |
| I-b-57 | cumyluron |
| I-b-57 | S4-1 |
| I-b-57 | S4-5 |
| I-b-58 | cloquintocet-mexyl |
| I-b-58 | fenchlorazole-ethyl |
| I-b-58 | isoxadifen-ethyl |
| I-b-58 | mefenpyr-diethyl |
| I-b-58 | fenclorim |
| I-b-58 | cumyluron |
| I-b-58 | S4-1 |
| I-b-58 | S4-5 |
| I-b-59 | cloquintocet-mexyl |
| I-b-59 | fenchlorazole-ethyl |
| I-b-59 | isoxadifen-ethyl |
| I-b-59 | mefenpyr-diethyl |
| I-b-59 | fenclorim |
| I-b-59 | cumyluron |
| I-b-59 | S4-1 |
| I-b-59 | S4-5 |
| I-b-60 | cloquintocet-mexyl |
| I-b-60 | fenchlorazole-ethyl |
| I-b-60 | isoxadifen-ethyl |
| I-b-60 | mefenpyr-diethyl |
| I-b-60 | fenclorim |
| I-b-60 | cumyluron |
| I-b-60 | S4-1 |
| I-b-60 | S4-5 |
| I-b-61 | cloquintocet-mexyl |
| I-b-61 | fenchlorazole-ethyl |
| I-b-61 | isoxadifen-ethyl |
| I-b-61 | mefenpyr-diethyl |
| I-b-61 | fenclorim |
| I-b-61 | cumyluron |
| I-b-61 | S4-1 |
| I-b-61 | S4-5 |
| I-b-62 | cloquintocet-mexyl |
| I-b-62 | fenchlorazole-ethyl |
| I-b-62 | isoxadifen-ethyl |
| I-b-62 | mefenpyr-diethyl |
| I-b-62 | fenclorim |
| I-b-62 | cumyluron |
| I-b-62 | S4-1 |
| I-b-62 | S4-5 |
| I-b-63 | cloquintocet-mexyl |
| I-b-63 | fenchlorazole-ethyl |
| I-b-63 | isoxadifen-ethyl |
| I-b-63 | mefenpyr-diethyl |
| I-b-63 | fenclorim |
| I-b-63 | cumyluron |
| I-b-63 | S4-1 |
| I-b-63 | S4-5 |
| I-b-64 | cloquintocet-mexyl |
| I-b-64 | fenchlorazole-ethyl |
| I-b-64 | isoxadifen-ethyl |
| I-b-64 | mefenpyr-diethyl |
| I-b-64 | fenclorim |
| I-b-64 | cumyluron |
| I-b-64 | S4-1 |
| I-b-64 | S4-5 |
| I-b-65 | cloquintocet-mexyl |
| I-b-65 | fenchlorazole-ethyl |
| I-b-65 | isoxadifen-ethyl |
| I-b-65 | mefenpyr-diethyl |
| I-b-65 | fenclorim |
| I-b-65 | cumyluron |
| I-b-65 | S4-1 |
| I-b-65 | S4-5 |
| I-b-66 | cloquintocet-mexyl |
| I-b-66 | fenchlorazole-ethyl |
| I-b-66 | isoxadifen-ethyl |
| I-b-66 | mefenpyr-diethyl |
| I-b-66 | fenclorim |
| I-b-66 | cumyluron |
| I-b-66 | S4-1 |
| I-b-66 | S4-5 |
| I-b-67 | cloquintocet-mexyl |
| I-b-67 | fenchlorazole-ethyl |
| I-b-67 | isoxadifen-ethyl |
| I-b-67 | mefenpyr-diethyl |
| I-b-67 | fenclorim |
| I-b-67 | cumyluron |
| I-b-67 | S4-1 |
| I-b-67 | S4-5 |
| I-b-68 | cloquintocet-mexyl |
| I-b-68 | fenchlorazole-ethyl |
| I-b-68 | isoxadifen-ethyl |
| I-b-68 | mefenpyr-diethyl |
| I-b-68 | fenclorim |
| I-b-68 | cumyluron |
| I-b-68 | S4-1 |
| I-b-68 | S4-5 |
| I-b-69 | cloquintocet-mexyl |
| I-b-69 | fenchlorazole-ethyl |
| I-b-69 | isoxadifen-ethyl |
| I-b-69 | mefenpyr-diethyl |
| I-b-69 | fenclorim |
| I-b-69 | cumyluron |
| I-b-69 | S4-1 |
| I-b-69 | S4-5 |
| I-b-70 | cloquintocet-mexyl |
| I-b-70 | fenchlorazole-ethyl |
| I-b-70 | isoxadifen-ethyl |
| I-b-70 | mefenpyr-diethyl |
| I-b-70 | fenclorim |
| I-b-70 | cumyluron |
| I-b-70 | S4-1 |
| I-b-70 | S4-5 |
| I-b-71 | cloquintocet-mexyl |
| I-b-71 | fenchlorazole-ethyl |
| I-b-71 | isoxadifen-ethyl |
| I-b-71 | mefenpyr-diethyl |
| I-b-71 | fenclorim |
| I-b-71 | cumyluron |
| I-b-71 | S4-1 |
| I-b-71 | S4-5 |
| I-b-72 | cloquintocet-mexyl |
| I-b-72 | fenchlorazole-ethyl |
| I-b-72 | isoxadifen-ethyl |
| I-b-72 | mefenpyr-diethyl |
| I-b-72 | fenclorim |
| I-b-72 | cumyluron |
| I-b-72 | S4-1 |
| I-b-72 | S4-5 |
| I-b-73 | cloquintocet-mexyl |

-continued

| Active compound of the formula | Safener |
|---|---|
| I-b-73 | fenchlorazole-ethyl |
| I-b-73 | isoxadifen-ethyl |
| I-b-73 | mefenpyr-diethyl |
| I-b-73 | fenclorim |
| I-b-73 | cumyluron |
| I-b-73 | S4-1 |
| I-b-73 | S4-5 |
| I-b-74 | cloquintocet-mexyl |
| I-b-74 | fenchlorazole-ethyl |
| I-b-74 | isoxadifen-ethyl |
| I-b-74 | mefenpyr-diethyl |
| I-b-74 | fenclorim |
| I-b-74 | cumyluron |
| I-b-74 | S4-1 |
| I-b-74 | S4-5 |
| I-b-75 | cloquintocet-mexyl |
| I-b-75 | fenchlorazole-ethyl |
| I-b-75 | isoxadifen-ethyl |
| I-b-75 | mefenpyr-diethyl |
| I-b-75 | fenclorim |
| I-b-75 | cumyluron |
| I-b-75 | S4-1 |
| I-b-75 | S4-5 |
| I-b-76 | cloquintocet-mexyl |
| I-b-76 | fenchlorazole-ethyl |
| I-b-76 | isoxadifen-ethyl |
| I-b-76 | mefenpyr-diethyl |
| I-b-76 | fenclorim |
| I-b-76 | cumyluron |
| I-b-76 | S4-1 |
| I-b-76 | S4-5 |
| I-b-77 | cloquintocet-mexyl |
| I-b-77 | fenchlorazole-ethyl |
| I-b-77 | isoxadifen-ethyl |
| I-b-77 | mefenpyr-diethyl |
| I-b-77 | fenclorim |
| I-b-77 | cumyluron |
| I-b-77 | S4-1 |
| I-b-77 | S4-5 |
| I-b-78 | cloquintocet-mexyl |
| I-b-78 | fenchlorazole-ethyl |
| I-b-78 | isoxadifen-ethyl |
| I-b-78 | mefenpyr-diethyl |
| I-b-78 | fenclorim |
| I-b-78 | cumyluron |
| I-b-78 | S4-1 |
| I-b-78 | S4-5 |
| I-b-79 | cloquintocet-mexyl |
| I-b-79 | fenchlorazole-ethyl |
| I-b-79 | isoxadifen-ethyl |
| I-b-79 | mefenpyr-diethyl |
| I-b-79 | fenclorim |
| I-b-79 | cumyluron |
| I-b-79 | S4-1 |
| I-b-79 | S4-5 |
| I-c-1 | cloquintocet-mexyl |
| I-c-1 | fenchlorazole-ethyl |
| I-c-1 | isoxadifen-ethyl |
| I-c-1 | mefenpyr-diethyl |
| I-c-1 | fenclorim |
| I-c-1 | cumyluron |
| I-c-1 | S4-1 |
| I-c-1 | S4-5 |
| I-c-2 | cloquintocet-mexyl |
| I-c-2 | fenchlorazole-ethyl |
| I-c-2 | isoxadifen-ethyl |
| I-c-2 | mefenpyr-diethyl |
| I-c-2 | fenclorim |
| I-c-2 | cumyluron |
| I-c-2 | S4-1 |
| I-c-2 | S4-5 |
| I-c-3 | cloquintocet-mexyl |
| I-c-3 | fenchlorazole-ethyl |
| I-c-3 | isoxadifen-ethyl |
| I-c-3 | mefenpyr-diethyl |
| I-c-3 | fenclorim |
| I-c-3 | cumyluron |

-continued

| Active compound of the formula | Safener |
|---|---|
| I-c-3 | S4-1 |
| I-c-3 | S4-5 |
| I-c-4 | cloquintocet-mexyl |
| I-c-4 | fenchlorazole-ethyl |
| I-c-4 | isoxadifen-ethyl |
| I-c-4 | mefenpyr-diethyl |
| I-c-4 | fenclorim |
| I-c-4 | cumyluron |
| I-c-4 | S4-1 |
| I-c-4 | S4-5 |
| I-c-5 | cloquintocet-mexyl |
| I-c-5 | fenchlorazole-ethyl |
| I-c-5 | isoxadifen-ethyl |
| I-c-5 | mefenpyr-diethyl |
| I-c-5 | fenclorim |
| I-c-5 | cumyluron |
| I-c-5 | S4-1 |
| I-c-5 | S4-5 |
| I-c-6 | cloquintocet-mexyl |
| I-c-6 | fenchlorazole-ethyl |
| I-c-6 | isoxadifen-ethyl |
| I-c-6 | mefenpyr-diethyl |
| I-c-6 | fenclorim |
| I-c-6 | cumyluron |
| I-c-6 | S4-1 |
| I-c-6 | S4-5 |
| I-c-7 | cloquintocet-mexyl |
| I-c-7 | fenchlorazole-ethyl |
| I-c-7 | isoxadifen-ethyl |
| I-c-7 | mefenpyr-diethyl |
| I-c-7 | fenclorim |
| I-c-7 | cumyluron |
| I-c-7 | S4-1 |
| I-c-7 | S4-5 |
| I-c-8 | cloquintocet-mexyl |
| I-c-8 | fenchlorazole-ethyl |
| I-c-8 | isoxadifen-ethyl |
| I-c-8 | mefenpyr-diethyl |
| I-c-8 | fenclorim |
| I-c-8 | cumyluron |
| I-c-8 | S4-1 |
| I-c-8 | S4-5 |
| I-c-9 | cloquintocet-mexyl |
| I-c-9 | fenchlorazole-ethyl |
| I-c-9 | isoxadifen-ethyl |
| I-c-9 | mefenpyr-diethyl |
| I-c-9 | fenclorim |
| I-c-9 | cumyluron |
| I-c-9 | S4-1 |
| I-c-9 | S4-5 |
| I-c-10 | cloquintocet-mexyl |
| I-c-10 | fenchlorazole-ethyl |
| I-c-10 | isoxadifen-ethyl |
| I-c-10 | mefenpyr-diethyl |
| I-c-10 | fenclorim |
| I-c-10 | cumyluron |
| I-c-10 | S4-1 |
| I-c-10 | S4-5 |
| I-c-11 | cloquintocet-mexyl |
| I-c-11 | fenchlorazole-ethyl |
| I-c-11 | isoxadifen-ethyl |
| I-c-11 | mefenpyr-diethyl |
| I-c-11 | fenclorim |
| I-c-11 | cumyluron |
| I-c-11 | S4-1 |
| I-c-11 | S4-5 |
| I-c-12 | cloquintocet-mexyl |
| I-c-12 | fenchlorazole-ethyl |
| I-c-12 | isoxadifen-ethyl |
| I-c-12 | mefenpyr-diethyl |
| I-c-12 | fenclorim |
| I-c-12 | cumyluron |
| I-c-12 | S4-1 |
| I-c-12 | S4-5 |
| I-c-13 | cloquintocet-mexyl |
| I-c-13 | fenchlorazole-ethyl |
| I-c-13 | isoxadifen-ethyl |

-continued

| Active compound of the formula | Safener |
|---|---|
| I-c-13 | mefenpyr-diethyl |
| I-c-13 | fenclorim |
| I-c-13 | cumyluron |
| I-c-13 | S4-1 |
| I-c-13 | S4-5 |
| I-c-14 | cloquintocet-mexyl |
| I-c-14 | fenchlorazole-ethyl |
| I-c-14 | isoxadifen-ethyl |
| I-c-14 | mefenpyr-diethyl |
| I-c-14 | fenclorim |
| I-c-14 | cumyluron |
| I-c-14 | S4-1 |
| I-c-14 | S4-5 |
| I-c-15 | cloquintocet-mexyl |
| I-c-15 | fenchlorazole-ethyl |
| I-c-15 | isoxadifen-ethyl |
| I-c-15 | mefenpyr-diethyl |
| I-c-15 | fenclorim |
| I-c-15 | cumyluron |
| I-c-15 | S4-1 |
| I-c-15 | S4-5 |
| I-c-16 | cloquintocet-mexyl |
| I-c-16 | fenchlorazole-ethyl |
| I-c-16 | isoxadifen-ethyl |
| I-c-16 | mefenpyr-diethyl |
| I-c-16 | fenclorim |
| I-c-16 | cumyluron |
| I-c-16 | S4-1 |
| I-c-16 | S4-5 |
| I-c-17 | cloquintocet-mexyl |
| I-c-17 | fenchlorazole-ethyl |
| I-c-17 | isoxadifen-ethyl |
| I-c-17 | mefenpyr-diethyl |
| I-c-17 | fenclorim |
| I-c-17 | cumyluron |
| I-c-17 | S4-1 |
| I-c-17 | S4-5 |
| I-c-18 | cloquintocet-mexyl |
| I-c-18 | fenchlorazole-ethyl |
| I-c-18 | isoxadifen-ethyl |
| I-c-18 | mefenpyr-diethyl |
| I-c-18 | fenclorim |
| I-c-18 | cumyluron |
| I-c-18 | S4-1 |
| I-c-18 | S4-5 |
| I-c-19 | cloquintocet-mexyl |
| I-c-19 | fenchlorazole-ethyl |
| I-c-19 | isoxadifen-ethyl |
| I-c-19 | mefenpyr-diethyl |
| I-c-19 | fenclorim |
| I-c-19 | cumyluron |
| I-c-19 | S4-1 |
| I-c-19 | S4-5 |
| I-c-20 | cloquintocet-mexyl |
| I-c-20 | fenchlorazole-ethyl |
| I-c-20 | isoxadifen-ethyl |
| I-c-20 | mefenpyr-diethyl |
| I-c-20 | fenclorim |
| I-c-20 | cumyluron |
| I-c-20 | S4-1 |
| I-c-20 | S4-5 |
| I-c-21 | cloquintocet-mexyl |
| I-c-21 | fenchlorazole-ethyl |
| I-c-21 | isoxadifen-ethyl |
| I-c-21 | mefenpyr-diethyl |
| I-c-21 | fenclorim |
| I-c-21 | cumyluron |
| I-c-21 | S4-1 |
| I-c-21 | S4-5 |
| I-c-22 | cloquintocet-mexyl |
| I-c-22 | fenchlorazole-ethyl |
| I-c-22 | isoxadifen-ethyl |
| I-c-22 | mefenpyr-diethyl |
| I-c-22 | fenclorim |
| I-c-22 | cumyluron |
| I-c-22 | S4-1 |
| I-c-22 | S4-5 |

-continued

| Active compound of the formula | Safener |
|---|---|
| I-c-23 | cloquintocet-mexyl |
| I-c-23 | fenchlorazole-ethyl |
| I-c-23 | isoxadifen-ethyl |
| I-c-23 | mefenpyr-diethyl |
| I-c-23 | fenclorim |
| I-c-23 | cumyluron |
| I-c-23 | S4-1 |
| I-c-23 | S4-5 |
| I-c-24 | cloquintocet-mexyl |
| I-c-24 | fenchlorazole-ethyl |
| I-c-24 | isoxadifen-ethyl |
| I-c-24 | mefenpyr-diethyl |
| I-c-24 | fenclorim |
| I-c-24 | cumyluron |
| I-c-24 | S4-1 |
| I-c-24 | S4-5 |
| I-c-25 | cloquintocet-mexyl |
| I-c-25 | fenchlorazole-ethyl |
| I-c-25 | isoxadifen-ethyl |
| I-c-25 | mefenpyr-diethyl |
| I-c-25 | fenclorim |
| I-c-25 | cumyluron |
| I-c-25 | S4-1 |
| I-c-25 | S4-5 |
| I-c-26 | cloquintocet-mexyl |
| I-c-26 | fenchlorazole-ethyl |
| I-c-26 | isoxadifen-ethyl |
| I-c-26 | mefenpyr-diethyl |
| I-c-26 | fenclorim |
| I-c-26 | cumyluron |
| I-c-26 | S4-1 |
| I-c-26 | S4-5 |
| I-c-27 | cloquintocet-mexyl |
| I-c-27 | fenchlorazole-ethyl |
| I-c-27 | isoxadifen-ethyl |
| I-c-27 | mefenpyr-diethyl |
| I-c-27 | fenclorim |
| I-c-27 | cumyluron |
| I-c-27 | S4-1 |
| I-c-27 | S4-5 |
| I-c-28 | cloquintocet-mexyl |
| I-c-28 | fenchlorazole-ethyl |
| I-c-28 | isoxadifen-ethyl |
| I-c-28 | mefenpyr-diethyl |
| I-c-28 | fenclorim |
| I-c-28 | cumyluron |
| I-c-28 | S4-1 |
| I-c-28 | S4-5 |
| I-c-29 | cloquintocet-mexyl |
| I-c-29 | fenchlorazole-ethyl |
| I-c-29 | isoxadifen-ethyl |
| I-c-29 | mefenpyr-diethyl |
| I-c-29 | fenclorim |
| I-c-29 | cumyluron |
| I-c-29 | S4-1 |
| I-c-29 | S4-5 |
| I-c-30 | cloquintocet-mexyl |
| I-c-30 | fenchlorazole-ethyl |
| I-c-30 | isoxadifen-ethyl |
| I-c-30 | mefenpyr-diethyl |
| I-c-30 | fenclorim |
| I-c-30 | cumyluron |
| I-c-30 | S4-1 |
| I-c-30 | S4-5 |
| I-c-31 | cloquintocet-mexyl |
| I-c-31 | fenchlorazole-ethyl |
| I-c-31 | isoxadifen-ethyl |
| I-c-31 | mefenpyr-diethyl |
| I-c-31 | fenclorim |
| I-c-31 | cumyluron |
| I-c-31 | S4-1 |
| I-c-31 | S4-5 |
| I-c-32 | cloquintocet-mexyl |
| I-c-32 | fenchlorazole-ethyl |
| I-c-32 | isoxadifen-ethyl |
| I-c-32 | mefenpyr-diethyl |
| I-c-32 | fenclorim |

-continued

| Active compound of the formula | Safener |
|---|---|
| I-c-32 | cumyluron |
| I-c-32 | S4-1 |
| I-c-32 | S4-5 |
| I-c-33 | cloquintocet-mexyl |
| I-c-33 | fenchlorazole-ethyl |
| I-c-33 | isoxadifen-ethyl |
| I-c-33 | mefenpyr-diethyl |
| I-c-33 | fenclorim |
| I-c-33 | cumyluron |
| I-c-33 | S4-1 |
| I-c-33 | S4-5 |
| I-c-34 | cloquintocet-mexyl |
| I-c-34 | fenchlorazole-ethyl |
| I-c-34 | isoxadifen-ethyl |
| I-c-34 | mefenpyr-diethyl |
| I-c-34 | fenclorim |
| I-c-34 | cumyluron |
| I-c-34 | S4-1 |
| I-c-34 | S4-5 |
| I-c-35 | cloquintocet-mexyl |
| I-c-35 | fenchlorazole-ethyl |
| I-c-35 | isoxadifen-ethyl |
| I-c-35 | mefenpyr-diethyl |
| I-c-35 | fenclorim |
| I-c-35 | cumyluron |
| I-c-35 | S4-1 |
| I-c-35 | S4-5 |
| I-c-36 | cloquintocet-mexyl |
| I-c-36 | fenchlorazole-ethyl |
| I-c-36 | isoxadifen-ethyl |
| I-c-36 | mefenpyr-diethyl |
| I-c-36 | fenclorim |
| I-c-36 | cumyluron |
| I-c-36 | S4-1 |
| I-c-36 | S4-5 |
| I-c-37 | cloquintocet-mexyl |
| I-c-37 | fenchlorazole-ethyl |
| I-c-37 | isoxadifen-ethyl |
| I-c-37 | mefenpyr-diethyl |
| I-c-37 | fenclorim |
| I-c-37 | cumyluron |
| I-c-37 | S4-1 |
| I-c-37 | S4-5 |
| I-c-38 | cloquintocet-mexyl |
| I-c-38 | fenchlorazole-ethyl |
| I-c-38 | isoxadifen-ethyl |
| I-c-38 | mefenpyr-diethyl |
| I-c-38 | fenclorim |
| I-c-38 | cumyluron |
| I-c-38 | S4-1 |
| I-c-38 | S4-5 |
| I-c-39 | cloquintocet-mexyl |
| I-c-39 | fenchlorazole-ethyl |
| I-c-39 | isoxadifen-ethyl |
| I-c-39 | mefenpyr-diethyl |
| I-c-39 | fenclorim |
| I-c-39 | cumyluron |
| I-c-39 | S4-1 |
| I-c-39 | S4-5 |
| I-c-40 | cloquintocet-mexyl |
| I-c-40 | fenchlorazole-ethyl |
| I-c-40 | isoxadifen-ethyl |
| I-c-40 | mefenpyr-diethyl |
| I-c-40 | fenclorim |
| I-c-40 | cumyluron |
| I-c-40 | S4-1 |
| I-c-40 | S4-5 |
| I-c-41 | cloquintocet-mexyl |
| I-c-41 | fenchlorazole-ethyl |
| I-c-41 | isoxadifen-ethyl |
| I-c-41 | mefenpyr-diethyl |
| I-c-41 | fenclorim |
| I-c-41 | cumyluron |
| I-c-41 | S4-1 |
| I-c-41 | S4-5 |
| I-c-42 | cloquintocet-mexyl |
| I-c-42 | fenchlorazole-ethyl |

-continued

| Active compound of the formula | Safener |
|---|---|
| I-c-42 | isoxadifen-ethyl |
| I-c-42 | mefenpyr-diethyl |
| I-c-42 | fenclorim |
| I-c-42 | cumyluron |
| I-c-42 | S4-1 |
| I-c-42 | S4-5 |
| I-c-43 | cloquintocet-mexyl |
| I-c-43 | fenchlorazole-ethyl |
| I-c-43 | isoxadifen-ethyl |
| I-c-43 | mefenpyr-diethyl |
| I-c-43 | fenclorim |
| I-c-43 | cumyluron |
| I-c-43 | S4-1 |
| I-c-43 | S4-5 |
| I-c-44 | cloquintocet-mexyl |
| I-c-44 | fenchlorazole-ethyl |
| I-c-44 | isoxadifen-ethyl |
| I-c-44 | mefenpyr-diethyl |
| I-c-44 | fenclorim |
| I-c-44 | cumyluron |
| I-c-44 | S4-1 |
| I-c-44 | S4-5 |
| I-c-45 | cloquintocet-mexyl |
| I-c-45 | fenchlorazole-ethyl |
| I-c-45 | isoxadifen-ethyl |
| I-c-45 | mefenpyr-diethyl |
| I-c-45 | fenclorim |
| I-c-45 | cumyluron |
| I-c-45 | S4-1 |
| I-c-45 | S4-5 |
| I-c-46 | cloquintocet-mexyl |
| I-c-46 | fenchlorazole-ethyl |
| I-c-46 | isoxadifen-ethyl |
| I-c-46 | mefenpyr-diethyl |
| I-c-46 | fenclorim |
| I-c-46 | cumyluron |
| I-c-46 | S4-1 |
| I-c-46 | S4-5 |
| I-c-47 | cloquintocet-mexyl |
| I-c-47 | fenchlorazole-ethyl |
| I-c-47 | isoxadifen-ethyl |
| I-c-47 | mefenpyr-diethyl |
| I-c-47 | fenclorim |
| I-c-47 | cumyluron |
| I-c-47 | S4-1 |
| I-c-47 | S4-5 |
| I-c-48 | cloquintocet-mexyl |
| I-c-48 | fenchlorazole-ethyl |
| I-c-48 | isoxadifen-ethyl |
| I-c-48 | mefenpyr-diethyl |
| I-c-48 | fenclorim |
| I-c-48 | cumyluron |
| I-c-48 | S4-1 |
| I-c-48 | S4-5 |
| I-c-49 | cloquintocet-mexyl |
| I-c-49 | fenchlorazole-ethyl |
| I-c-49 | isoxadifen-ethyl |
| I-c-49 | mefenpyr-diethyl |
| I-c-49 | fenclorim |
| I-c-49 | cumyluron |
| I-c-49 | S4-1 |
| I-c-49 | S4-5 |
| I-c-50 | cloquintocet-mexyl |
| I-c-50 | fenchlorazole-ethyl |
| I-c-50 | isoxadifen-ethyl |
| I-c-50 | mefenpyr-diethyl |
| I-c-50 | fenclorim |
| I-c-50 | cumyluron |
| I-c-50 | S4-1 |
| I-c-50 | S4-5 |
| I-c-51 | cloquintocet-mexyl |
| I-c-51 | fenchlorazole-ethyl |
| I-c-51 | isoxadifen-ethyl |
| I-c-51 | mefenpyr-diethyl |
| I-c-51 | fenclorim |
| I-c-51 | cumyluron |
| I-c-51 | S4-1 |

| Active compound of the formula | Safener |
|---|---|
| I-c-51 | S4-5 |
| I-c-52 | cloquintocet-mexyl |
| I-c-52 | fenchlorazole-ethyl |
| I-c-52 | isoxadifen-ethyl |
| I-c-52 | mefenpyr-diethyl |
| I-c-52 | fenclorim |
| I-c-52 | cumyluron |
| I-c-52 | S4-1 |
| I-c-52 | S4-5 |
| I-c-53 | cloquintocet-mexyl |
| I-c-53 | fenchlorazole-ethyl |
| I-c-53 | isoxadifen-ethyl |
| I-c-53 | mefenpyr-diethyl |
| I-c-53 | fenclorim |
| I-c-53 | cumyluron |
| I-c-53 | S4-1 |
| I-c-53 | S4-5 |
| I-c-54 | cloquintocet-mexyl |
| I-c-54 | fenchlorazole-ethyl |
| I-c-54 | isoxadifen-ethyl |
| I-c-54 | mefenpyr-diethyl |
| I-c-54 | fenclorim |
| I-c-54 | cumyluron |
| I-c-54 | S4-1 |
| I-c-54 | S4-5 |
| I-c-55 | cloquintocet-mexyl |
| I-c-55 | fenchlorazole-ethyl |
| I-c-55 | isoxadifen-ethyl |
| I-c-55 | mefenpyr-diethyl |
| I-c-55 | fenclorim |
| I-c-55 | cumyluron |
| I-c-55 | S4-1 |
| I-c-55 | S4-5 |
| I-c-56 | cloquintocet-mexyl |
| I-c-56 | fenchlorazole-ethyl |
| I-c-56 | isoxadifen-ethyl |
| I-c-56 | mefenpyr-diethyl |
| I-c-56 | fenclorim |
| I-c-56 | cumyluron |
| I-c-56 | S4-1 |
| I-c-56 | S4-5 |
| I-c-57 | cloquintocet-mexyl |
| I-c-57 | fenchlorazole-ethyl |
| I-c-57 | isoxadifen-ethyl |
| I-c-57 | mefenpyr-diethyl |
| I-c-57 | fenclorim |
| I-c-57 | cumyluron |
| I-c-57 | S4-1 |
| I-c-57 | S4-5 |
| I-c-58 | cloquintocet-mexyl |
| I-c-58 | fenchlorazole-ethyl |
| I-c-58 | isoxadifen-ethyl |
| I-c-58 | mefenpyr-diethyl |
| I-c-58 | fenclorim |
| I-c-58 | cumyluron |
| I-c-58 | S4-1 |
| I-c-58 | S4-5 |
| I-c-59 | cloquintocet-mexyl |
| I-c-59 | fenchlorazole-ethyl |
| I-c-59 | isoxadifen-ethyl |
| I-c-59 | mefenpyr-diethyl |
| I-c-59 | fenclorim |
| I-c-59 | cumyluron |
| I-c-59 | S4-1 |
| I-c-59 | S4-5 |
| I-c-60 | cloquintocet-mexyl |
| I-c-60 | fenchlorazole-ethyl |
| I-c-60 | isoxadifen-ethyl |
| I-c-60 | mefenpyr-diethyl |
| I-c-60 | fenclorim |
| I-c-60 | cumyluron |
| I-c-60 | S4-1 |
| I-c-60 | S4-5 |
| I-c-61 | cloquintocet-mexyl |
| I-c-61 | fenchlorazole-ethyl |
| I-c-61 | isoxadifen-ethyl |
| I-c-61 | mefenpyr-diethyl |
| I-c-61 | fenclorim |
| I-c-61 | cumyluron |
| I-c-61 | S4-1 |
| I-c-61 | S4-5 |
| I-c-62 | cloquintocet-mexyl |
| I-c-62 | fenchlorazole-ethyl |
| I-c-62 | isoxadifen-ethyl |
| I-c-62 | mefenpyr-diethyl |
| I-c-62 | fenclorim |
| I-c-62 | cumyluron |
| I-c-62 | S4-1 |
| I-c-62 | S4-5 |
| I-c-63 | cloquintocet-mexyl |
| I-c-63 | fenchlorazole-ethyl |
| I-c-63 | isoxadifen-ethyl |
| I-c-63 | mefenpyr-diethyl |
| I-c-63 | fenclorim |
| I-c-63 | cumyluron |
| I-c-63 | S4-1 |
| I-c-63 | S4-5 |
| I-c-64 | cloquintocet-mexyl |
| I-c-64 | fenchlorazole-ethyl |
| I-c-64 | isoxadifen-ethyl |
| I-c-64 | mefenpyr-diethyl |
| I-c-64 | fenclorim |
| I-c-64 | cumyluron |
| I-c-64 | S4-1 |
| I-c-64 | S4-5 |
| I-c-65 | cloquintocet-mexyl |
| I-c-65 | fenchlorazole-ethyl |
| I-c-65 | isoxadifen-ethyl |
| I-c-65 | mefenpyr-diethyl |
| I-c-65 | fenclorim |
| I-c-65 | cumyluron |
| I-c-65 | S4-1 |
| I-c-65 | S4-5 |
| I-c-66 | cloquintocet-mexyl |
| I-c-66 | fenchlorazole-ethyl |
| I-c-66 | isoxadifen-ethyl |
| I-c-66 | mefenpyr-diethyl |
| I-c-66 | fenclorim |
| I-c-66 | cumyluron |
| I-c-66 | S4-1 |
| I-c-66 | S4-5 |
| I-c-67 | cloquintocet-mexyl |
| I-c-67 | fenchlorazole-ethyl |
| I-c-67 | isoxadifen-ethyl |
| I-c-67 | mefenpyr-diethyl |
| I-c-67 | fenclorim |
| I-c-67 | cumyluron |
| I-c-67 | S4-1 |
| I-c-67 | S4-5 |
| I-c-68 | cloquintocet-mexyl |
| I-c-68 | fenchlorazole-ethyl |
| I-c-68 | isoxadifen-ethyl |
| I-c-68 | mefenpyr-diethyl |
| I-c-68 | fenclorim |
| I-c-68 | cumyluron |
| I-c-68 | S4-1 |
| I-c-68 | S4-5 |
| I-c-69 | cloquintocet-mexyl |
| I-c-69 | fenchlorazole-ethyl |
| I-c-69 | isoxadifen-ethyl |
| I-c-69 | mefenpyr-diethyl |
| I-c-69 | fenclorim |
| I-c-69 | cumyluron |
| I-c-69 | S4-1 |
| I-c-69 | S4-5 |
| I-c-70 | cloquintocet-mexyl |
| I-c-70 | fenchlorazole-ethyl |
| I-c-70 | isoxadifen-ethyl |
| I-c-70 | mefenpyr-diethyl |
| I-c-70 | fenclorim |
| I-c-70 | cumyluron |
| I-c-70 | S4-1 |
| I-c-70 | S4-5 |
| I-c-71 | cloquintocet-mexyl |

-continued

| Active compound of the formula | Safener |
|---|---|
| I-c-71 | fenchlorazole-ethyl |
| I-c-71 | isoxadifen-ethyl |
| I-c-71 | mefenpyr-diethyl |
| I-c-71 | fenclorim |
| I-c-71 | cumyluron |
| I-c-71 | S4-1 |
| I-c-71 | S4-5 |
| I-c-72 | cloquintocet-mexyl |
| I-c-72 | fenchlorazole-ethyl |
| I-c-72 | isoxadifen-ethyl |
| I-c-72 | mefenpyr-diethyl |
| I-c-72 | fenclorim |
| I-c-72 | cumyluron |
| I-c-72 | S4-1 |
| I-c-72 | S4-5 |
| I-c-73 | cloquintocet-mexyl |
| I-c-73 | fenchlorazole-ethyl |
| I-c-73 | isoxadifen-ethyl |
| I-c-73 | mefenpyr-diethyl |
| I-c-73 | fenclorim |
| I-c-73 | cumyluron |
| I-c-73 | S4-1 |
| I-c-73 | S4-5 |
| I-c-74 | cloquintocet-mexyl |
| I-c-74 | fenchlorazole-ethyl |
| I-c-74 | isoxadifen-ethyl |
| I-c-74 | mefenpyr-diethyl |
| I-c-74 | fenclorim |
| I-c-74 | cumyluron |
| I-c-74 | S4-1 |
| I-c-74 | S4-5 |
| I-c-75 | cloquintocet-mexyl |
| I-c-75 | fenchlorazole-ethyl |
| I-c-75 | isoxadifen-ethyl |
| I-c-75 | mefenpyr-diethyl |
| I-c-75 | fenclorim |
| I-c-75 | cumyluron |
| I-c-75 | S4-1 |
| I-c-75 | S4-5 |
| I-c-76 | cloquintocet-mexyl |
| I-c-76 | fenchlorazole-ethyl |
| I-c-76 | isoxadifen-ethyl |
| I-c-76 | mefenpyr-diethyl |
| I-c-76 | fenclorim |
| I-c-76 | cumyluron |
| I-c-76 | S4-1 |
| I-c-76 | S4-5 |
| I-c-77 | cloquintocet-mexyl |
| I-c-77 | fenchlorazole-ethyl |
| I-c-77 | isoxadifen-ethyl |
| I-c-77 | mefenpyr-diethyl |
| I-c-77 | fenclorim |
| I-c-77 | cumyluron |
| I-c-77 | S4-1 |
| I-c-77 | S4-5 |
| I-c-78 | cloquintocet-mexyl |
| I-c-78 | fenchlorazole-ethyl |
| I-c-78 | isoxadifen-ethyl |
| I-c-78 | mefenpyr-diethyl |
| I-c-78 | fenclorim |
| I-c-78 | cumyluron |
| I-c-78 | S4-1 |
| I-c-78 | S4-5 |
| I-c-79 | cloquintocet-mexyl |
| I-c-79 | fenchlorazole-ethyl |
| I-c-79 | isoxadifen-ethyl |
| I-c-79 | mefenpyr-diethyl |
| I-c-79 | fenclorim |
| I-c-79 | cumyluron |
| I-c-79 | S4-1 |
| I-c-79 | S4-5 |
| I-c-80 | cloquintocet-mexyl |
| I-c-80 | fenchlorazole-ethyl |
| I-c-80 | isoxadifen-ethyl |
| I-c-80 | mefenpyr-diethyl |
| I-c-80 | fenclorim |
| I-c-80 | cumyluron |

-continued

| Active compound of the formula | Safener |
|---|---|
| I-c-80 | S4-1 |
| I-c-80 | S4-5 |
| I-c-81 | cloquintocet-mexyl |
| I-c-81 | fenchlorazole-ethyl |
| I-c-81 | isoxadifen-ethyl |
| I-c-81 | mefenpyr-diethyl |
| I-c-81 | fenclorim |
| I-c-81 | cumyluron |
| I-c-81 | S4-1 |
| I-c-81 | S4-5 |
| I-c-82 | cloquintocet-mexyl |
| I-c-82 | fenchlorazole-ethyl |
| I-c-82 | isoxadifen-ethyl |
| I-c-82 | mefenpyr-diethyl |
| I-c-82 | fenclorim |
| I-c-82 | cumyluron |
| I-c-82 | S4-1 |
| I-c-82 | S4-5 |
| I-c-83 | cloquintocet-mexyl |
| I-c-83 | fenchlorazole-ethyl |
| I-c-83 | isoxadifen-ethyl |
| I-c-83 | mefenpyr-diethyl |
| I-c-83 | fenclorim |
| I-c-83 | cumyluron |
| I-c-83 | S4-1 |
| I-c-83 | S4-5 |
| I-c-84 | cloquintocet-mexyl |
| I-c-84 | fenchlorazole-ethyl |
| I-c-84 | isoxadifen-ethyl |
| I-c-84 | mefenpyr-diethyl |
| I-c-84 | fenclorim |
| I-c-84 | cumyluron |
| I-c-84 | S4-1 |
| I-c-84 | S4-5 |
| I-c-85 | cloquintocet-mexyl |
| I-c-85 | fenchlorazole-ethyl |
| I-c-85 | isoxadifen-ethyl |
| I-c-85 | mefenpyr-diethyl |
| I-c-85 | fenclorim |
| I-c-85 | cumyluron |
| I-c-85 | S4-1 |
| I-c-85 | S4-5 |
| I-c-86 | cloquintocet-mexyl |
| I-c-86 | fenchlorazole-ethyl |
| I-c-86 | isoxadifen-ethyl |
| I-c-86 | mefenpyr-diethyl |
| I-c-86 | fenclorim |
| I-c-86 | cumyluron |
| I-c-86 | S4-1 |
| I-c-86 | S4-5 |
| I-c-87 | cloquintocet-mexyl |
| I-c-87 | fenchlorazole-ethyl |
| I-c-87 | isoxadifen-ethyl |
| I-c-87 | mefenpyr-diethyl |
| I-c-87 | fenclorim |
| I-c-87 | cumyluron |
| I-c-87 | S4-1 |
| I-c-87 | S4-5 |
| I-c-88 | cloquintocet-mexyl |
| I-c-88 | fenchlorazole-ethyl |
| I-c-88 | isoxadifen-ethyl |
| I-c-88 | mefenpyr-diethyl |
| I-c-88 | fenclorim |
| I-c-88 | cumyluron |
| I-c-88 | S4-1 |
| I-c-88 | S4-5 |
| I-c-89 | cloquintocet-mexyl |
| I-c-89 | fenchlorazole-ethyl |
| I-c-89 | isoxadifen-ethyl |
| I-c-89 | mefenpyr-diethyl |
| I-c-89 | fenclorim |
| I-c-89 | cumyluron |
| I-c-89 | S4-1 |
| I-c-89 | S4-5 |
| I-d-1 | cloquintocet-mexyl |
| I-d-1 | fenchlorazole-ethyl |
| I-d-1 | isoxadifen-ethyl |

| Active compound of the formula | Safener |
|---|---|
| I-d-1 | mefenpyr-diethyl |
| I-d-1 | fenclorim |
| I-d-1 | cumyluron |
| I-d-1 | S4-1 |
| I-d-1 | S4-5 |
| I-d-2 | cloquintocet-mexyl |
| I-d-2 | fenchlorazole-ethyl |
| I-d-2 | isoxadifen-ethyl |
| I-d-2 | mefenpyr-diethyl |
| I-d-2 | fenclorim |
| I-d-2 | cumyluron |
| I-d-2 | S4-1 |
| I-d-2 | S4-5 |
| I-d-3 | cloquintocet-mexyl |
| I-d-3 | fenchlorazole-ethyl |
| I-d-3 | isoxadifen-ethyl |
| I-d-3 | mefenpyr-diethyl |
| I-d-3 | fenclorim |
| I-d-3 | cumyluron |
| I-d-3 | S4-1 |
| I-d-3 | S4-5 |
| I-d-4 | cloquintocet-mexyl |
| I-d-4 | fenchlorazole-ethyl |
| I-d-4 | isoxadifen-ethyl |
| I-d-4 | mefenpyr-diethyl |
| I-d-4 | fenclorim |
| I-d-4 | cumyluron |
| I-d-4 | S4-1 |
| I-d-4 | S4-5 |
| I-d-5 | cloquintocet-mexyl |
| I-d-5 | fenchlorazole-ethyl |
| I-d-5 | isoxadifen-ethyl |
| I-d-5 | mefenpyr-diethyl |
| I-d-5 | fenclorim |
| I-d-5 | cumyluron |
| I-d-5 | S4-1 |
| I-d-5 | S4-5 |
| I-d-6 | cloquintocet-mexyl |
| I-d-6 | fenchlorazole-ethyl |
| I-d-6 | isoxadifen-ethyl |
| I-d-6 | mefenpyr-diethyl |
| I-d-6 | fenclorim |
| I-d-6 | cumyluron |
| I-d-6 | S4-1 |
| I-d-6 | S4-5 |
| I-d-7 | cloquintocet-mexyl |
| I-d-7 | fenchlorazole-ethyl |
| I-d-7 | isoxadifen-ethyl |
| I-d-7 | mefenpyr-diethyl |
| I-d-7 | fenclorim |
| I-d-7 | cumyluron |
| I-d-7 | S4-1 |
| I-d-7 | S4-5 |
| I-d-8 | cloquintocet-mexyl |
| I-d-8 | fenchlorazole-ethyl |
| I-d-8 | isoxadifen-ethyl |
| I-d-8 | mefenpyr-diethyl |
| I-d-8 | fenclorim |
| I-d-8 | cumyluron |
| I-d-8 | S4-1 |
| I-d-8 | S4-5 |
| I-d-9 | cloquintocet-mexyl |
| I-d-9 | fenchlorazole-ethyl |
| I-d-9 | isoxadifen-ethyl |
| I-d-9 | mefenpyr-diethyl |
| I-d-9 | fenclorim |
| I-d-9 | cumyluron |
| I-d-9 | S4-1 |
| I-d-9 | S4-5 |
| I-d-10 | cloquintocet-mexyl |
| I-d-10 | fenchlorazole-ethyl |
| I-d-10 | isoxadifen-ethyl |
| I-d-10 | mefenpyr-diethyl |
| I-d-10 | fenclorim |
| I-d-10 | cumyluron |
| I-d-10 | S4-1 |
| I-d-10 | S4-5 |
| I-d-11 | cloquintocet-mexyl |
| I-d-11 | fenchlorazole-ethyl |
| I-d-11 | isoxadifen-ethyl |
| I-d-11 | mefenpyr-diethyl |
| I-d-11 | fenclorim |
| I-d-11 | cumyluron |
| I-d-11 | S4-1 |
| I-d-11 | S4-5 |
| I-d-12 | cloquintocet-mexyl |
| I-d-12 | fenchlorazole-ethyl |
| I-d-12 | isoxadifen-ethyl |
| I-d-12 | mefenpyr-diethyl |
| I-d-12 | fenclorim |
| I-d-12 | cumyluron |
| I-d-12 | S4-1 |
| I-d-12 | S4-5 |
| I-d-13 | cloquintocet-mexyl |
| I-d-13 | fenchlorazole-ethyl |
| I-d-13 | isoxadifen-ethyl |
| I-d-13 | mefenpyr-diethyl |
| I-d-13 | fenclorim |
| I-d-13 | cumyluron |
| I-d-13 | S4-1 |
| I-d-13 | S4-5 |
| I-d-14 | cloquintocet-mexyl |
| I-d-14 | fenchlorazole-ethyl |
| I-d-14 | isoxadifen-ethyl |
| I-d-14 | mefenpyr-diethyl |
| I-d-14 | fenclorim |
| I-d-14 | cumyluron |
| I-d-14 | S4-1 |
| I-d-14 | S4-5 |
| I-d-15 | cloquintocet-mexyl |
| I-d-15 | fenchlorazole-ethyl |
| I-d-15 | isoxadifen-ethyl |
| I-d-15 | mefenpyr-diethyl |
| I-d-15 | fenclorim |
| I-d-15 | cumyluron |
| I-d-15 | S4-1 |
| I-d-15 | S4-5 |
| I-f-1 | cloquintocet-mexyl |
| I-f-1 | fenchlorazole-ethyl |
| I-f-1 | isoxadifen-ethyl |
| I-f-1 | mefenpyr-diethyl |
| I-f-1 | fenclorim |
| I-f-1 | cumyluron |
| I-f-1 | S4-1 |
| I-f-1 | S4-5 |
| I-f-2 | cloquintocet-mexyl |
| I-f-2 | fenchlorazole-ethyl |
| I-f-2 | isoxadifen-ethyl |
| I-f-2 | mefenpyr-diethyl |
| I-f-2 | fenclorim |
| I-f-2 | cumyluron |
| I-f-2 | S4-1 |
| I-f-2 | S4-5 |
| I-f-3 | cloquintocet-mexyl |
| I-f-3 | fenchlorazole-ethyl |
| I-f-3 | isoxadifen-ethyl |
| I-f-3 | mefenpyr-diethyl |
| I-f-3 | fenclorim |
| I-f-3 | cumyluron |
| I-f-3 | S4-1 |
| I-f-3 | S4-5 |
| I-f-4 | cloquintocet-mexyl |
| I-f-4 | fenchlorazole-ethyl |
| I-f-4 | isoxadifen-ethyl |
| I-f-4 | mefenpyr-diethyl |
| I-f-4 | fenclorim |
| I-f-4 | cumyluron |
| I-f-4 | S4-1 |
| I-f-4 | S4-5 |
| I-f-5 | cloquintocet-mexyl |
| I-f-5 | fenchlorazole-ethyl |
| I-f-5 | isoxadifen-ethyl |
| I-f-5 | mefenpyr-diethyl |
| I-f-5 | fenclorim |

| Active compound of the formula | Safener |
|---|---|
| I-f-5 | cumyluron |
| I-f-5 | S4-1 |
| I-f-5 | S4-5 |
| I-f-6 | cloquintocet-mexyl |
| I-f-6 | fenchlorazole-ethyl |
| I-f-6 | isoxadifen-ethyl |
| I-f-6 | mefenpyr-diethyl |
| I-f-6 | fenclorim |
| I-f-6 | cumyluron |
| I-f-6 | S4-1 |
| I-f-6 | S4-5 |
| I-f-7 | cloquintocet-mexyl |
| I-f-7 | fenchlorazole-ethyl |
| I-f-7 | isoxadifen-ethyl |
| I-f-7 | mefenpyr-diethyl |
| I-f-7 | fenclorim |
| I-f-7 | cumyluron |
| I-f-7 | S4-1 |
| I-f-7 | S4-5 |
| I-f-8 | cloquintocet-mexyl |
| I-f-8 | fenchlorazole-ethyl |
| I-f-8 | isoxadifen-ethyl |
| I-f-8 | mefenpyr-diethyl |
| I-f-8 | fenclorim |
| I-f-8 | cumyluron |
| I-f-8 | S4-1 |
| I-f-8 | S4-5 |
| I-f-9 | cloquintocet-mexyl |
| I-f-9 | fenchlorazole-ethyl |
| I-f-9 | isoxadifen-ethyl |
| I-f-9 | mefenpyr-diethyl |
| I-f-9 | fenclorim |
| I-f-9 | cumyluron |
| I-f-9 | S4-1 |
| I-f-9 | S4-5 |
| I-f-10 | cloquintocet-mexyl |
| I-f-10 | fenchlorazole-ethyl |
| I-f-10 | isoxadifen-ethyl |
| I-f-10 | mefenpyr-diethyl |
| I-f-10 | fenclorim |
| I-f-10 | cumyluron |
| I-f-10 | S4-1 |
| I-f-10 | S4-5 |
| I-f-11 | cloquintocet-mexyl |
| I-f-11 | fenchlorazole-ethyl |
| I-f-11 | isoxadifen-ethyl |
| I-f-11 | mefenpyr-diethyl |
| I-f-11 | fenclorim |
| I-f-11 | cumyluron |
| I-f-11 | S4-1 |
| I-f-11 | S4-5 |
| I-f-12 | cloquintocet-mexyl |
| I-f-12 | fenchlorazole-ethyl |
| I-f-12 | isoxadifen-ethyl |
| I-f-12 | mefenpyr-diethyl |
| I-f-12 | fenclorim |
| I-f-12 | cumyluron |
| I-f-12 | S4-1 |
| I-f-12 | S4-5 |
| I-f-13 | cloquintocet-mexyl |
| I-f-13 | fenchlorazole-ethyl |
| I-f-13 | isoxadifen-ethyl |
| I-f-13 | mefenpyr-diethyl |
| I-f-13 | fenclorim |
| I-f-13 | cumyluron |
| I-f-13 | S4-1 |
| I-f-13 | S4-5 |
| I-f-14 | cloquintocet-mexyl |
| I-f-14 | fenchlorazole-ethyl |
| I-f-14 | isoxadifen-ethyl |
| I-f-14 | mefenpyr-diethyl |
| I-f-14 | fenclorim |
| I-f-14 | cumyluron |
| I-f-14 | S4-1 |
| I-f-14 | S4-5 |
| I-f-15 | cloquintocet-mexyl |
| I-f-15 | fenchlorazole-ethyl |
| I-f-15 | isoxadifen-ethyl |
| I-f-15 | mefenpyr-diethyl |
| I-f-15 | fenclorim |
| I-f-15 | cumyluron |
| I-f-15 | S4-1 |
| I-f-15 | S4-5 |
| I-f-16 | cloquintocet-mexyl |
| I-f-16 | fenchlorazole-ethyl |
| I-f-16 | isoxadifen-ethyl |
| I-f-16 | mefenpyr-diethyl |
| I-f-16 | fenclorim |
| I-f-16 | cumyluron |
| I-f-16 | S4-1 |
| I-f-16 | S4-5 |
| I-f-17 | cloquintocet-mexyl |
| I-f-17 | fenchlorazole-ethyl |
| I-f-17 | isoxadifen-ethyl |
| I-f-17 | mefenpyr-diethyl |
| I-f-17 | fenclorim |
| I-f-17 | cumyluron |
| I-f-17 | S4-1 |
| I-f-17 | S4-5 |
| I-f-18 | cloquintocet-mexyl |
| I-f-18 | fenchlorazole-ethyl |
| I-f-18 | isoxadifen-ethyl |
| I-f-18 | mefenpyr-diethyl |
| I-f-18 | fenclorim |
| I-f-18 | cumyluron |
| I-f-18 | S4-1 |
| I-f-18 | S4-5 |
| I-f-19 | cloquintocet-mexyl |
| I-f-19 | fenchlorazole-ethyl |
| I-f-19 | isoxadifen-ethyl |
| I-f-19 | mefenpyr-diethyl |
| I-f-19 | fenclorim |
| I-f-19 | cumyluron |
| I-f-19 | S4-1 |
| I-f-19 | S4-5 |
| I-f-20 | cloquintocet-mexyl |
| I-f-20 | fenchlorazole-ethyl |
| I-f-20 | isoxadifen-ethyl |
| I-f-20 | mefenpyr-diethyl |
| I-f-20 | fenclorim |
| I-f-20 | cumyluron |
| I-f-20 | S4-1 |
| I-f-20 | S4-5 |
| I-f-21 | cloquintocet-mexyl |
| I-f-21 | fenchlorazole-ethyl |
| I-f-21 | isoxadifen-ethyl |
| I-f-21 | mefenpyr-diethyl |
| I-f-21 | fenclorim |
| I-f-21 | cumyluron |
| I-f-21 | S4-1 |
| I-f-21 | S4-5 |
| I-f-22 | cloquintocet-mexyl |
| I-f-22 | fenchlorazole-ethyl |
| I-f-22 | isoxadifen-ethyl |
| I-f-22 | mefenpyr-diethyl |
| I-f-22 | fenclorim |
| I-f-22 | cumyluron |
| I-f-22 | S4-1 |
| I-f-22 | S4-5 |
| I-f-23 | cloquintocet-mexyl |
| I-f-23 | fenchlorazole-ethyl |
| I-f-23 | isoxadifen-ethyl |
| I-f-23 | mefenpyr-diethyl |
| I-f-23 | fenclorim |
| I-f-23 | cumyluron |
| I-f-23 | S4-1 |
| I-f-23 | S4-5 |
| I-f-24 | cloquintocet-mexyl |
| I-f-24 | fenchlorazole-ethyl |
| I-f-24 | isoxadifen-ethyl |
| I-f-24 | mefenpyr-diethyl |
| I-f-24 | fenclorim |
| I-f-24 | cumyluron |
| I-f-24 | S4-1 |

-continued

| Active compound of the formula | Safener |
|---|---|
| I-f-24 | S4-5 |
| I-f-25 | cloquintocet-mexyl |
| I-f-25 | fenchlorazole-ethyl |
| I-f-25 | isoxadifen-ethyl |
| I-f-25 | mefenpyr-diethyl |
| I-f-25 | fenclorim |
| I-f-25 | cumyluron |
| I-f-25 | S4-1 |
| I-f-25 | S4-5 |

It has now surprisingly been found that the above-defined active compound combinations of compounds of the general formula (I) and safeners (antidotes) from group (b') set out above combine very good compatibility with useful plants with a particularly high herbicidal activity and can be used in various crops, in particular in cereals (especially wheat), but also in soya beans, potatoes, maize and rice, for the selective control of weeds.

In this context, it is considered surprising that, from a multiplicity of known safeners or antidotes capable of antagonizing the damaging effect of a herbicidal crop plant, it is specifically the compounds of group (b') set out above which are suitable for compensating—almost completely—the damaging effect of compounds of the formula (I) on the crop plants, without at the same time having any substantial adverse effect on the herbicidal activity against the weeds.

Emphasis may be given here to the particularly advantageous effect of the preferred and most preferred combination partners from group (b'), particularly with regard to the sparing of cereal plants, such as, for example, wheat, barley and rye, but also maize and rice, as crop plants.

The formula (I) provides a general definition of the compounds according to the invention. Preferred substituents or ranges of the radicals given in the formulae mentioned above and below are illustrated below:

X preferably represents $C_1$-$C_4$-alkyl, $C_3$-$C_6$-cycloalkyl or $C_1$-$C_4$-alkoxy, Y preferably represents hydrogen, $C_1$-$C_4$-alkyl or $C_1$-$C_4$-alkoxy, Z preferably represents hydrogen, $C_1$-$C_4$-alkyl or $C_3$-$C_6$-cycloalkyl, A, B and the carbon atom to which they are attached preferably represent $C_3$-$C_8$-cycloalkyl or $C_5$-$C_8$-cycloalkenyl, in which optionally one or two ring members are replaced by oxygen and/or sulphur and which are optionally mono- to tetrasubstituted by $C_1$-$C_8$-alkyl, $C_1$-$C_8$-alkenyl, $C_1$-$C_4$-alkylene, $C_1$-$C_8$-halogenalkyl, $C_1$-$C_6$-alkoxy-$C_1$-$C_4$-alkyl, $C_1$-$C_6$-alkoxy, $C_1$-$C_6$-halogenalkoxy, hydroxyl, hydroxy-$C_1$-$C_4$-alkyl or benzyloxy, or a further fused-on $C_3$-$C_8$-cycloalkyl ring in which optionally one or two ring members are replaced by oxygen or sulphur, or which is optionally mono- or disubstituted by $C_1$-$C_8$-alkyl, or A, B and the carbon atom to which they are attached preferably represent a carbonyl group, represent a $C_1$-$C_4$-alkylene group or represent a =N—$OR^9$ group, G preferably represents hydrogen (a) or represents one of the groups

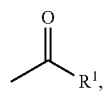
(b)

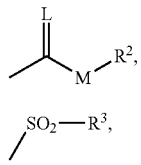
(c)

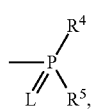
(d)

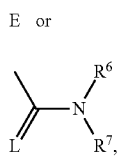
(e)

E or
(f)

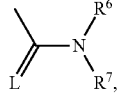
(g)

in which
E represents a metal ion equivalent or an ammonium ion,
L represents oxygen or sulphur, and
M represents oxygen or sulphur, $R^1$ preferably represents in each case optionally halogen-substituted $C_1$-$C_{20}$-alkyl, $C_2$-$C_{20}$ alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, preferably represents optionally halogen-, cyano-, nitro-, $C_1$-$C_6$-alkyl-, $C_1$-$C_6$-alkoxy-, $C_1$-$C_6$-halogenalkyl-, $C_1$-$C_6$-halogenalkoxy-, $C_1$-$C_6$-alkylthio- or $C_1$-$C_6$-alkylsulphonyl-substituted phenyl, preferably represents optionally halogen-, nitro-, cyano-, $C_1$-$C_6$-alkyl-, $C_1$-$C_6$-alkoxy-, $C_1$-$C_6$-halogenalkyl- or $C_1$-$C_6$-halogenalkoxy-substituted phenyl-$C_1$-$C_6$-alkyl, preferably represents optionally halogen- or $C_1$-$C_6$-alkyl-substituted 5- or 6-membered hetaryl (for example pyrazolyl, thiazolyl, pyridyl, pyrimidyl, furanyl or thienyl), preferably represents optionally halogen- or $C_1$-$C_6$-alkyl-substituted phenoxy-$C_1$-$C_6$-alkyl or preferably represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_1$-$C_8$-alkyl, preferably represents optionally halogen-, $C_1$-$C_6$-alkyl- or $C_1$-$C_6$-alkoxy-substituted $C_3$-$C_8$-cycloalkyl or preferably represents in each case optionally halogen-, cyano-, nitro-, $C_1$-$C_6$-alkyl-, $C_1$-$C_6$-alkoxy-, $C_1$-$C_6$-halogenalkyl- or $C_1$-$C_6$-halogenalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-halogenalkyl-, $C_1$-$C_4$-halogenalkoxy-, cyano- or nitro-substituted phenyl or benzyl, R$^4$ and R$^5$ independently of one another preferably represent in each case optionally halogen-substituted C$_1$-C$_8$-alkyl, C$_1$-C$_8$-alkoxy, C$_1$-C$_8$-alkylamino, Di-(C$_1$-C$_8$-alkyl)amino, C$_1$-C$_8$-alkylthio, C$_7$-C$_8$-alkenylthio, C$_3$-C$_7$-Cycloalkylthio or represent in each case optionally halogen-, nitro-, cyano-, C$_1$-C$_4$-alkoxy-, C$_1$-C$_4$-halogenalkoxy-, C$_1$-C$_4$-alkylthio-, C$_1$-C$_4$-halogenalkylthio-, C$_1$-C$_4$-alkyl- or C$_1$-C$_4$-halogenalkyl-substituted phenyl, phenoxy or phenylthio, R$^6$ and R$^7$ independently of one another preferably represent hydrogen, represent in each case optionally halogen-substituted C$_1$-C$_8$-alkyl, C$_3$-C$_8$-cycloalkyl, C$_1$-C$_8$-alkoxy, C$_3$-C$_8$-alkenyl, C$_1$-C$_8$-alkoxy-C$_1$-C$_8$-alkyl, represent optionally halogen-, C$_1$-C$_8$-halogenalkyl-, C$_1$-C$_8$-alkyl- or C$_1$-C$_8$-alkoxy-substituted phenyl, optionally halogen-, C$_1$-C$_3$-alkyl-, C$_1$-C$_8$-halogenalkyl- or C$_1$-C$_8$-alkoxy-substituted benzyl or together represent an optionally C$_1$-C$_4$-alkyl-substituted C$_3$-C$_6$-alkylene radical in which optionally one carbon atom is replaced by oxygen or sulphur, R$^9$ preferably represents hydrogen, represents C$_1$-C$_6$-alkyl, C$_3$-C$_6$-cycloalkyl, CH$_2$C$_3$-C$_6$-cycloalkyl, C$_3$-C$_6$-alkenyl, C$_3$-C$_6$-alkinyl, each of which is optionally mono- to pentasubstituted by halogen, or represents phenyl-C$_1$-C$_2$-alkyl or hetaryl-C$_1$-C$_2$-alkyl, each of which is optionally mono- to trisubstituted by alkyl, halogen, alkoxy, halogenalkyl or halogenalkoxy.

In the radical definitions mentioned as being preferred, halogen represents fluorine, chlorine, bromine and iodine, in particular fluorine, chlorine and bromine. The terms alkyl, alkylidene and alkenyl refer both to straight-chain and to branched hydrocarbon radicals.

X particularly preferably represents methyl, ethyl, cyclopropyl, methoxy or ethoxy, Y particularly preferably represents hydrogen, methyl or ethyl, Z particularly preferably represents hydrogen, methyl, ethyl or cyclopropyl, A, B and the carbon atom to which they are attached particularly preferably represent C$_3$-C$_8$-cycloalkyl or C$_5$-C$_8$-cycloalkenyl in which optionally one or two ring members are replaced by oxygen and/or sulphur and which is optionally mono- to tetrasubstituted by C$_1$-C$_4$-alkyl, C$_1$-C$_4$-alkenyl, a =CH$_2$ group, trifluoromethyl, C$_1$-C$_4$-alkoxy, C$_1$-C$_4$-alkoxy-C$_1$-C$_2$-alkyl or by one of the groups

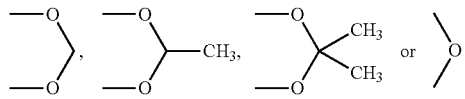

or

A, B and the carbon atom to which they are attached particularly preferably represent a carbonyl group, represent a C$_1$-C$_4$-alkylene group or represent a =N—OR$^9$ group, G particularly preferably represents hydrogen (a) or represents one of the groups (b)

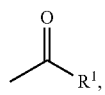

(c)

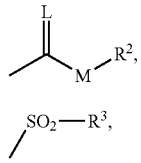

(d)

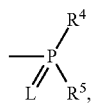

(e)

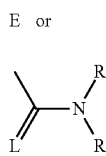

E or (f)

(g)

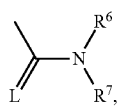

in which

E represents a metal ion equivalent or an ammonium ion,

L represents oxygen or sulphur and

M represents oxygen or sulphur,

R$^1$ particularly preferably represents C$_1$-C$_8$-alkyl, C$_2$-C$_8$-alkenyl, C$_1$-C$_4$-alkoxy-C$_1$-C$_2$-alkyl, C$_1$-C$_4$-alkylthio-C$_1$-C$_2$-alkyl, each of which is optionally mono- to trisubstituted by fluorine or chlorine, or represents C$_3$-C$_6$-cycloalkyl which is optionally mono- or disubstituted by fluorine, chlorine, C$_1$-C$_2$-alkyl or C$_1$-C$_2$-alkoxy and in which optionally one or two not directly adjacent ring members are replaced by oxygen, particularly preferably represents phenyl which is optionally mono- or disubstituted by fluorine, chlorine, bromine, cyano, nitro, C$_1$-C$_4$-alkyl, C$_1$-C$_4$-alkoxy, C$_1$-C$_2$-haloalkyl or C$_1$-C$_2$-haloalkoxy, R$^2$ particularly preferably represents C$_1$-C$_8$-alkyl, C$_2$-C$_8$-alkenyl or C$_1$-C$_4$-alkoxy-C$_2$-C$_4$-alkyl, each of which is optionally mono- to trisubstituted by fluorine, particularly preferably represents C$_3$-C$_6$-cycloalkyl which is optionally monosubstituted by C$_1$-C$_2$-alkyl or C$_1$-C$_2$-alkoxy or particularly preferably represents phenyl or benzyl, each of which is optionally mono- or disubstituted by fluorine, chlorine, bromine, cyano, nitro, C$_1$-C$_4$-alkyl, C$_1$-C$_3$-alkoxy, trifluoromethyl or trifluoromethoxy, R$^3$ particularly preferably represents C$_1$-C$_6$-alkyl which is optionally mono- to trisubstituted by fluorine or represents phenyl which is optionally monosubstituted by fluorine, chlorine, bromine, C$_1$-C$_4$-alkyl, C$_1$-C$_4$-alkoxy, trifluoromethyl, trifluoromethoxy, cyano or nitro, R$^4$ particularly preferably represents C$_1$-C$_6$-alkyl, C$_1$-C$_6$-alkoxy, C$_1$-C$_6$-alkylamino, di-(C$_1$-C$_6$-alkyl)amino, C$_1$-C$_6$-alkylthio, C$_3$-C$_4$-alkenylthio, C$_3$-C$_6$-cycloalkylthio, each of which is optionally mono- to trisubstituted by fluorine or chlorine, or represents phenyl, phenoxy or phenylthio, each of which is optionally monosubstituted by fluorine, chlorine, bromine, nitro, cyano, C$_1$-C$_3$-alkoxy, C$_1$-C$_3$-haloalkoxy, C$_1$-C$_3$-alkylthio, C$_1$-C$_3$-haloalkylthio, C$_1$-C$_3$-alkyl or trifluoromethyl, R$^5$ particularly preferably represents C$_1$-C$_6$-alkylthio or C$_1$-C$_6$-alkoxy which is optionally monosubstituted by chlorine, R$^6$ particularly preferably represents hydrogen, C$_1$-C$_6$-alkyl, C$_3$-C$_6$-cycloalkyl, C$_1$-C$_6$-alkoxy, C$_3$-C$_6$-alkenyl, C$_1$-C$_6$-alkoxy-C$_1$-C$_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent an optionally methyl- or ethyl-substituted $C_4$-$C_5$-alkylene radical in which optionally one methylene group is replaced by oxygen or sulphur, $R^9$ particularly preferably represents hydrogen, represents $C_1$-$C_4$-alkyl, $C_3$-$C_6$-cycloalkyl, $C_3$-$C_4$-alkenyl, $C_3$-$C_4$-alkinyl, each of which is optionally mono- to trisubstituted by fluorine or chlorine, represents benzyl or pyridinylmethyl, each of which is optionally mono- or disubstituted by $C_1$-$C_2$-alkyl, $C_1$-$C_2$-alkoxy, fluorine, chlorine, bromine, trifluoromethyl or trifluoromethoxy.

In the radical definitions mentioned as being particularly preferred, halogen represents fluorine, chlorine and bromine, in particular fluorine and chlorine. The terms alkyl, alkylidene and alkenyl are referred both to straight-chain and to branched hydrocarbon radicals.

X very particularly preferably represents methyl, ethyl, cyclopropyl, methoxy or ethoxy (with emphasis ethyl), Y very particularly preferably represents hydrogen, methyl or ethyl (with emphasis methyl), Z very particularly preferably represents hydrogen, methyl, ethyl or cyclopropyl (with emphasis ethyl), A, B and the carbon atom to which they are attached very particularly preferably represent $C_3$-$C_7$-cycloalkyl or $C_5$-$C_7$-cycloalkenyl in which optionally one or two ring members are replaced by oxygen and/or sulphur and which is optionally mono-, di-, tri- or tetrasubstituted by methyl, in each case monosubstituted by ethyl, a =$CH_2$ group, methoxy or ethoxy, A, B and the carbon atom to which they are attached very particularly preferably represent a carbonyl group, represent a =CH, group, represent a =$CH_2$—$CH_3$ group, represent a =$CH_2$—$C_2H_5$ group or represent a =N—$OR^9$ group, G very particularly preferably represents hydrogen (a) or represents one of the groups

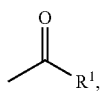
(b)

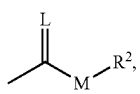
(c)

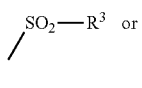
(d)

(f)

E in which
E represents a metal ion equivalent ($Na^+$ or $K^+$),
L represents oxygen or sulphur and
M represents oxygen or sulphur,
$R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or $C_3$-$C_6$-cyclopropyl which is optionally monosubstituted by fluorine, chlorine, methyl or methoxy or represents $C_1$-$C_4$-alkyl which is monosubstituted by chlorine, very particularly preferably represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl or $C_1$-$C_4$-alkoxy-$C_2$-$C_3$-alkyl, each of which is optionally mono- to trisubstituted by fluorine, represents phenyl or benzyl, $R^3$ very particularly preferably represents $C_1$-$C_6$-alkyl or represents phenyl which is optionally monosubstituted by chlorine or $C_1$-$C_4$-alkyl, $R^9$ very particularly preferably represents hydrogen, represents in each case optionally fluorine-substituted methyl, ethyl, propyl, n-butyl, isobutyl, s-butyl or tert-butyl, represents allyl, chloroallyl, propinyl, butinyl, chlorobenzyl, chloropyridylmethyl, $CH(CH_3)$—C≡CH, cyclopropyl, cyclobutyl, cyclopentyl, $CH_2$-cyclopropyl, $CH_2$-cyclobutyl or $CH_2$-cyclopentyl.

X especially preferably represents methyl, ethyl or methoxy,
Y especially preferably represents methyl or ethyl,
Z especially preferably represents hydrogen, methyl or ethyl,
A, B and the carbon atom to which they are attached especially preferably represent $C_5$-$C_7$-cycloalkyl or $C_7$-cycloalkenyl in which optionally two ring members are replaced by oxygen and/or sulphur and which is optionally mono-, di- or tetrasubstituted by methyl, in each case monosubstituted by ethyl, a =CH, group, methoxy, ethoxy or benzyloxy, A, B and the carbon atom to which they are attached especially preferably represent a carbonyl group, represent a =$CH_2$ group or represent a =N—$OR^9$ group, G especially preferably represents hydrogen (a) or represents one of the groups

(b)

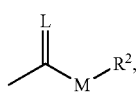
(c)

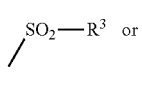
(d)

 or (f)

E in which
E represents a metal ion equivalent,
L represents oxygen and
M represents oxygen,
$R^1$ especially preferably represents $C_1$-$C_6$-alkyl or $C_1$-$C_2$-alkoxy-$C_1$-alkyl or $C_1$-$C_4$-alkyl which is monosubstituted by chlorine,
especially preferably represents phenyl which is optionally monosubstituted by chlorine, methyl or methoxy,
$R^2$ especially preferably represents $C_1$-$C_8$-alkyl,
$R^3$ especially preferably represents methyl, phenyl or p-methylphenyl,
$R^9$ especially preferably represents hydrogen, methyl, isopropyl, isobutyl, tert-butyl, $CH_2CF_3$, propinyl ($CH_2$—

C≡CH), CH(CH₃)—C≡CH, cyclopropyl, cyclopentyl, CH₂-cyclopropyl, CH₂-cyclopentyl.

The general or preferred radical definitions or illustrations listed above can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Emphasis according to the invention is given to the compounds of the formula (I) which contain a combination of the meanings listed above as emphasized.

Special preference according to the invention is given to the compounds of the formula (I) which contain a combination of the meanings listed above as being especially preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Optionally substituted radicals may be mono- or polysubstituted unless indicated otherwise, and in the case of multiple substitutions the substituents can be identical or different.

With particular emphasis, G represents hydrogen.

In addition to the compounds mentioned in the Preparation Examples, the following compounds of the formula (I-1-a) may be specifically mentioned:

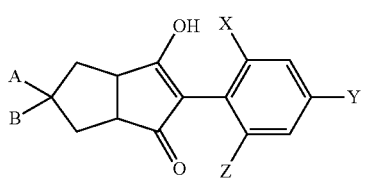

TABLE 1

| A | B |
|---|---|
| | —O—(CH₂)₂—O— |
| | —O—(CH₂)₄—O— |
| | —O—CHCH₃—CH₂—O— |
| | —O—CHCH₃—CHCH₃—O— |
| | —O—(CH₂)₃—O— |
| | —O—CHCH₃—(CH₂)₂—O— |
| | —O—CHCH₃—CH₂—CHCH₃—O— |
| | —O—CH₂—CH(CH₃)—CH₂—O— |
| | —O—CH₂—CH(OCH₃)—CH₂—O— |
| | —O—CH₂—C(CH₃)₂—CH2—O— |
| | —O—CH₂—C(=CH₂)—CH₂—O— |
| | —O—CH₂—CH=CH—CH₂—O— |

TABLE 1-continued

| A | B |
|---|---|
| | —S—(CH₂)₂—S— |
| | —S—(CH₂)3—S— |
| | —O—CH₂—O—CH₂— |
| | —O—C(CH₃)₂—O—CH₂— |

X = CH₃, Y = CH₃, Z = CH₃

Table 2: A and B as mentioned in Table 1 and
X=C₂H₅; Y=CH₃; Z=CH₃
Table 3: A and B as mentioned in Table 1 and
X=C₂H₅; Y=CH₃; Z=C₂H₅
Table 4: A and B as mentioned in Table 1 and
X=C₂H₅; Y=CH₃; Z=C₂H₅
Table 5: A and B as mentioned in Table 1 and
X=▷— ; Y=CH₃; Z=CH₃
Table 6: A and B as mentioned in Table 1 and
X=▷— ; Y=CH₃; Z=C₂H₅
Table 7: A and B as mentioned in Table 1 and
X=OCH₃; Y=CH₃; Z=CH₃
Table 8: A and B as mentioned in Table 1 and
X=OCH₅; Y=CH₃; Z=CH₃
Table 9: A and B as mentioned in Table 1 and
X=OCH₃; Y=CH₃; Z=C₂H₅
Table 10: A and B as mentioned in Table 1 and
X=OC₂H₅; Y=CH₃; Z=C₂H₅
Table 11: A and B as mentioned in Table 1 and
X=C₂H₅; Y=CH₃; Z=H
Table 12: A and B as mentioned in Table 1 and
X=▷— Y=CH₃; Z=▷—
Table 13: A and B as mentioned in Table 1 and
X=C₂H₅; Y=C₂H₅; Z=CH₃

In the literature it has already been described how the action of various active compounds can be boosted by addition of ammonium salts. The salts in question, however, are detersive salts (for example WO 95/017817) or salts which have relatively long alkyl substituents and/or aryl substituents and which have a permeabilizing action or which increase the active compound's solubility (for example EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842, 476). A boost to action by ammonium sulphate, for example, is described by way of example for the herbicides glyphosate, phosphinothricin and for phenyl-substituted cyclic ketoenols (U.S. Pat. No. 6,645,914, EP-A2 0 036 106, WO 07/068,427). A corresponding boost of action in the case of insecticides has already been described in WO 07/068,428.

The use of ammonium sulphate as a formulating assistant has also been described for certain active compounds and applications (WO 92/16108), but its purpose therein is to stabilize the formulation, not to boost the action.

It has now been found, surprisingly, that the action of insecticides and/or acaricides and/or herbicides from the class of the phenyl-substituted bicyclooctane-1,3-dione derivatives of the formula (I) can be boosted significantly through the addition of ammonium salts or phosphonium salts to the application solution or through the incorporation of these salts into a formulation comprising phenyl-substituted bicyclooctane-1,3-dione derivatives of the formula (I). The present invention therefore provides for the use of ammonium salts or phosphonium salts for boosting the action of crop protection compositions which comprise as their active compound herbicidal and/or insecticidal and/or acaricidal phenyl-substituted bicyclooctane-1,3-dione derivatives of the formula (I). The invention likewise provides compositions which comprise herbicidal and/or acaricidal and/or insecticidal phenyl-substituted bicyclooctane-1,3-dione derivatives of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted vegetation.

The active compounds can be used in the compositions according to the invention in a broad concentration range. The concentration of the active compounds in the formulation is typically 0.1%-50% by weight.

Formula (III') provides a definition of the ammonium salts and phosphonium salts which, according to the invention, boost the activity of crop protection compositions comprising fatty acid biosynthesis inhibitors

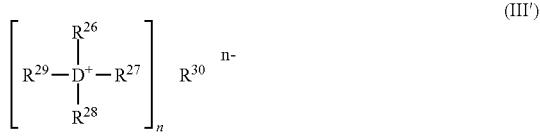

in which

D represents nitrogen or phosphorus,

D preferably represents nitrogen, $R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano, $R^{26}$, $R^{27}$, $R^{28}$ and $R^{29}$ independently of one another preferably represent hydrogen or in each case optionally substituted $C_1$-$C_4$-alkyl, the substituents being selectable from halogen, nitro and cyano, $R^{26}$, $R^{27}$, $R^{28}$ and $R^{29}$ independently of one another particularly preferably represent hydrogen, methyl, ethyl, n-propyl, isopropyl, n-butyl, isobutyl, sec-butyl or tert-butyl, $R^{26}$, $R^{27}$, $R^{28}$ and $R^{29}$ very particularly preferably represent hydrogen, n represents 1, 2, 3 or 4, n preferably represents 1 or 2, $R^{30}$ represents an organic or inorganic anion, $R^{30}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate, $R^{30}$ particularly preferably represents lactate, sulphate, nitrate, thiosulphate, thiocyanate, oxalate or formate.

$R^{30}$ very particularly preferably represents sulphate.

The ammonium salts and phosphonium salts of the formula (III') can be used in a broad concentration range to boost the activity of crop protection compositions comprising phenyl-substituted bicyclooctane-1,3-dione derivatives of the formula (I). In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active compound concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal and/or acaricidal and/or herbicidal phenyl-substituted bicyclooctane-1,3-dione derivatives of the formula (I) as active compound. The invention likewise provides compositions which comprise herbicidal and/or acaricidal and/or insecticidal phenyl-substituted bicyclooctane-1,3-dione derivatives of the formula (I), penetrants and ammonium salts and/or phosphonium salts, including specifically not only formulated active compounds but also ready-to-use compositions (spray liquors). The invention additionally provides, finally, for the use of these compositions for controlling harmful insects and/or spider mites and/or unwanted vegetation.

In the present context, suitable penetrants are all those substances which are usually employed to improve penetration of agrochemically active compounds into plants. In this context, penetrants are defined in that they penetrate from the aqueous spray liquor and/or the spray coating into the cuticles of the plant, thus increasing the mobility of active compounds in the cuticles. The method described in the literature (Baur et al., 1997, *Pesticide Science* 51, 131-152) can be used for determining this property.

Examples of suitable penetrants include alkanol alkoxylates. Penetrants of the invention are alkanol alkoxylates of the formula (IV')

in which

R represents straight-chain or branched alkyl having 4 to 20 carbon atoms,

R' represents hydrogen, methyl, ethyl, n-propyl, isopropyl, n-butyl, isobutyl, tert-butyl, n-pentyl or n-hexyl, AO represents an ethylene oxide radical, a propylene oxide radical, a butylene oxide radical or represents mixtures of ethylene oxide and propylene oxide radicals or butylene oxide radicals, and v represents a number from 2 to 30.

One preferred group of penetrants are alkanol alkoxylates of the formula

in which

R is as defined above,

R' is as defined above,

EO represents —$CH_2$—$CH_2$—O—, and n represents a number from 2 to 20.

A further preferred group of penetrants are alkanol alkoxylates of the formula

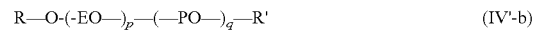

in which
R is as defined above,
R' is as defined above,
EO represents —CH$_2$—CH$_2$—O—,
PO represents

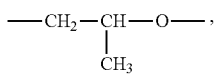

p represents a number from 1 to 10, and
q represents a number from 1 to 10.

A further preferred group of penetrants are alkanol alkoxylates of the formula

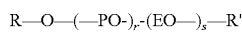 (IV'-c)

in which
R is as defined above,
R' is as defined above,
EO represents —CH$_2$—CH$_2$—O—,
PO represents

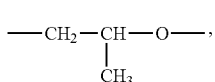

r is a number from 1 to 10, and
s is a number from 1 to 10.

A further preferred group of penetrants are alkanol alkoxylates of the formula

 (IV'-d)

in which
R and R' are as defined above,
EO represents —CH$_2$—CH$_2$—O—,
BO represents

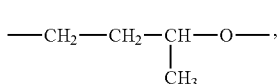

p is a number from 1 to 10 and
q is a number from 1 to 10.

A further preferred group of penetrants are alkanol alkoxylates of the formula

 (IV'-e)

in which
R and R' are as defined above,
BO represents

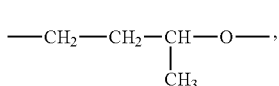

EO represents —CH, —CH$_2$—O—,
r represents a number from 1 to 10 and
s represents a number from 1 to 10.

A further preferred group of penetrants are alkanol alkoxylates of the formula

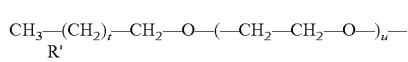 (IV'-f)

in which
R' is as defined above,
t represents a number from 8 to 13,
u represents a number from 6 to 17.

In the formulae indicated above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

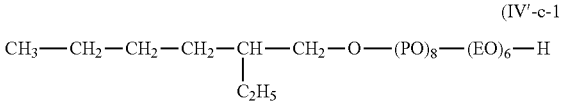 (IV'-c-1)

in which
EO represents —CH$_2$—CH$_2$—O—,
PO represents

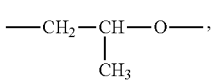

and
the numbers 8 and 6 represent average values.

As an example of an alkanol alkoxylate of the formula (IV'-d) mention may be made of the formula

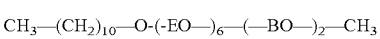 (IV'-d-1)

in which
EO represents —CH$_2$—CH$_2$—O—,
BO represents

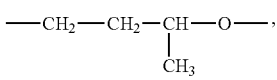

and
the numbers 10, 6 and 2 represent average values.

Particularly preferred alkanol alkoxylates of the formula (IV'-f) are compounds of this formula in which
t represents a number from 9 to 12 and
u represents a number from 7 to 9.

Mention may be made with very particular preference of alkanol alkoxylate of the formula (IV'-f-1)

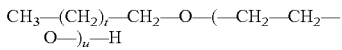 (IV'-f-1)

in which
t represents the average value 10.5 and
u represents the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth) acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarykulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia* spp.,

*Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoans, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus,* Miridae, *Monalonion atratum, Nezara* spp., *Oebalus* spp., Pentomidae, *Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera,* Cercopidae, *Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the *Hymenoptera*, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the *Isoptera*, for example, *Acromyrmex* spp., *Atta* spp., *Cornitermes cumulans, Microtermes obeli, Odontotermes* spp., *Reticulitermes* spp.

From the order of the *Lepidoptera*, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina*.

The plant-parasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, a carrier is a natural or synthetic organic or inorganic substance which may be solid or liquid and with which the active compounds are mixed or bonded for better applicability, in particular for application to plants or parts of plants. The solid or liquid carrier is generally inert and should be suitable for use in agriculture.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists.

Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The compounds of the formula (I) according to the invention (active compounds) have excellent herbicidal activity against a broad spectrum of economically important monocotylidonous and dicotylidonous annual harmful plants. The active compounds also act efficiently on perennial harmful plants which produce shoots from rhizomes, root stocks or other perennial organs and which are difficult to control.

The amount of active compound used may vary within a relatively wide range. It depends essentially on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably from 0.05 to 20 parts by weight, of one of the crop plant compatibility-improving compounds (antidotes/safeners) mentioned above under (b') are present per part by weight of active compound of the formula (I).

The active compound combinations according to the invention are generally applied in the form of finished formulations. However, the active compounds present in the active compound combinations can, as individual formulations, also be mixed during use, i.e. be applied in the form of tank mixtures.

For certain applications, in particular in the post-emergence method, it may furthermore be advantageous to include in the formulations, as further additives, mineral or vegetable oils which are tolerated by plants (for example the commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. The application is in the customary manner, for example by watering, spraying, atomizing, dusting or broadcasting.

The application rates of the active compound combinations according to the invention can be varied within a certain range; they depend, inter alia, on the weather and on soil factors. In general, the application rates are from 0.001 to 5 kg per ha, preferably from 0.005 to 2 kg per ha, particularly preferably from 0.01 to 0.5 kg per ha.

Depending on their properties, the safeners to be used according to the invention can be used for pretreating the seed of the crop plant (seed dressing) or can be introduced into the seed ferrules prior to the seed or be used separately prior to the herbicide or together with the herbicide, before or after emergence of the plants.

Examples of plants which may be mentioned are important crop plants, such as cereals (wheat, barley, rice), maize, soya beans, potatoes, cotton, oilseed rape, beet, sugar cane and also fruit plants (with the fruits apples, pears, citrus fruits and grapevines), greater emphasis being given to cereals, maize, soya beans, potatoes, cotton and oilseed rape.

All plants and plant parts can be treated with the active compounds according to the invention. Here, plants are to be understood as meaning all plants and plant populations such as wanted and unwanted wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders rights. Plant parts are to be understood as meaning all parts and organs of plants above and below the ground, such as shoot, leaf, flower and root, examples which may be mentioned being leaves, needles, stalks, stems, flowers, fruit bodies, fruits and seed and also roots, tubers and rhizomes. The plant parts also include harvested material, and also vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, broadcasting, painting on or injection and, in the case of propagation material, in particular in the case of seed, also by applying one or more coats.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or unwanted crop plants), to the seed (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active compounds are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective compound according to the invention and its application rate. This is why the present compounds are highly suitable for the selective control of unwanted vegetation in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher, quality and/or a higher nutritional value of the harvested products, better storage stability and/or processability of the harvested products are possible, which exceed the effects which were actually to be expected.

Owing to their herbicidal and plant-growth-regulatory properties, the active compounds can also be employed for controlling harmful plants in crops of known genetically modified plants or genetically modified plants which are still to be developed. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known. Further particular properties may be tolerance or resistance to abiotec stresses, for example heat, cold, drought, salt and ultraviolet radiation.

It is preferred to use the compounds of the formula (I) according to the invention in economically important transgenic crops of useful plants and ornamentals, for example of cereals such as wheat, barley, rye, oats, sorghum and millet, rice, cassava and maize or else crops of sugar beet, cotton, soya bean, oilseed rape, potato, tomato, peas and other vegetables.

It is preferred to employ the compounds of the formula (I) as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

recombinant modifications of crop plants for the purposes of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulphonylurea type (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulphonylureas, glyphosate, glufosinate or benzoylisoxazoles and analogous active compounds.

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y.; 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxiddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active compounds, such as, for example, insecticides, acaracides, berbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleylmethyltauride. To prepare the wettable powders, the active herbicidal compounds are ground finely, for example in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active compound onto adsorptive granulated inert material or by applying active compound concentrates by means of adhesives, for example polyvinyl alcohol, sodium polyacrylate or else mineral oils, onto the surface of carriers such as sand, kaolinites or of granulated inert material. It is also possible to granulate suitable active compounds in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In water-dispersible granules, the active compound content depends partly on whether the active compound is present in solid or liquid form and which granulation assistants, fillers, etc. are used. In the granules dispersible in water, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The term "active compounds" or "compounds" in each case also includes the active compound combinations mentioned herein.

According to the invention, the preparation of the compounds of the general structure (I) can be carried out by processes A to H.

Using, for example, according to process (A) methyl 2,2-dimethyl-8-[(2,6-diethyl-4-methyl)phenylacetyl]-1,3-dioxa-[4.4.0]-bicyclononane-7-carboxylate, the course of the process according to the invention can be represented by the reaction scheme below:

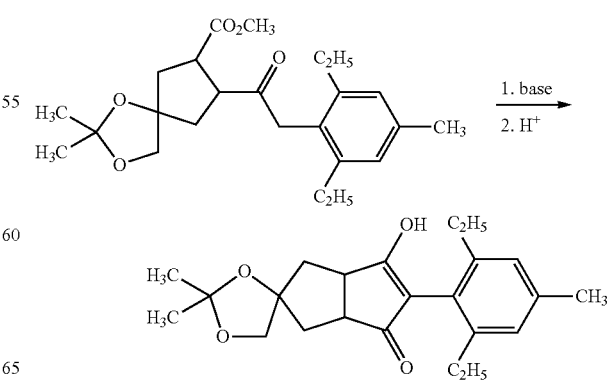

Using, for example, according to process (B) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and pivaloyl chloride as starting materials, the course of the process according to the invention can be represented by the reaction scheme below:

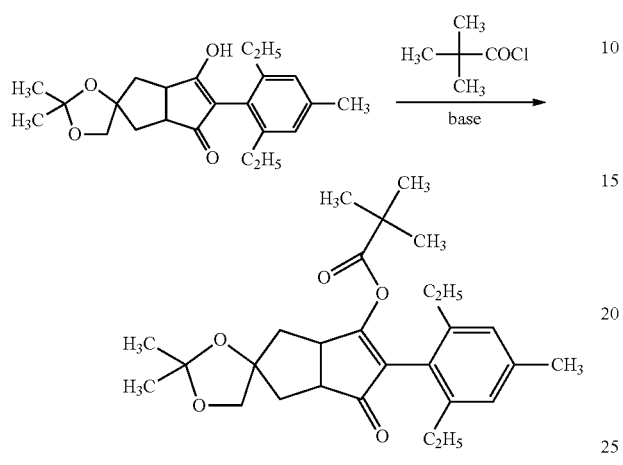

Using, for example, according to process (B) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and acetic anhydride as starting materials, the course of the process according to the invention can be represented by the reaction scheme below:

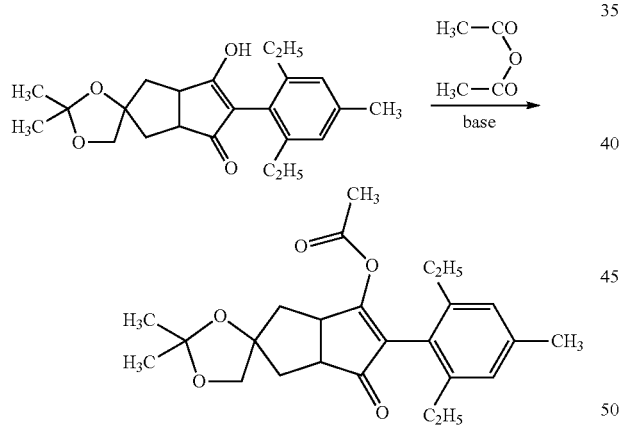

Using, for example, according to process (C) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and ethyl chloroformate as starting materials, the course of the process according to the invention can be represented by the reaction scheme below:

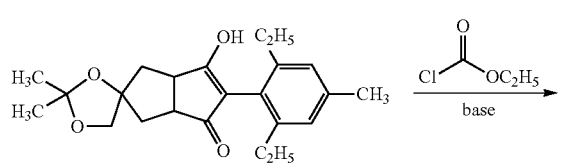

-continued

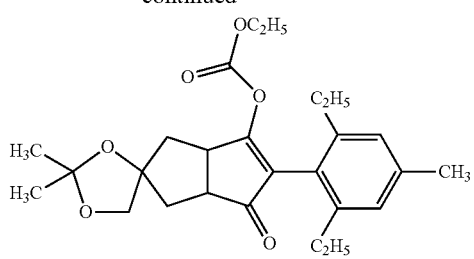

Using, for example, according to process (D) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and methyl chloromonothioformate as starting materials, the course of the process according to the invention can be represented by the reaction scheme below:

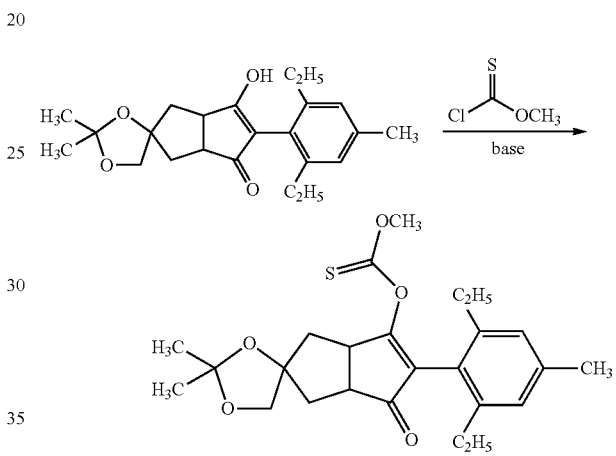

Using, for example, according to process (E) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and methanesulphonyl chloride as starting materials, the course of the reaction can be represented by the reaction scheme below:

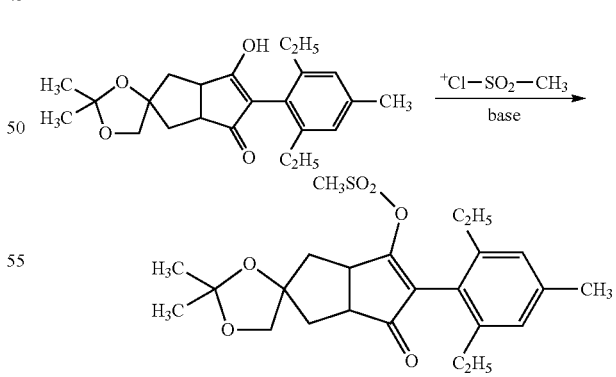

Using, for example, according to process (F) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and 2,2,2-trifluoroethyl methanethiophosphonyl chloride as starting materials, the course of the reaction can be represented by the reaction scheme below:

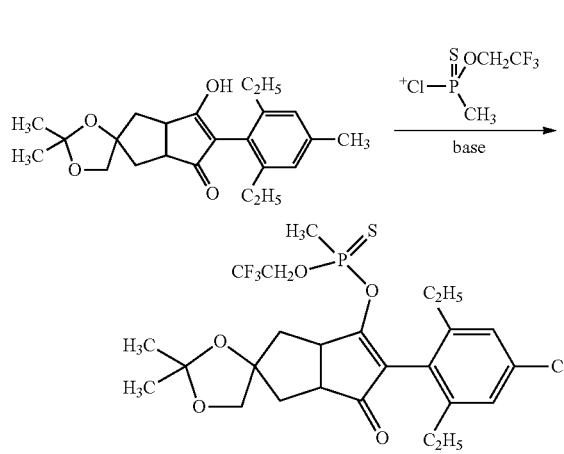

Using, for example, according to process (G) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and NaOH as components, the course of the process according to the invention can be represented by the reaction scheme below:

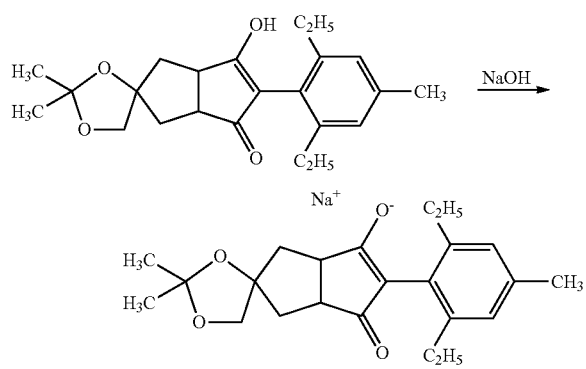

Using, for example, according to process (H), variant α, 5'-(2,6-diethyl-4-methylphenyl)-6'-hydroxy-2,2-dimethyl-1,3',3a',6a'-tetrahydro-4'H-spiro[1,3-dioxolan-4,2'-pentalen]-4'-one and ethyl isocyanate as starting materials, the course of the reaction can be represented by the reaction scheme below:

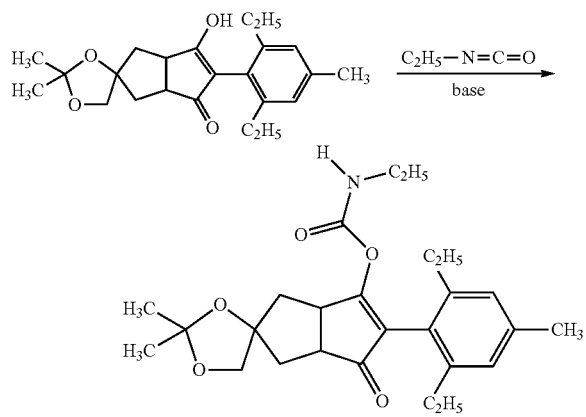

Using, for example, according to process (H), variant β, 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and dimethylcarbamoyl chloride as starting materials, the course of the reaction may be represented by the scheme below:

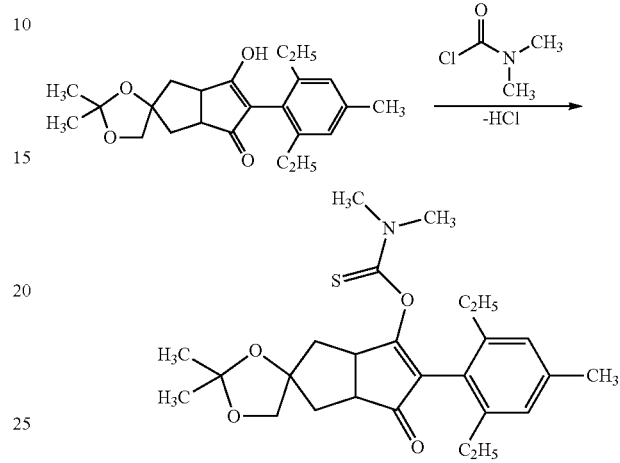

The compounds, required as starting material in process (A) according to the invention, of the formula (II)

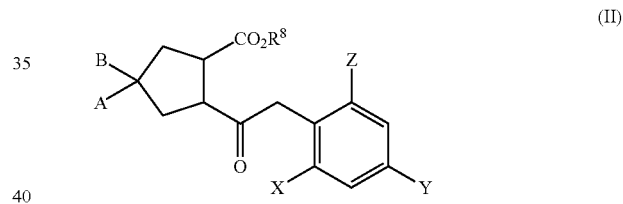

(II)

in which

A, B, X, Y, Z and $R^8$ have the meaning given above are novel.

They can be prepared by methods known in principle.

The 5-aryl-4-ketocarboxylic esters of the formula (II) are obtained, for example, when 5-aryl-4-ketocarboxylic acids of the formula (XIII)

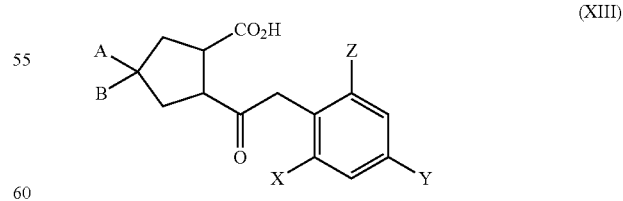

(XIII)

in which

X, Y, Z, A and B have the meaning given above are esterified (cf., for example, Organikum, 15th Edition, Berlin, 1977, page 499) or alkylated (see Preparation Example).

The arylketocarboxylic acids of the formula (XIII)

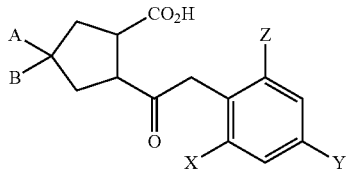
(XIII)

in which
A, B, X, Y and Z have the meaning given above
are novel; however, they can be prepared by methods known in principle (WO 07/080,066, WO 96/01 798, WO 97/14667, WO 98/39281, WO 01/74770).

The arylketocarboxylic acids of the formula (XIII) are obtained, for example, when 2-phenyl-3-oxoadipic esters of the formula (XIV)

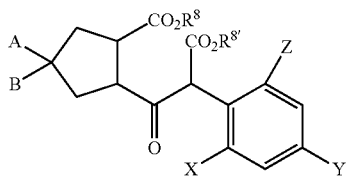
(XIV)

in which
A, B, X, Y and Z have the meaning given above and
$R^8$ and $R^{8'}$ represent alkyl (in particular $C_1$-$C_8$-alkyl) and, when the compound of the formula (XVI) is used, $R^8$ represents hydrogen
are decarboxylated, if appropriate in the presence of a diluent and if appropriate in the presence of a base or acid (cf., for example, Organikum, 15th Edition, Berlin, 1977, pages 519-521).

The compound of the formula (XIV)

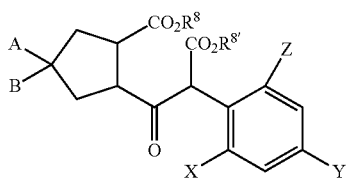
(XIV)

in which
A, B, X, Y, Z, $R^8$, $R^{8'}$ have the meaning given above and,
when the compound of the formula (XVI) is used, $R^8$ represents hydrogen
are novel.

The compounds of the formula (XIV) are obtained, for example,
when dicarboxylic semiester chlorides of the formula (XV)

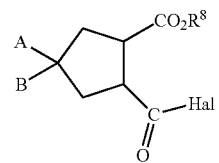
(XV)

in which
A, B and $R^8$ have the meaning given above and
Hal represents chlorine or bromine
or carboxylic anhydrides of the formula (XVI)

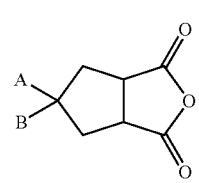
(XVI)

in which
A and B have the meaning given above
are acylated with a phenylacetic ester of the formula (XVII)

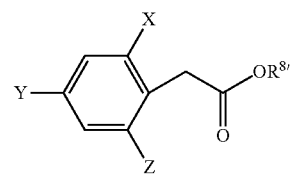
(XVII)

in which
X, Y, Z and $R^8$ have the meaning given above
in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

A further proven method for preparing the compounds, required as starting materials for process (A), of the formula (II) in which A, B, X, Y, Z and $R^8$ have the meaning given above is also, for example, the coupling of benzyl zinc compounds of the general formula (XVIII)

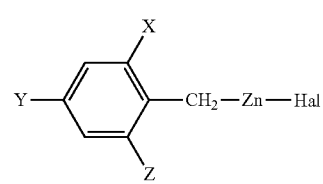
(XVIII)

in which X, Y and Z have the meaning given above and Hal represents a halogen atom, preferably chlorine or bromine, if appropriate in the presence of a catalyst, with a dicarboxylic semiester chloride of the general formula (XV) or a carboxylic anhydride of the general formula (XVI).

Both the preparation and the reaction of organic zinc compounds with carbonyl chlorides and carboxylic anhydrides are known in principle and can be carried out in close analogy to the processes described in the literature. More details are described, for example, in Chem. Commun. 2008, 5824, WO 2007/113294, Tetrahedron Letters 30, 5069-5072 (1989) or Chem. Rev. 1993, 93, 2117-2188.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formulae (IX) and (X) and isocyanates of the formula (XI) and carbamoyl chlorides of the formula (XII) furthermore required as starting materials for carrying out the processes (B), (C), (D), (E), (F), (G) and (H) according to the invention are generally known compounds of organic of inorganic chemistry.

Some of the compounds of the formulae (XV), (XVI) and (XVII) are known compounds of organic chemistry or known from the patent applications cited at the outset and/or can be prepared in a simple manner by methods known in principle or can be prepared by the methods described in the patent applications cited at the outset.

To prepare benzyl zinc compounds of the formula (XVIII), benzyl compounds of the formula (XIX)

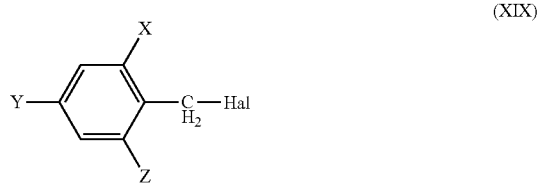

(XIX)

where X, Y and Z have the meaning given above and Hal represents a halogen atom, preferably chlorine or bromine, are used as starting material. Some benzyl compounds of the formula (XIX) are known, or they can be prepared by known processes (see, for example, Chem. Ber. 118, 1968 (1985), Monatshefte Chemie 135, 251 (2004), Acta Chem. Scand. 1963, 17 and Preparation Examples).

The process (A) is characterized in that compounds of the formula (II), in which A, B, X, Y, Z and $R^8$ have the meaning given above are subjected to an intramolecular condensation in the presence of a base.

Suitable for use as diluents in the process (A) according to the invention are all organic solvents which are inert towards the reaction participants. Preference is given to using hydrocarbons, such as toluene and xylene, furthermore ethers, such as bibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (A) according to the invention are all customary protonic ceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride, tetrabutylammonium bromide, Adogen 464 (=methyltrialkyl(C8-C10)ammonium chloride) or TDA 1 (=tris(methoxyethoxyethyl)amine). It is furthermore possible to use alkali metals, such as sodium or potassium. Further, it is possible to employ alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures may be varied within a relatively wide range. In general, the process is carried out at temperatures between 0° C. and 250° C., preferably between 50° C. and 150° C.

The process (A) according to the invention is generally carried out under reduced pressure.

When carrying out the process (A) according to the invention, the reaction components of the formula (II) and the deprotonating bases are generally employed in about doubly equimolar amounts. However, it is also possible to use a relatively large excess (up to 3 mol) of one component or the other.

The process (B-α) is characterized in that compounds of the formula (I-a) are in each case reacted with carbonyl halides of the formula (III), if appropriate in the presence of a diluent and if appropriate in the presence of an acid binder.

Suitable for use as diluents in the process (B-α) according to the invention are all solvents which are inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholan. If the acid halide is sufficiently stable to hydrolysis, the reaction can also be carried out in the presence of water.

Suitable acid binders for the reaction according to process (B-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig-Base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

The reaction temperatures in the process (B-α) according to the invention can be varied within a relatively wide range. In general, the process is carried out at temperatures between −20° C. and +150° C., preferably between 0° C. and 100° C.

When carrying out the process (B-α) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process (B-β) is characterized in that compounds of the formula (I-a) are reacted with carboxylic anhydrides of the formula (IV), if appropriate in the presence of a diluent and if appropriate in the presence of an acid binder.

Suitable diluents for use in the process (B-β) according to the invention are, preferably, the diluents which are also preferred when using acid halides. Besides this a carboxylic anhydride used in excess may simultaneously act as diluent.

Suitable acid binders, which are added, if appropriate, for process (B-β) are, preferably, the acid binders which are also preferred when using acid halides.

The reaction temperatures in the process (B-β) according to the invention may be varied within a relatively wide range. In general, the process is carried out at temperatures between −20° C. and +150° C., preferably between 0° C. and 100° C.

When carrying out the process (B-β) according to the invention, the starting materials of the formula (I-a) and the carboxylic anhydride of the formula (IV) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (C) is characterized in that compounds of the formula (I-a) are in each case reacted with chloroformic esters or chloroformic thio esters of the formula (V), if appropriate in the presence of a diluent and if appropriate in the presence of an acid binder.

Suitable acid binders for the reaction according to the process (C) according to the invention are all customary acid acceptors. Preference is given to use tertiary amines, such as triethylamine, pyrridine, DABCO, DBU, DBA, Hünig-Base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Suitable diluents for use in the process (C) according to the invention are all solvents which are inert towards the chloroformic esters or chloroformic thio esters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholan.

When carrying out the process (C) according to the invention, the reaction temperatures can be varied within a relatively wide range. If the process is carried out in the presence of a diluent and an acid binder, the reaction temperatures, are generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thio ester of the formula (V) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (D) according to the invention is characterized in that compounds of the formula (I-a) are in each case reacted with compounds of the formula (VI) in the presence of a diluent and, if appropriate, in the presence of an acid binder.

In preparation process (D), about one mol of chloromonothioformic ester or chlorodithioformic ester of the formula (VI) is employed per mole of the starting material of the formula (I-a) at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents, such as, for example, sodium hydride or potassium tert-butoxide, the further addition of acid binders may be dispensed with.

If acid binders are used, these are customary inorganic or organic bases; sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods.

The process (E) according to the invention is characterized in that compounds of the formula (I-a) are in each case reacted with sulphonyl chlorides of the formula (VII), if appropriate in the presence of a diluent and if appropriate in the presence of an acid binder.

In preparation process (E), about one mol of sulphonyl chloride of the formula (VII) is reacted per mole of the starting material of the formula (I-a) at from −20 to 150° C., preferably from 20 to 70° C.

Suitable diluents which are added, if appropriate, are all inert polar organic solvents, such as ethers, amides, nitrides, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with phosphorus compounds of the formula (VIII), if appropriate in the presence of a diluent and if appropriate in the presence of an acid binder.

In preparation process (F), to obtain compounds of the formula (I-e), from 1 to 2, preferably from 1 to 1.3, mol of the phosphorus compound of the formula (VIII) are reacted per mole of the compounds of the formula (I-a), at temperatures between −40° C. and 150° C., preferably between −10 and 110° C.

Suitable diluents which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The arising end products are preferably purified by crystallization, chromatographic purification or "incipient distillation" i.e. removal of the volatile components under reduced pressure.

The process (G) is characterized in that compounds of the formula (I-a) are reacted with metal hydroxides or metal alkoxides of the formula (IX) or amines of the formula (X), if appropriate in the presence of a diluent.

Suitable diluents for use in the process (G) according to the invention are, preferably, ethers, such as tetrahydrofuran, dioxane, diethyl ether, or else alcohols, such as methanol, ethanol, isopropanol, and also water.

The process (G) according to the invention is generally carried out under atmospheric pressure.

The reaction temperatures are generally between −20° C. and 100° C., preferably between 0° C. and 50° C.

The process (H) according to the invention is characterized in that compounds of the formula (I-a) are in each case reacted with (H-α) compounds of the formula (XI), if appropriate in the presence of a diluent and if appropriate in the presence of a catalyst, or (H-β) with compounds of the formula (XII), if appropriate in the presence of a diluent and if appropriate in the presence of an acid binder.

In preparation process (H-α), about 1 mol of isocyanate of the formula (XI) is reacted per mole of starting material of the formula (I-a), at from 0 to 100° C., preferably from 20 to 50° C.

Suitable diluents which are added, if appropriate, are all inert organic solvents, such as ethers, amides, nitriles, sulphones, sulphoxides.

If appropriate, catalysts may be added to accelerate the reaction. Suitable for use as catalysts are, very advantageously, organotin compounds, such as, for example dibutyl tin dilaurate. The reaction is preferably carried out at atmospheric pressure.

In preparation process (H-β), about 1 mol of carbamoyl chloride of the formula (XII) is reacted per mole of starting material of the formula (I-a), at from −20 to 150° C., preferably at from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound of the formula (I-a) is prepared by addition of strong deprotonating agents (such as, for example, sodium hydride or potassium tert-butoxide), the further addition of acid binders may be dispensed with.

If acid binders are used, then customary inorganic or organic bases are suitable, for example sodium hydroxide, sodium carbonate, potassium carbonate, triethylamine or pyridine. The reaction can be carried at an atmospheric pressure or under elevated pressure and is preferably carried out at atmospheric pressure. Work-up is carried out by customary methods. The preparation and the use of the active compounds according to the invention is illustrated by the examples below.

PREPARATION EXAMPLES

Examples I-a-1 and I-a-2

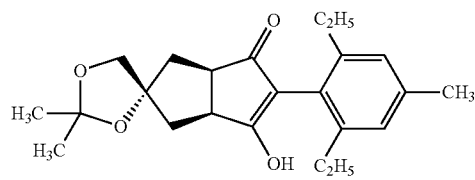

Example I-a-1
anti

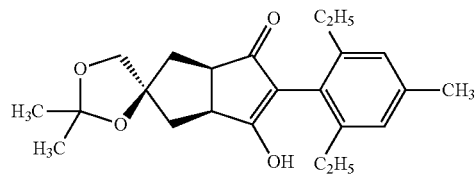

Example I-a-2
syn

In 50 ml of anhydrous N,N-dimethylformamide, 4.62 g (11.5 mmol) of methyl 8-[(2,6-diethyl-4-methylphenyl)acetyl]-2,2-dimethyl-1,3-dioxaspiro[4.4]nonane-7-carboxylate (according to Example (II-5)) and 2.57 g of potassium tert-butoxide are heated at 50° C. for 2 h. After cooling, the mixture is poured into ice-water, acidified to pH 3 using conc. hydrochloric acid and extracted three times with ethyl acetate. The organic phase is dried (magnesium sulphate), and the solvent is then distilled off and the residue is chromatographed on silica gel (ethyl acetate/hexane=50:50).
Fraction A:
anti-isomer (I-a-1); yield 1.70 g (40%); colourless crystals of m.p. 104-105° C.
Fraction B:
syn-isomer (I-a-2); yield 1.40 g (34%); colourless crystals of m.p. 88-89° C.

Example I-a-3

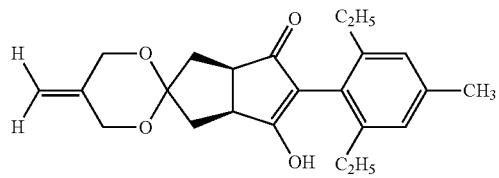

(I-a-3)

In 40 ml of toluene, 0.79 g (2.64 mmol) of 2-(2,6-diethyl-4-methylphenyl)-3-hydroxy-3a,4,6,6a-tetrahydropentalene-1,5-dione (according to Example (I-a-4)), 0.58 g (6.6 mmol) of 2-methylidenepropane-1,3-diol and 20 mg of p-toluene sulphonic acid are heated on a water separator for 3 h, and the mixture is then concentrated using a rotary evaporator and taken up in ethyl acetate. The mixture is extracted with bicarbonate solution and water, dried (magnesium sulphate), the solvent is distilled off and the residue is chromatographed on silica gel (ethyl acetate/hexane v:v=35:65), which then affords the compound of the formula (I-a-3) in the form of colourless crystals.
Yield: 0.52 g (53%)
$^1$H-NMR (400 MHz, CDCl$_3$): δ=1.07 and 1.09 (in each case t, in each case 3H), 3.12 and 3.38 (in each case mc, in each case 1H), 4.10-4.37 (m, 4H), 4.39 (mc, 2H) ppm

Example I-a-4

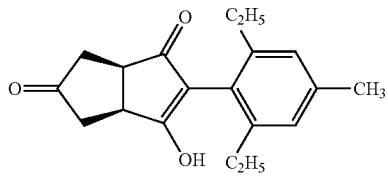

2 ml of a 2.5% strength solution of osmium tetroxide in t-butanol are added to 2.50 g (8.43 mmol) of 2-(2,6-diethyl-4-methylphenyl)-3-hydroxy-5-methylidene-4,5,6,6a-tetrahydropentalen-1(3 aH)-one (according to Example I-a-5) and 9.02 g (42.16 mmol) of sodium meta-periodate in 50 ml of a water/tert-butanol mixture (v/v=50:50), and the mixture is stirred at room temperature for 10 minutes. 50 ml of ethyl acetate are then added, and the mixture is stirred at room temperature for a further 2 h. The reaction mixture is then added to ice, taken up in ethyl acetate and extracted with water. After drying (magnesium sulphate) and distillative removal of the solvent, the residue is chromatographed on silica gel using ethyl acetate/hexane (v/v=30:70). This gives 1.86 g (74.1%) of the compound of the formula (I-a-4) as a viscose oil.

$^1$H-NMR (400 MHz, CDCl$_3$): δ=2.31 (s, 3H), 2.52 and 2.74 (in each case mc, broad, in each case 2H), 3.41 and 3.68 (in each case mc, broad, in each case 1H) ppm

Example I-a-5

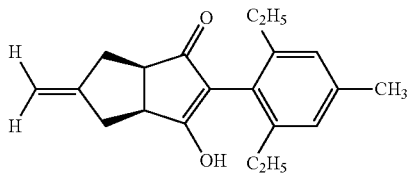

In 80 ml of N,N-dimethylformamide, 7.85 g (23.9 mmol) of methyl 2-[(2,6-diethyl-4-methyl-phenyl)acetyl]-4-methylidenecyclopentanecarboxylate (according to Example (II-1)) and 5.36 g (47.8 mmol) of potassium tert-butoxide are heated at 50° C. for 2 h. After cooling, the mixture is added to ice-water, acidified to pH 2 using conc. hydrochloric acid and extracted with ethyl acetate. The organic phase is washed twice with water, dried (magnesium sulphate) and concentrated using a rotary evaporator. Chromatographic purification on silica gel (mobile phase ethyl acetate/hexane v:v=40:60) gives 4.30 g (61%) of the compound of the formula (I-a-5) in the form of colourless crystals of melting point 127-128° C.

$^1$H-NMR (400 MHz, CDCl$_3$): δ=0.94 and 1.08 (in each case t, in each case 3H), 2.28 (s, 3H), 2.51 (mc, 4H), 4.89 (s, 2H) ppm

Example I-a-18

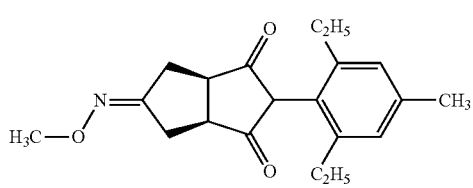

0.164 g (1.62 mmol) of triethylamine is added to 0.161 g (0.54 mmol) of 2-(2,6-diethyl-4-methylphenyl)-3-hydroxy-3a,4,6,6a-tetrahydropentalen-1,5-dione (Example I-a-4) and 0.090 g (1.08 mmol) of N-methylhydroxylamine hydrochloride in 10 ml of acetonitrile, and the mixture is stirred at room temperature for 6 h. The mixture is then added to ice and taken up in ethyl acetate, and the organic phase is separated off and washed with water. Drying (magnesium sulphate), distillative removal of the solvent and chromatography on silica gel using ethyl acetate/hexane (v/v=25:75) finally affords 0.154 g (87%) of the desired compound of the formula (I-a-18) as a viscose yellowish oil.

$^1$H-NMR (400 MHz, CDCl$_3$): δ=2.62 (mc, 1H), 3.20 and 3.48 (in each case mc, in each case 1H), 3.82 (s, 3H) ppm The following compounds of the formula (I-a) are obtained analogously to Examples (I-a-1) to (I-a-5) and (I-a-18) and in accordance with the general statements on the preparation:

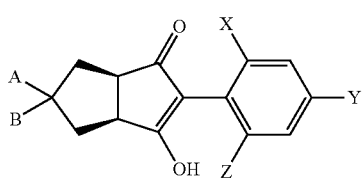

| Ex. No. | X | Y | Z | A | B | M.p. [° C.] or $^1$H-NMR (400 MHz, CDCl$_3$, δ in ppm) | Isomerism |
|---|---|---|---|---|---|---|---|
| I-a-6 | C$_2$H$_5$ | CH$_3$ | C$_2$H$_5$ | —O—CH(C$_2$H$_5$)—O—CH$_2$— | | 181 | anti |
| I-a-7 | C$_2$H$_5$ | CH$_3$ | C$_2$H$_5$ | —O—CH(CH$_3$)—O—CH$_2$— | | δ = 1.48 and 1.49 (2 s, in total 3 H), 3.74 (d, 1 H), 3.87 (d, 1H), 5.09 (s, br, 1 H) | anti |
| I-a-8 | C$_2$H$_5$ | CH$_3$ | C$_2$H$_5$ | —O—(CH$_2$)$_2$—O— | | 2.05-2.22 (m, 4H), 2.30 (s, 3H), 3.10 (mc, 1H), 3.38 (mc, 1 H), 3.88 (mc, 4H), 6.92 (s, 2H) | |

-continued

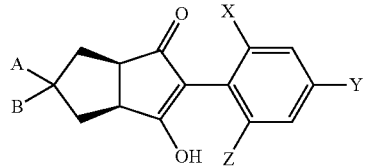
(I-a)

| Ex. No. | X | Y | Z | A B | M.p. [° C.] or $^1$H-NMR (400 MHz, CDCl$_3$, δ in ppm) | Isomerism |
|---|---|---|---|---|---|---|
| I-a-9 | C$_2$H$_5$ | CH$_3$ | C$_2$H$_5$ | —O—CH$_2$—C(CH$_3$)$_2$—CH$_2$—O— | 96-97 | |
| I-a-10 | C$_2$H$_5$ | CH$_3$ | C$_2$H$_5$ | —O—CH(CH$_3$)—CH$_2$—O— | 89-90 | syn/anti mixture |
| I-a-11 | C$_2$H$_5$ | CH$_3$ | C$_2$H$_5$ | —O—(CH$_2$)$_3$—O— | δ = 2.70-2.75 (m, 1H), 3.11 and 3.35 (in each case mc, in each case 1H), 3.78 (mc, 1H), 3.88 (mc, 3H) | |
| I-a-12 | C$_2$H$_5$ | CH$_3$ | C$_2$H$_5$ | —O—CH(CH$_3$)—CH$_2$—CH(CH$_3$)—O— | 117-118 | Mixture with respect to the CH$_3$-groups at the acetal ring |
| I-a-13 | C$_2$H$_5$ | CH$_3$ | C$_2$H$_5$ | —O—(CH$_2$)$_4$—O— | 3.05 and 3.31 (in each case mc, in each case 1H), 3.59 and 3.70 (in each case mc, in each case 2H), 7.02 and 7.06 (in each case s, in each case 1H) | |
| I-a-14 | C$_2$H$_5$ | CH$_3$ | C$_2$H$_5$ | —O—CH$_2$—CH=CH—CH$_2$—O— | 3.10 and 3.39 (in each case mc, in each case 1H), 4.04-4.31 (m, 4H); 5.67 (s, 2H) | |
| I-a-15 | C$_2$H$_5$ | CH$_3$ | C$_2$H$_5$ | —O—CH(CH$_3$)—CH$_2$—CH(CH$_3$)—O— | 79-80 | (R,R)-Configuration of the CH$_3$-groups at the acetal ring |
| I-a-16 | C$_2$H$_5$ | CH$_3$ | C$_2$H$_5$ | —S—(CH$_2$)$_2$—S— | δ = 2.61 (mc, 2H), 3.32 (mc, 1H), 6.98 (s, 1H) | |
| I-a-17 | C$_2$H$_5$ | CH$_3$ | C$_2$H$_5$ | —S—(CH$_2$)$_3$—S— | δ = 2.75-3.01 (m, 4H), 3.49 and 3.61 (in each case mc, in each case 1H) | |
| I-a-18 | C$_2$H$_5$ | CH$_3$ | C$_2$H$_5$ | =N—OCH$_3$ | δ = 2.62 (mc, 1H), 3.20 and 3.48 (in each case mc, in each case 1 H), 3.82 (s, 3 H) | |
| I-a-19 | C$_2$H$_5$ | CH$_3$ | C$_2$H$_5$ | —O—C(CH$_3$)$_2$—C(CH$_3$)$_2$—O— | δ = 1.09 and 1.12 (in each case t, in each case 3 H), 1.14 and 1.15 (in each case s, in each case 6H), 2.10-2.21 (m, 4 H), 3.08 and 3.34 (in each case mc, in each case 1 H) | |
| I-a-20 | C$_2$H$_5$ | CH$_3$ | C$_2$H$_5$ | —S—(CH$_2$)$_3$—O— | 93-94 | syn/anti mixture |
| I-a-21 | C$_2$H$_5$ | C$_2$H$_5$ | C$_2$H$_5$ | CH$_2$= | 173-174 | |
| I-a-22 | C$_2$H$_5$ | C$_2$H$_5$ | C$_2$H$_5$ | O= | 243-244 | |
| I-a-23 | C$_2$H$_5$ | C$_2$H$_5$ | C$_2$H$_5$ | —O—(CH$_2$)$_2$—O— | 193-194 | |
| I-a-24 | C$_2$H$_5$ | C$_2$H$_5$ | C$_2$H$_5$ | —O—(CH$_2$)$_3$—O— | 196-197 | |
| I-a-25 | C$_2$H$_5$ | CH$_3$ | C$_2$H$_5$ | —OCH$_2$CH(CH$_3$)CH$_2$O— | 89-90 | |
| I-a-26 | C$_2$H$_5$ | CH$_3$ | C$_2$H$_5$ | —OCH$_2$CH(OCH$_3$)CH$_2$O— | 171-172 | |
| I-a-27 | C$_2$H$_5$ | CH$_3$ | C$_2$H$_5$ | —OCH$_2$CH(OCH$_2$C$_6$H$_5$)CH$_2$O— | 75-76 | |
| I-a-28 | C$_2$H$_5$ | CH$_3$ | C$_2$H$_5$ | —OCH$_2$CH(OC$_2$H$_5$)CH$_2$O— | 75-76 | |
| I-a-29 | C$_2$H$_5$ | CH$_3$ | C$_2$H$_5$ | =NOi-C$_3$H$_7$ | 143 | |
| I-a-30 | C$_2$H$_5$ | CH$_3$ | C$_2$H$_5$ | =NO-cyclopropyl | 79-80 | |
| I-a-31 | C$_2$H$_5$ | CH$_3$ | C$_2$H$_5$ | =NOCH$_2$-cyclopropyl | 70-71 | |
| I-a-32 | C$_2$H$_5$ | CH$_3$ | C$_2$H$_5$ | =NOCH(CH$_3$)—C≡CH | 70 | |
| I-a-33 | C$_2$H$_5$ | CH$_3$ | C$_2$H$_5$ | =NOCH$_2$—C≡CH | 61-62 | |
| I-a-34 | C$_2$H$_5$ | CH$_3$ | C$_2$H$_5$ | —O—CH(CH$_3$)—CH$_2$—CH$_2$—O— | 89-90 | syn/anti mixture |
| I-a-35 | C$_2$H$_5$ | CH$_3$ | C$_2$H$_5$ | —S—(CH$_2$)$_2$—O— | 246 | syn/anti mixture |
| I-a-36 | CH$_3$ | CH$_3$ | CH$_3$ | =CH$_2$ | 202-203 | |
| I-a-37 | CH$_3$ | CH$_3$ | CH$_3$ | —O—(CH$_2$)$_3$—O— | 225-226 | |
| I-a-38 | CH$_3$ | CH$_3$ | CH$_3$ | —OCH$_2$CH(CH$_3$)CH$_2$O— | 225 | |
| I-a-39 | CH$_3$ | CH$_3$ | CH$_3$ | —O—(CH$_2$)$_2$—O— | 236 | |
| I-a-40 | CH$_3$ | CH$_3$ | CH$_3$ | —O—(CH$_2$)$_4$—O— | 216-217 | |
| I-a-41 | CH$_3$ | CH$_3$ | CH$_3$ | —O—CH$_2$—CH=CH—CH$_2$—O— | 203-204 | |
| I-a-42 | CH$_3$ | CH$_3$ | CH$_3$ | —O—C(CH$_3$)$_2$—O—CH$_2$— | 186-187 | |
| I-a-43 | CH$_3$ | CH$_3$ | CH$_3$ | =NOCH$_2$—C≡CH | 70-71 | |
| I-a-44 | CH$_3$ | CH$_3$ | CH$_3$ | =NOCH$_3$ | 105-106 | |
| I-a-45 | OCH$_3$ | CH$_3$ | CH$_3$ | CH$_2$= | 201-202 | |
| I-a-46 | OCH$_3$ | CH$_3$ | CH$_3$ | O= | 230 | |

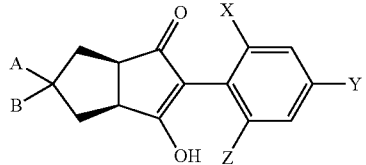

(I-a)

| Ex. No. | X | Y | Z | A B | M.p. [° C.] or ¹H-NMR (400 MHz, CDCl₃, δ in ppm) | Isomerism |
|---|---|---|---|---|---|---|
| I-a-47 | OCH₃ | CH₃ | CH₃ | —O—(CH₂)₃—O— | 2.12 and 2.30 (in each case s, in each case 3H), 3.09 and 3.34 (in each case mc, in each case 1H), 3.27 (s, 3H) | |
| I-a-48 | OCH₃ | CH₃ | CH₃ | —O—(CH₂)₂—O— | 144-145 | |
| I-a-49 | OCH₃ | CH₃ | CH₃ | —O—CH₂—CH=CH—CH₂—O— | 184-185 | |
| I-a-50 | OCH₃ | CH₃ | CH₃ | —O—(CH₂)₄—O— | 202-203 | |
| I-a-51 | OCH₃ | CH₃ | C₂H₅ | CH₂= | 206 | |
| I-a-52 | OCH₃ | CH₃ | C₂H₅ | O= | 244 | |
| I-a-53 | OCH₃ | CH₃ | C₂H₅ | —O—(CH₂)₂—O— | 263 | |
| I-a-54 | OCH₃ | CH₃ | C₂H₅ | —O—(CH₂)₃—O— | 78-79 | |
| I-a-55 | C₂H₅ | CH₃ | CH₃ | CH₂= | 164-165 | |
| I-a-56 | C₂H₅ | CH₃ | CH₃ | O= | 175 | |
| I-a-57 | C₂H₅ | CH₃ | CH₃ | —O—(CH₂)₂—O— | 195 | |
| I-a-58 | C₂H₅ | CH₃ | CH₃ | —O—(CH₂)₃—O— | 135-136 | |
| I-a-59 | C₂H₅ | CH₃ | CH₃ | —O—CH₂—C(CH₃)₂—CH₂—O— | | |
| I-a-60 | C₂H₅ | CH₃ | CH₃ | —O—CH₂—CH=CH—CH₂—O— | 198-199 | |
| I-a-61 | C₂H₅ | CH₃ | CH₃ | —O—(CH₂)₄—O— | 208-209 | |
| I-a-62 | C₂H₅ | CH₃ | CH₃ | —O—C(CH₃)₂—O—CH₂— | 81-82 | anti |
| I-a-63 | C₂H₅ | CH₃ | H | —O—C(CH₃)₂—O—CH₂— | | |
| I-a-64 | C₂H₅ | CH₃ | H | —O—(CH₂)₄—O— | 1.12 (t, 3H), 2.32 (s, 3H), 2.49 (1, 2H), 3.55 and 3.70 (in each case mc, in each case 2H), 6.91 (d, 1H), 7.02 (d, 2H), 7.11 (s, 1H) | |
| I-a-65 | C₂H₅ | CH₃ | H | —O—CH₂—CH=CH—CH₂—O— | | |
| I-a-66 | C₂H₅ | CH₃ | H | —O—(CH₂)₃—O— | 1.12 (t, 3H), 2.31 (s, 3H), 2.72 (mc, 1H), 3.08 (mc, 1H), 3.30 (mc, 1H), | |
| I-a-67 | C₂H₅ | CH₃ | H | —O—(CH₂)₂—O— | 79-80 | |
| I-a-68 | C₂H₅ | CH₃ | C₂H₅ | =NOt-C₄H₉ | 1.00 and 1.09 (in each case t, in each case 3H), 1.22 (s, 9H), 2.30 (s, 3H) | |
| I-a-69 | C₂H₅ | CH₃ | C₂H₅ | =NOi-C₄H₉ | 0.90 (mc, 6H), 1.92 (hept, 1H), 3.20 and 3.39 (in each case mc, in each case 1H), 3.79 (mc, 2H), 6.91 and 6.93 (in each case s, in each case 1H) | |
| I-a-70 | C₂H₅ | CH₃ | C₂H₅ | =NOCH₂CF₃ | 2.60-2.86 (m, 3H), 3.22 and 3.51 (in each case mc, in each case 1H), 4.48 (mc, 2H) | |
| I-a-71 | C₂H₅ | CH₃ | H | CH₂= | 172 | |
| I-a-72 | C₂H₅ | CH₃ | C₂H₅ | =NOH | 119-120 | |
| I-a-73 | C₂H₅ | CH₃ | H | O= | 68-69 | |
| I-a-74 | C₂H₅ | CH₃ | C₂H₅ | —O—CH(C₂H₅)—CH₂—O | | syn/anti mixture |
| I-a-75 | C₂H₅ | CH₃ | C₂H₅ | —O—CH(CH₃)—CH(CH₃)—O— | | Mixture with respect to the CH₃-groups at the acetal ring |

Example I-b-1

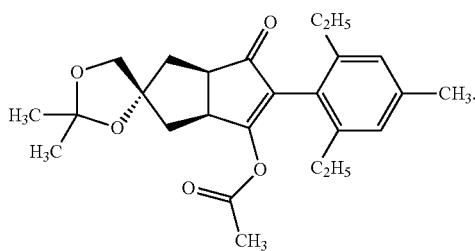

(I-b-1)

At room temperature, 0.100 g (0.27 mmol) of the compound I-a-1 according to the invention (anti-isomer), 23.3 mg (0.297 mmol) of acetyl chloride and 82 mg (0.297 mmol) of triethylamine are stirred in 5 ml of dichloromethane for 2 h. The reaction mixture is poured onto ice, taken up in dichloromethane, washed with water, dried (magnesium sulphate) and concentrated using a rotary evaporator. Chromatography on silica gel (mobile phase ethyl acetate/hexane v:v=30:70) gives the compound of the formula (I-b-1) according to the invention as a colourless oil. Yield 76.6 mg (68%).

¹H-NMR (400 MHz, CDCl₃): δ 1.39 (s, 6H), 2.10 (s, 3H), 2.21 (s, 3H), 3.85 (dd, 2H) ppm The following compounds of the formula (I-b) are obtained analogously to Example (I-b-1) and in accordance with the general statements on the preparation:

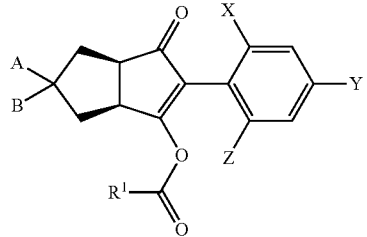

(I-b)

| Ex. No. | X | Y | Z | A B | R¹ | M.p. [° C.] or ¹H-NMR (400 MHz, CDCl₃, δ in ppm) | Isomerism |
|---|---|---|---|---|---|---|---|
| I-b-2 | $C_2H_5$ | $CH_3$ | $C_2H_5$ | —O—C(CH₃)₂—O—CH₂— | $C_2H_5$ | 83 | anti |
| I-b-3 | $C_2H_5$ | $CH_3$ | $C_2H_5$ | —O—C(CH₃)₂—O—CH₂— | i-$C_3H_7$ | 108-109 | anti |
| I-b-4 | $C_2H_5$ | $CH_3$ | $C_2H_5$ | —O—C(CH₃)₂—O—CH₂— | H₃C—O—CH₂— | 3.29 (s, 3H), 3.39 (mc, 1 H), 3.88 (dd, 2H), 4.02 (s, 2 H) | anti |
| I-b-5 | $C_2H_5$ | $CH_3$ | $C_2H_5$ | —O—C(CH₃)₂—O—CH₂— | t-$C_4H_9$ | 114-115 | anti |
| I-b-6 | $C_2H_5$ | $CH_3$ | $C_2H_5$ | —O—C(CH₃)₂—O—CH₂— | $C_2H_5$ | 1.12 (t, 3 H), 2.49 (q, 2 H), 3.90 (dd, 2 H) | syn |
| I-b-7 | $C_2H_5$ | $CH_3$ | $C_2H_5$ | —O—C(CH₃)₂—O—CH₂— | i-$C_3H_7$ | δ = 1.32 (d, 6H), 2.60 (hept, 1H), 3.19 (mc, 1H), 4.01 (mc, 1H) | syn |
| I-b-8 | $C_2H_5$ | $CH_3$ | $C_2H_5$ | —O—C(CH₃)₂—O—CH₂— | t-$C_4H_9$ | 73 | syn |
| I-b-9 | $C_2H_5$ | $CH_3$ | $C_2H_5$ | —S—(CH₂)₃—S— | $C_2H_5$ | δ = 1.01 (3 × t, 9 H), 2.70-2.98 (m, 5 H) | |
| I-b-10 | $C_2H_5$ | $CH_3$ | $C_2H_5$ | —S—(CH₂)₃—S— | H₃C—O—CH₂— | δ = 2.62 (mc, 1 H), 2.70-2.97 (m, 5 H), 3.32 (s, 3 H), 4.02 (dd, 2H) | |
| I-b-11 | $C_2H_5$ | $CH_3$ | $C_2H_5$ | —S—(CH₂)₃—S— | i-$C_3H_7$ | δ = 1.09 (d, 6 H), 2.58 (hept, 1 H), 3.48 and 4.20 (in each case mc, in each case 1H) | |
| I-b-12 | $C_2H_5$ | $CH_3$ | $C_2H_5$ | —O—CH₂—CH=CH—CH₂—O— | i-$C_3H_7$ | 116-117 | |
| I-b-13 | $C_2H_5$ | $CH_3$ | $C_2H_5$ | —O—CH₂—C(=CH₂)—CH₂—O— | i-$C_3H_7$ | 108-109 | |
| I-b-14 | $C_2H_5$ | $CH_3$ | $C_2H_5$ | —OCH₂CH(CH₃)CH₂O— | i-$C_3H_7$ | 116 | |
| I-b-15 | $C_2H_5$ | $CH_3$ | $C_2H_5$ | —O—CHCH₃—CH₂—CHCH₃—O— | i-$C_3H_7$ | 1.00-1.26 (m, 18H), 2.58, hept, 1H) 3.20 (mc, 1H), 3.90-4.00 (m, 2 + 1H) | (R,R)-Configuration of the CH₃-groups at the acetal ring |
| I-b-16 | $C_2H_5$ | $CH_3$ | $C_2H_5$ | —OCH₂CH(OC₂H₅)CH₂O— | i-$C_3H_7$ | 2.59 (hept, 1H), 3.19 (mc, 1H), 3.40 mc, 1H), 3.50 (mc, 3H), 3.98 (mc, 2H), 4.22 (mc, 1H) | |
| I-b-17 | $C_2H_5$ | $CH_3$ | $C_2H_5$ | —OCH₂CH(OCH₂C₆H₅)CH₂O— | i-$C_3H_7$ | 1.09 m, 3H), 3.18 (mc, 1H), 3.40 (mc, 1H), 3.69-4.00 (m, 5H), 4.60 (s, 2H) | |
| I-b-18 | $C_2H_5$ | $CH_3$ | $C_2H_5$ | —O—(CH₂)₂—O— | $CH_3$ | 132 | |
| I-b-19 | $C_2H_5$ | $CH_3$ | $C_2H_5$ | —S—(CH₂)₂—O— | t-$C_4H_9$ | 129-130 | syn/anti mixture |
| I-b-20 | $C_2H_5$ | $CH_3$ | $C_2H_5$ | —S—(CH₂)₃—O— | t-$C_4H_9$ | 1.07 (s, 9H), 2.98-3.03 (m, 2H), 3.76 (mc, 2H), 4.00 (mc, 1H) | syn/anti mixture |
| I-b-21 | $C_2H_5$ | $CH_3$ | $C_2H_5$ | —S—(CH₂)₂—O— | i-$C_3H_7$ | 1.04 (mc, 6H), 2.60 (hept, 1H), 3.01 (mc, 1H), 3.95-4.12 (m, 3H) | syn/anti mixture |
| I-b-22 | $C_2H_5$ | $CH_3$ | $C_2H_5$ | —O—(CH₂)₃—O— | t-$C_4H_9$ | 1.05 (s, 9H), 2.77 (mc, 1H), 3.18 (mc, 1H), 3.75-3.94 (m, 5H) | |
| I-b-23 | $C_2H_5$ | $CH_3$ | $C_2H_5$ | —O—(CH₂)₃—O— | $CH_3$ | 2.11 and 2.32 (jes, in each case 3H), 3.18 (mc, 1H), 3.72-3.90 (m, 4H), 3.95 (mc, 1H) | |
| I-b-24 | $C_2H_5$ | $CH_3$ | $C_2H_5$ | —O—(CH₂)₃—O— | $C_2H_5$ | 99-100 | |
| I-b-25 | $C_2H_5$ | $CH_3$ | $C_2H_5$ | —O—(CH₂)₃—O— | C(CH₃)₂CH₂Cl | 1.10 and 1.15 (in each case s, in each case 3H), 1.58 (mc, 2H), 1.82 (mc, 1H), 2.03-2.10 (m. 2H), 3.40 and 3.48 (in each case d, in each case 1H) | |
| I-b-26 | $C_2H_5$ | $CH_3$ | $C_2H_5$ | CH₂= | t-$C_4H_9$ | 1.05 (s, 9H), 2.22-2.40 (m, 5H), 2.54-2.74 (m, 5H), 4.91 (mc, 2H) | |
| I-b-27 | $C_2H_5$ | $CH_3$ | $C_2H_5$ | —O—(CH₂)₃—O— | t-$C_4H_9$ | 77-78 | |
| I-b-28 | $C_2H_5$ | $CH_3$ | $C_2H_5$ | —O—(CH₂)₃—O— | H₃C—O—CH₂— | 94-95 | |
| I-b-29 | $C_2H_5$ | $CH_3$ | $C_2H_5$ | —O—(CH₂)₃—O— | i-$C_3H_7$ | 95-96 | |
| I-b-30 | $C_2H_5$ | $CH_3$ | $C_2H_5$ | —O—(CH₂)₃—O— | —C(CH₃)₂C₂H₅ | 93-94 | |
| I-b-31 | $C_2H_5$ | $CH_3$ | $C_2H_5$ | —O—(CH₂)₂—O— | i-$C_3H_7$ | 1.05 and 1.10 (in each case mc, in each case 6H), 2.59 (hept, 1H), 3.20 (mc, 1H), 3.90 (mc, 4H), 4.00 (mc, 1H) | |
| I-b-32 | $C_2H_5$ | $CH_3$ | $C_2H_5$ | —O—(CH₂)₂—O— | t-$C_4H_9$ | 108-109 | |
| I-b-33 | $C_2H_5$ | $CH_3$ | $C_2H_5$ | —O—(CH₂)₂—O— | $C_6H_5$ | 2.28 (s, 3H), 3.90 (mc, 4H), 6.88 and 6.91 (in each case s, in each case 1H), 7.41 (t, 2H), 7.60 (t, 2H), 7.90 (d, 2H) | |
| I-b-34 | $C_2H_5$ | $CH_3$ | $C_2H_5$ | —O—(CH₂)₂—O— | p-Cl—$C_6H_5$ | 2.30 (s, 3H), 3.88 (mc, 4H), 7.40 (d, 2H), 7.82 (d, 2H) | |

-continued

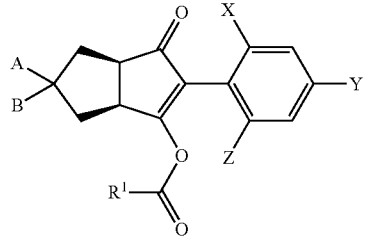

(I-b)

| Ex. No. | X | Y | Z | A | B | R¹ | M.p. [° C.] or ¹H-NMR (400 MHz, CDCl₃, δ in ppm) | Isomerism |
|---|---|---|---|---|---|---|---|---|
| I-b-35 | $C_2H_5$ | $CH_3$ | $C_2H_5$ | —O—$(CH_2)_2$—O— | | p-$CH_3$—$C_6H_5$ | 2.30 and 2.38 (in each case s, in each case 3H), 3.88 (mc, 4H), 4.21 (mc, 1H), 7.20 (d, 2H), 7.79 (d, 2H) | |
| I-b-36 | $C_2H_5$ | $CH_3$ | $C_2H_5$ | —O—$(CH_2)_2$—O— | | p-$OCH_3$—$C_6H_5$ | 120-121 | |
| I-b-37 | $CH_3$ | $CH_3$ | $CH_3$ | $CH_2$= | | t-$C_4H_9$ | 87 | |
| I-b-38 | $CH_3$ | $CH_3$ | $CH_3$ | $CH_2$= | | i-$C_3H_7$ | 1.03 and 1.11 (2 × d, Σ 6H), 2.00, 2.05 and 2.21 (in each case s, in each case 3H), 2.57 (hept, 1H), 4.90 (mc, 2H) | |
| I-b-39 | $CH_3$ | $CH_3$ | $CH_3$ | —O—$(CH_2)_2$—O— | | i-$C_3H_7$ | 1.02 and 1.08 (2 × d, Σ 6H), 2.03, 2.11 and 2.23 (in each case s, in each case 3H), 2.58 (hept, 1H), 3.88 (mc, 4H) | |
| I-b-40 | $CH_3$ | $CH_3$ | $CH_3$ | —O—$(CH_2)_4$—O— | | t-$C_4H_9$ | 134-135 | |
| I-b-41 | $CH_3$ | $CH_3$ | $CH_3$ | —O—$(CH_2)_4$—O— | | i-$C_3H_7$ | 106-107 | |
| I-b-42 | $CH_3$ | $CH_3$ | $CH_3$ | —O—$CH_2$—CH=CH—$CH_2$—O— | | i-$C_3H_7$ | 1.02 and 1.09 (2 × d, Σ 6H), 2.57 (hept, 1H), 3.88 (mc, 4H), 4.00-4.31 (m, 4H), 5.65 (mc, 2H) | |
| I-b-43 | $CH_3$ | $CH_3$ | $CH_3$ | —O$CH_2$CH($CH_3$)$CH_2$O— | | i-$C_3H_7$ | 0.71 and 0.88 (in each case d, Σ 3H), 1.02 and 1.10 (in each case mc, in each case 3H), 2.58 (mc, 1H), 3.30-3.45 (m, 2H), 3.40-3.88 (m, 3H) | |
| I-b-44 | $CH_3$ | $CH_3$ | $CH_3$ | —O—C$(CH_3)_2$—O—$CH_2$— | | i-$C_4H_9$ | 0.88 (mc, 6H), 1.48 (s, 6H), 3.31 (mc, 1H), 3.83 and 3.89 (in each case d, in each case 1H), 6.82 (s, 2H) | syn/anti mixture |
| I-b-45 | $CH_3$ | $CH_3$ | $CH_3$ | —O—C$(CH_3)_2$—O—$CH_2$— | | —C$(CH_3)_2$$C_2H_5$ | 88 | syn/anti mixture |
| I-b-46 | $CH_3$ | $CH_3$ | $CH_3$ | —O—C$(CH_3)_2$—O—$CH_2$— | | i-$C_3H_7$ | 1.01 (mc, 6H), 1.38 (s, 6H), 2.58 (hept, 1H), 3.32 (mc, 1H), 3.85 and 3.90 (in each case d, in each case 2H), 3.88 (mc, 1H) | syn/anti mixture |
| I-b-47 | $CH_3$ | $CH_3$ | $CH_3$ | —O—C$(CH_3)_2$—O—$CH_2$— | | $H_3C$—O—$CH_2$— | 1.38 (s, 6H), 3.28 (s, 3H), 3.85 and 3.89 (in each case d, in each case 1H), 3.98 and 4.04 (in each case d, in each case 1H), 6.84 (s, 2H) | syn/anti mixture |
| I-b-48 | $CH_3$ | $CH_3$ | $CH_3$ | —O—C$(CH_3)_2$—O—$CH_2$— | | t-$C_4H_9$ | 97-98 | syn/anti mixture |
| I-b-49 | $CH_3$ | $CH_3$ | $CH_3$ | —O—C$(CH_3)_2$—O—$CH_2$— | | $CH_3$ | 1.40 (s, 6H), 2.05 (s, 3H), 2.10 (s, 6H), 2.26 (s, 3H), 3.84 and 3.88 (in each case d, in each case 1H) | syn/anti mixture |
| I-b-50 | $CH_3$ | $CH_3$ | $CH_3$ | —O—C$(CH_3)_2$—O—$CH_2$— | | $C_2H_5$ | 1.05 (t, 3H), 1.39 (s, 6H), 2.38 (q, 2H), 3.34 (mc, 1H), 3.85 and 3.90 (in each case d, in each case 1H), 3.92 (mc, 1H) | syn/anti mixture |
| I-b-51 | $CH_3$ | $CH_3$ | $CH_3$ | —O—C$(CH_3)_2$—O—$CH_2$— | | C$(CH_3)_2$$CH_2$Cl | 90-91 | syn/anti mixture |
| I-b-52 | $CH_3$ | $CH_3$ | $CH_3$ | O= | | C$(CH_3)_2$$CH_2$Cl | 1.12 and 1.17 (in each case s, in each case 3H), 3.43 and 3.46 (in each case d, in each case 3H), 6.83 (s, 2H) | |
| I-b-53 | $CH_3$ | $CH_3$ | $CH_3$ | O= | | $H_3C$—O—$CH_2$— | 1.99, 2.09 and 2.25 (in each case s, in each case 3H), 3.30 (s, 3H), 3.51 (mc, 1H), 4.03 (s, 2H) | |
| I-b-54 | $CH_3$ | $CH_3$ | $CH_3$ | O= | | i-$C_3H_7$ | 1.04 and 1.07 (in each case d, in each case 3H), 2.56 (hept, 1H), 3.50 and 4.12 (in each case mc, in each case 1H) | |
| I-b-55 | $CH_3$ | $CH_3$ | $CH_3$ | O= | | —C$(CH_3)_2$$C_2H_5$ | 0.61 (t, 3H), 1.42 (q, 2H), 2.39-2.85 (m, 4H), 6.83 (s, 2H) | |
| I-b-56 | $CH_3$ | $CH_3$ | $CH_3$ | O= | | i-$C_4H_9$ | 0.80 (mc, 6H), 1.95 (hept, 1H), 2.40-2.85 (m, 4H) | |
| I-b-57 | $CH_3$ | $CH_3$ | $CH_3$ | O= | | $C_2H_5$ | 1.05 (t, 3H), 2.40 (q, 2H), 3.49 and 4.16 (in each case mc, in each case 1H) | |
| I-b-58 | $CH_3$ | $CH_3$ | $CH_3$ | =NOCH$_2$—C≡CH | | i-$C_3H_7$ | 1.02 and 1.11 (in each case d, in each case 3H), 2.41 (mc, 1H), 2.55-2.94 (m, 5H), 4.51 (mc, 2H) | |
| I-b-59 | $CH_3$ | $CH_3$ | $CH_3$ | =NOCH$_2$—C≡CH | | t-$C_4H_9$ | 1.09 (s, 9H), 2.42 (mc, 1H), 2.63-3.08 (m, 4H), 4.52 (mc, 1H) | |

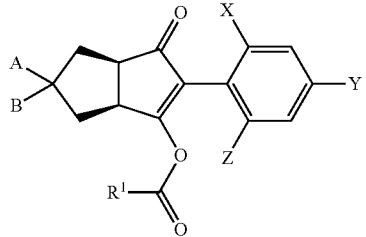

(I-b)

| Ex. No. | X | Y | Z | A | B | R¹ | M.p. [° C.] or ¹H-NMR (400 MHz, CDCl₃, δ in ppm) | Isomerism |
|---|---|---|---|---|---|---|---|---|
| I-b-60 | CH₃ | CH₃ | CH₃ | =O | | t-C₄H₉ | 1.08 (s, 9H), 1.99, 2.06 and 2.22 (in each case s, in each case 3H), 3.50 and 4.11 (in each case mc, in each case 1H) | |
| I-b-61 | OCH₃ | CH₃ | CH₃ | =O | | i-C₃H₇ | 1.10 (mc, 6h), 2.30 (s, 3H), 3.48 (mc, 1H), 3.68 (s, 3H), 4.12-4.28 (m, 1H) | |
| I-b-62 | OCH₃ | CH₃ | CH₃ | =CH₂ | | i-C₃H₇ | 1.10 (mc, 6H), 2.00 and 2.29 (in each case s, in each case 3H), 3.65 (s, 3H), 4.90 (mc, 2H) | |
| I-b-63 | OCH₃ | CH₃ | CH₃ | —O—CH₂—CH=CH—CH₂—O— | | i-C₃H₇ | 1.05-1.14 (m, 5H), 2.60 (hept, 1H), 3.68 and 3.70 (in each case s, Σ 3H), 5.63 (mc, 2H) | |
| I-b-64 | OCH₃ | CH₃ | CH₃ | —O—(CH₂)₃—O— | | i-C₃H₇ | 1.08-1.15 (m, 6H), 2.61 (hept, 1H), 3.66 (s, 3H), 6.50 and 6.63 (in each case s, in each case 1H) | |
| I-b-65 | OCH₃ | CH₃ | CH₃ | —O—(CH₂)₂—O— | | i-C₃H₇ | 1.10 (mc, 6H), 2.62 (hept, 1H), 3.68 s, 3H), 3.88 (mc, 4H) | |
| I-b-66 | C₂H₅ | CH₃ | CH₃ | —O—C(CH₃)₂—O—CH₂— | | CH₃ | 1.07 and 1.10 (in each case t, Σ6H), 1.40 (s, 6H), 2.05 and 2.06 (in each case s, in each case 3H), 3.84 and 3.88 (in each case d, in each case 1H) | anti |
| I-b-67 | C₂H₅ | CH₃ | CH₃ | —O—C(CH₃)₂—O—CH₂— | | C₂H₅ | 1.05 (mc, 3H), 1.10 (t, 3H), 2.05 and 2.28 (in each case s, in each case 3H), 2.34 (mc, 2H) | anti |
| I-b-68 | C₂H₅ | CH₃ | CH₃ | —O—C(CH₃)₂—O—CH₂— | | i-C₄H₉ | 0.79 (mc, 6H), 1.38 (s, 6H), 3.32 (mc, 1H), 3.85 (mc, 2H), 3.94 (mc, 1H) | anti |
| I-b-69 | C₂H₅ | CH₃ | CH₃ | —O—C(CH₃)₂—O—CH₂— | | i-C₃H₇ | 1.05 (mc, 6H), 1.39 (s, 6H), 2.55 (hept, 1H), 3.33 (mc, 1H), 3.89 (mc, 2H), 3.97 (mc, 1H) | anti |
| I-b-70 | C₂H₅ | CH₃ | CH₃ | —O—C(CH₃)₂—O—CH₂— | | t-C₄H₉ | 79-80 | anti |
| I-b-71 | C₂H₅ | CH₃ | CH₃ | O= | | t-C₄H₉ | 1.06 (s, 9H), 2.27 (s, 3H), 3.50 and 4.15 (in each case mc, in each case 1H) | |
| I-b-72 | C₂H₅ | CH₃ | CH₃ | CH₂= | | i-C₃H₇ | 0.95-1.10 (m, 9H), 2.26 (s, 3H), 2.52-2.70 (m, 4H), 4.90 (mc, 2H) | |
| I-b-73 | C₂H₅ | CH₃ | CH₃ | CH₂= | | t-C₄H₉ | 0.98 and 1.03 (in each case t, Σ 3H), 1.06 (s, 9H), 3.18 and 3.88 (in each case mc, in each case 1H), 4.91 (mc, 2H) | |
| I-b-74 | C₂H₅ | CH₃ | CH₃ | —O—(CH₂)₃—O— | | t-C₄H₉ | 1.08 (s, 9H), 2.25-2.33 (m, 1H), 3.15 (mc, 1H), 3.70-3.90 (m, 5H) | |
| I-b-75 | C₂H₅ | CH₃ | CH₃ | —O—CH₂—CH=CH—CH₂—O— | | t-C₄H₉ | 103-104 | |
| I-b-76 | C₂H₅ | CH₃ | CH₃ | —O—CH₂—CH=CH—CH₂—O— | | i-C₃H₇ | 84-85 | |
| I-b-77 | C₂H₅ | CH₃ | CH₃ | —O—(CH₂)₄—O— | | i-C₃H₇ | 101 | |
| I-b-78 | C₂H₅ | CH₃ | CH₃ | —O—(CH₂)₄—O— | | t-C₄H₉ | 119-120 | |
| I-b-79 | C₂H₅ | CH₃ | CH₃ | —O—(CH₂)₂—O— | | i-C₃H₇ | 1.06 (mc, 6H), 2.47 (hept, 1H), 3.19 (mc, 1H), 3.85-3.95 (m, 5H) | |

Example I-e-1

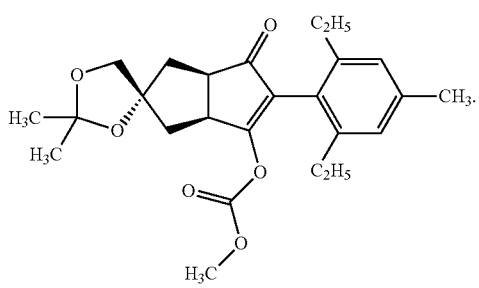

(I-c-1)

At room temperature, 82 mg (0.81 mmol) of triethylamine are added to 0.100 g (0.27 mmol) of the compound (I-a-1) according to the invention and 28 mg (0.30 mmol) of methyl chloroformate in 5 ml of dichloromethane, and the mixture is stirred for another 1 h. The reaction mixture is poured into ice-water, taken up in dichloromethane, washed with water, dried (magnesium sulphate), and the solvent is distilled off.

Chromatographic purification on silica gel (ethyl acetate/hexane v/v=20:80) gives 104 mg (90%) of the desired compound of the formula (I-c-1) in the form of colourless crystals of melting point 111-112° C.

Example I-c-17

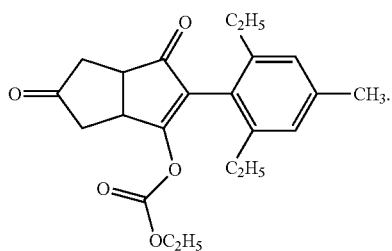

0.98 ml of 2.5% strength solution of osmium tetroxide in n-butanol is added to 1.50 g (4.05 mmol) of 2-(2,6-diethyl-4-methylphenyl)-5-methylidene-3-oxo-3,3a,4,5,6,6a-hexahydropentalen-1-yl ethyl carbonate (Example I-c-5) and 4.33 g (20.24 mmol) of sodium meta-periodate in 150 ml of a water/tert-butanol mixture (v/v=50:50), and the mixture is stirred at room temperature for 10 minutes. 50 ml of ethyl acetate are then added, and the mixture is stirred at room temperature for another 2 h.

The reaction mixture is poured onto ice, taken up in ethyl acetate and extracted with water. After drying (magnesium sulphate) and distillative removal of the solvent, the residue is chromatographed on silica gel using ethyl acetate/hexane (v/v=30:70). This gives 1.00 g (66%) of the desired compound of the formula (I-c-17) as a viscose oil.

$^1$H-NMR (400 MHz, CDCl$_3$): δ=1.26 (t, 3H), 3.51 and 4.31 (in each case mc, in each case 1H), 4.20 (mc, 2H) ppm The following compounds of the formula (I-c) are obtained analogously to Examples (I-c-1) and (I-c-17) and in accordance with the general statements on the preparation:

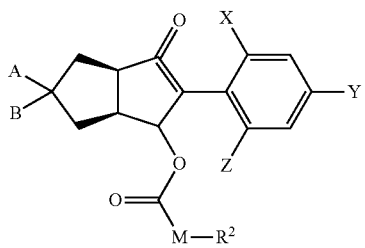

(I-c)

| Ex. No. | X | Y | Z | A B | M | R$^2$ | M.p. [° C.] or $^1$H-NMR (400 MHz, CDCl$_3$, δ in ppm) | Isomerism |
|---|---|---|---|---|---|---|---|---|
| I-c-2 | C$_2$H$_5$ | CH$_3$ | C$_2$H$_5$ | —O—C(CH$_3$)$_2$—O—CH$_2$— | O | i-C$_3$H$_7$ | δ = 1.21 (d, 6 H), 1.88 and 1.98 (in each case mc, in each case 1 H), 3.89 (dd, 2 H), 4.81 (quint, 1H) | anti |
| I-c-3 | C$_2$H$_5$ | CH$_3$ | C$_2$H$_5$ | —O—C(CH$_3$)$_2$—O—CH$_2$— | O | i-C$_3$H$_7$ | δ = 1.32 (d, 6 H), 1.92-2.13 (m, 3 H), 3.92 (dd, 2H), 4.83 (quint, 1 H) | syn |
| I-c-4 | C$_2$H$_5$ | CH$_3$ | C$_2$H$_5$ | —O—C(CH$_3$)$_2$—O—CH$_2$— | O | CH$_3$ | 132-133 | syn |
| I-c-5 | C$_2$H$_5$ | CH$_3$ | C$_2$H$_5$ | =CH$_2$ | O | C$_2$H$_5$ | δ = 1.26 (t, 3H), 3.20 (mc, 1 H), 4.02 (mc, 1H), 4.82 (mc, 2 H). | |
| I-c-6 | C$_2$H$_5$ | CH$_3$ | C$_2$H$_5$ | —O—CH$_2$—C(CH$_3$)$_2$—CH$_2$—O— | O | C$_2$H$_5$ | 125-126 | |
| I-c-7 | C$_2$H$_5$ | CH$_3$ | C$_2$H$_5$ | —O—(CH$_2$)$_2$—O— | O | C$_2$H$_5$ | δ = 1.08, 1.09 and 1.22 (in each case t, in each case 3H), 3.20 (mc, 1 H), 3.89 (mc, 4 H), 4.04 (mc, 1H), 4.19 (mc, 2H) | |
| I-c-8 | C$_2$H$_5$ | CH$_3$ | C$_2$H$_5$ | —O—CHCH$_3$—CH$_2$—O— | O | C$_2$H$_5$ | 79 | syn/anti mixture |
| I-c-9 | C$_2$H$_5$ | CH$_3$ | C$_2$H$_5$ | —O—(CH$_2$)$_4$—O— | O | C$_2$H$_5$ | 113 | |
| I-c-10 | C$_2$H$_5$ | CH$_3$ | C$_2$H$_5$ | —O—CHCH$_3$—CH$_2$—CHCH$_3$—O— | O | C$_2$H$_5$ | δ = 1.02-1.28 (m, 15 H), 3.20 (mc, 1H), 3.80-4.01 (m, 3 H), 4.18 (mc, 2H) | Isomer mixture with CH$_3$-groups at the acetal ring |
| I-c-11 | C$_2$H$_5$ | CH$_3$ | C$_2$H$_5$ | —O—CH$_2$—CH=CH—CH$_2$—O— | O | C$_2$H$_5$ | δ = 1.08. 1.12 and 1.24 (in each case t, in each case 3 H), 4.01-4.32 (m, 7 H), 5.65 (s, 2 H) | |
| I-c-12 | C$_2$H$_5$ | CH$_3$ | C$_2$H$_5$ | —O—CH$_2$—C(=CH$_2$)—CH$_2$—O— | O | C$_2$H$_5$ | 119 | |
| I-c-13 | C$_2$H$_5$ | CH$_3$ | C$_2$H$_5$ | —O—CH(CH$_3$)—CH$_2$—CH(CH$_3$)O— | O | C$_2$H$_5$ | δ = 1.05-1.25 (m, 15H), 3.20 and 3.92 (in each case mc, in each case 1 H), 4.00 (mc, 2H), 4.18 (mc, 2 H) | (R,R)-Configuration of the CH$_3$-groups at the acetal ring |
| I-c-14 | C$_2$H$_5$ | CH$_3$ | C$_2$H$_5$ | —O—(CH$_2$)$_3$—O— | O | C$_2$H$_5$ | 110 | |
| I-c-15 | C$_2$H$_5$ | CH$_3$ | C$_2$H$_5$ | —S—(CH$_2$)$_2$—S— | O | C$_2$H$_5$ | δ = 1.25 (t, 3H), 2.61 (mc, 2H), 3.35 (mc, 5H), 4.19 (mc, 3H), 6.90 (s, 2H) | |
| I-c-16 | C$_2$H$_5$ | CH$_3$ | C$_2$H$_5$ | —S—(CH$_2$)$_3$—S— | O | C$_2$H$_5$ | δ = 1.26 (t, 3H), 2.83 (mc, 3H), 2.93 (mc, 3H), 4.20 (mc, 2H), 4.22 (mc, 1H) | |
| I-c-17 | C$_2$H$_5$ | CH$_3$ | C$_2$H$_5$ | =O | O | C$_2$H$_5$ | 1.26 (t, 3 H), 3.51 and 4.31 (in each case mc, in each case 1 H), 4.20 (mc, 2H) | |

-continued

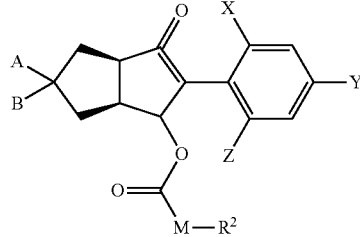

(I-c)

| Ex. No. | X | Y | Z | A B | M | R² | M.p. [° C.] or ¹H-NMR (400 MHz, CDCl₃, δ in ppm) | Isomerism |
|---|---|---|---|---|---|---|---|---|
| I-c-18 | C₂H₅ | CH₃ | C₂H₅ | —O—C(CH₃)₂—C(CH₃)₂—O— | O | C₂H₅ | 116-117 | |
| I-c-19 | C₂H₅ | CH₃ | C₂H₅ | —S—(CH₂)₃—O— | O | C₂H₅ | 1.24 (t, 3H), 3.00 (mc, 2H), 3.72 (mc, 2H), 4.18 (mc, 1H) | syn/anti mixture |
| I-c-20 | C₂H₅ | CH₃ | C₂H₅ | —S—(CH₂)₃—S— | O | CH₃ | 2.62 (mc, 1H), 2.80-2.98 (m, 5H), 3.49 (mc, 1H), 3.78 (s, 1H), 4.23 (mc, 1H) | |
| I-c-21 | C₂H₅ | CH₃ | C₂H₅ | —O—CH₂—CH=CH—CH₂—O— | O | CH₃ | 1.08 and 1.12 (in each case t, in each case 3H), 3.75 (s, 3H), 4.02 (mc, 2H), 4.16-4.32 (m, 3H), 5.67 (s, 2H) | |
| I-c-22 | C₂H₅ | CH₃ | C₂H₅ | —O—CH₂—C(CH₃)₂—CH₂—O— | O | C₂H₅ | 98-99 | |
| I-c-23 | C₂H₅ | CH₃ | C₂H₅ | —O—CH₂—C(CH₃)₂—CH₂—O— | O | CH₃ | 126-127 | |
| I-c-24 | C₂H₅ | CH₃ | C₂H₅ | —O—CH(CH₃)—CH₂—CH(CH₃)O— | O | CH₃ | 1.03-1.22 (m, 12H), 3.20 (mc, 1H), 3.75 (doubled singlet, Σ 3H), 3.90-4.02 (m, 3H) | (R,R)-Configuration of the CH₃-groups at the acetal ring |
| I-c-25 | C₂H₅ | CH₃ | C₂H₅ | —O—CH₂—C(OCH₃)—CH₂—O— | O | C₂H₅ | 1.23 (t, 3H), 2.70-2.79 (m, 1H), 4.19 (mc, 2H), 3.10 (mc, 1H), 3.38 (s, 3H) | |
| I-c-26 | C₂H₅ | CH₃ | C₂H₅ | —O—CH₂CH(OC₂H₅)CH₂—O— | O | C₂H₅ | 1.03-1.28 (m, 12H); 3.20 and 3.39 (in each case mc, in each case 1H), 3.95-4.05 (m, 2H), 4.11-4.25 (m, 3H) | |
| I-c-27 | C₂H₅ | CH₃ | C₂H₅ | —OCH₂—CH(OC₂H₅)CH₂—O— | O | CH₃ | 1.00-1.21 (m, 12H), 3.76 (s, 3H), 3.92-4.05 (m, 2H), 4.21 (mc, 1H) | |
| I-c-28 | C₂H₅ | CH₃ | C₂H₅ | —OCH₂—CH(OCH₂C₆H₅)CH₂—O— | O | C₂H₅ | 1.22 (t, 3H), 2.95 (mc, 2H), 4.15 (mc, 2H), 4.55 (s, 2H), 6.88 and 6.91 (in each case s, in each case 1H), 7.27-7.85 (m, 5H) | |
| I-c-29 | C₂H₅ | CH₃ | C₂H₅ | —OCH₂—CH(OCH₂C₆H₅)CH₂—O— | O | CH₃ | 2.05-2.12 (m, 2H), 3.41 (mc, 1H), 3.74 (s, 3H), 4.60 (s, 2H), | |
| I-c-30 | C₂H₅ | CH₃ | C₂H₅ | —S—(CH₂)₂—O— | O | C₂H₅ | 94-95 | syn/anti mixture |
| I-c-31 | C₂H₅ | CH₃ | C₂H₅ | —S—(CH₂)₂—O— | O | CH₃ | 3.00 (mc, 2H), 3.77 (s, 3H), 3.96 (mc, 1H), 4.02-4.10 (m, 2H) | syn/anti mixture |
| I-c-32 | C₂H₅ | CH₃ | C₂H₅ | —S—(CH₂)₃—O— | O | CH₃ | 2.95-3.05 (m, 2H), 3.25 (mc, 1H), 3.72 (mc, 2H), 3.75 (s, 3H), 4.08 (mc, 1H) | syn/anti mixture |
| I-c-33 | C₂H₅ | CH₃ | C₂H₅ | —S—(CH₂)₂—O— | O | i-C₃H₇ | 1.23 (6H), 3.01 (mc, 2H), 4.08 (mc, 2H), 4.81 (mc, 1H) | syn/anti mixture |
| I-c-34 | C₂H₅ | CH₃ | C₂H₅ | —O—(CH₂)₃—O— | O | i-C₃H₇ | 1.22 (mc, 6H), 3.18 (mc, 1H), 3.79 (mc, 2H), 3.88 (mc, 2H), 3.99, (mc, 1H), 4.81 (hept, 1H) | |
| I-c-35 | C₂H₅ | CH₃ | C₂H₅ | —O—(CH₂)₃—O— | O | CH₃ | 2.00-2.12 (m, 2H), 3.19 (mc, 1H), 3.73 (s, 3H), 3.88 (mc, 1H), 3.99 (mc, 1H) | |
| I-c-36 | C₂H₅ | CH₃ | C₂H₅ | —O—(CH₂)₂—O— | O | i-C₃H₇ | 110-111 | |
| I-c-37 | C₂H₅ | CH₃ | C₂H₅ | —O—(CH₂)₂—O— | O | CH₃ | 116 | |
| I-c-38 | C₂H₅ | CH₃ | C₂H₅ | =NOtC₄H₉ | O | C₂H₅ | 1.24 (s, 9H), 1.28 (mc, 3H), 2.62-2.90 (m, 4H), 4.15 (mc, 1H), 4.20 (mc, 2H) | |
| I-c-39 | C₂H₅ | CH₃ | C₂H₅ | =NOi-C₃H₇ | O | C₂H₅ | 1.03 (mc, 6H), 1.15-1.30 (m, 9H), 2.35 (hept, 2H), 3.32 (mc, 1H), 4.20 (mc, 2H), 4.25 (mc, 1H) | |
| I-c-39 | C₂H₅ | CH₃ | C₂H₅ | =NOCyclopentyl | O | C₂H₅ | 1.52-1.80 (m, 8H), 3.30 (mc, 1H), 4.12-4.22 (m, 3H), 4.62 (mc, 1H) | |
| I-c-40 | C₂H₅ | CH₃ | C₂H₅ | =NOCH₂-cyclopropyl | O | C₂H₅ | 0.23 and 0.51 (in each case mc, in each case 2H), 3.19-3.49 (m, 1H), 3.82 (mc, 2H), 4.12-4.24 (m, 3H) | |
| I-c-41 | C₂H₅ | CH₃ | C₂H₅ | =NOCH₂C≡CH | O | C₂H₅ | 1.25 (mc, 3H), 2.47 (mc, 1H), 4.15-4.25 (m, 3H), 4.61 (d, 2H) | |
| I-c-42 | C₂H₅ | CH₃ | C₂H₅ | O= | O | CH₃ | 2.60-2.85 (m, 3H), 3.51 (mc, 1H), 3.79 (s, 3H), 4.30 (mc, 1H) | |
| I-c-43 | C₂H₅ | CH₃ | C₂H₅ | =NOCH(CH₃)—C≡CH | O | C₂H₅ | 1.28 (t, 3H), 1.48 (mc, 3H), 2.43 (mc, 1H), 3.34 (mc, 1H), 4.80 (mc, 1H) | |
| I-c-44 | CH₃ | CH₃ | CH₃ | —O—(CH₂)₂—O— | O | C₂H₅ | 1.21 (t, 3H), 2.05, 2.12 and 2.22 (in each case s, in each case 3H), 3.19 (mc, 1H), 3.89 (mc, 4H), 3.91 (mc, 1H), 4.12 (mc, 2H) | |
| I-c-45 | CH₃ | CH₃ | CH₃ | CH₂= | O | C₂H₅ | 1.21 (t, 3H), 1.98, 2.06 and 2.24 (in each case s, in each case 3H), 4.15 (mc, 2H), 4.90 (mc, 2H) | |

-continued

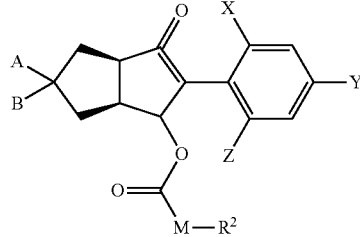

(I-c)

| Ex. No. | X | Y | Z | A B | M | R² | M.p. [° C.] or ¹H-NMR (400 MHz, CDCl₃, δ in ppm) | Isomerism |
|---|---|---|---|---|---|---|---|---|
| I-c-46 | CH₃ | CH₃ | CH₃ | CH₂= | O | CH₃ | 1.99, 2.05 and 2.22 (in each case s, in each case 3H), 2.40-2.72 (m, 4H), 3.72 (s, 3H), 4.90 (mc, 2H) | |
| I-c-47 | CH₃ | CH₃ | CH₃ | —O—(CH₂)₃—O— | O | C₂H₅ | 1.20 (t, 3H), 2.80 (mc, 1H), 3.16 (mc, 1H), 3.70-3.90 (m, 5H), 4.12 (mc, 2H) | |
| I-c-48 | CH₃ | CH₃ | CH₃ | —O—CH₂—CH(CH₃)—CH₂—O— | O | C₂H₅ | 0.71 and 0.82 (in each case d, Σ 3H), 2.45-2.50 (m, 1H), 3.28-3.45 (m, 2H), 4.12 (mc, 2H) | |
| I-c-49 | CH₃ | CH₃ | CH₃ | —O—(CH₂)₄—O— | O | CH₃ | 122 | |
| I-c-50 | CH₃ | CH₃ | CH₃ | —O—(CH₂)₄—O— | O | C₂H₅ | 131 | |
| I-c-51 | CH₃ | CH₃ | CH₃ | —O—CH₂—CH=CH—CH₂—O— | O | C₂H₅ | 1.21 (t, 3H), 4.00-4.31 (m, 6H), 5.65 (mc, 2H), 6.85 (mc, 2H) | |
| I-c-52 | CH₃ | CH₃ | CH₃ | —O—CH₂—CH=CH—CH₂—O— | O | CH₃ | 3.70 (s, 3H), 3.94 (mc, 1H), 3.96-4.30 (m, 4H), 5.64 (mc, 2H) | |
| I-c-53 | CH₃ | CH₃ | CH₃ | —O—CH₂—CH(CH₃)—CH₂—O— | O | CH₃ | 0.70 and 0.82 (in each case t, Σ 3H), 2.48 (mc, 1H), 3.15 (mc, 1H), 3.29-3.45 (m, 2H), 3.71 (s, 3H) | |
| I-c-54 | CH₃ | CH₃ | CH₃ | —O—C(CH₃)₂—O—CH₂— | O | C₂H₅ | 1.20 (t, 3H), 1.48 (s, 6H), 3.34 (mc, 1H), 3.85 and 3.89 (in each case d, in each case 1H), 4.12 (q, 2H) | syn/anti mixture |
| I-c-55 | CH₃ | CH₃ | CH₃ | —O—C(CH₃)₂—O—CH₂— | O | i-C₃H₇ | 1.15 and 1.19 (in each case d, Σ 6H), 1.38 (s, 6H), 3.85 and 3.90 (in each case d, in each case 1H), 4.72 (hept, 1H) | syn/anti mixture |
| I-c-56 | CH₃ | CH₃ | CH₃ | —O—C(CH₃)₂—O—CH₂— | O | CH₃ | 1.38 (s, 6H), 3.36 (mc, 1H), 3.71 (s, 3H), 4.00 (mc, 1H) | syn/anti mixture |
| I-c-57 | CH₃ | CH₃ | CH₃ | =O | O | CH₃ | 1.98, 2.10 and 2.26 (in each case s, in each case 3H), 3.50 (mc, 1H), 3.75 (s, 3H), 4.19 (mc, 1H) | |
| I-c-58 | CH₃ | CH₃ | CH₃ | =O | O | C₂H₅ | 1.22 (t, 3H), 2.00, 2.11 and 2.26 (in each case s, in each case 3H), 2.42-2.85 (m, 4H), 4.10-4.22 (3H), | |
| I-c-59 | CH₃ | CH₃ | CH₃ | =NOCH₂C≡CH | O | CH₃ | 2.45 (mc, 1H), 2.70-3.08 (m, 4H), 3.75 (s, 3H), 4.61 (mc, 2H), | |
| I-c-60 | CH₃ | CH₃ | CH₃ | =NOCH₂C≡CH | O | C₂H₅ | 1.23 (mc, 3H), 2.44 (mc, 1H), 2.70-3.08 (m, 4H), 4.18 (mc, 2H), 4.61 (mc, 2H) | |
| I-c-61 | OCH₃ | CH₃ | CH₃ | CH₂= | O | C₂H₅ | 2.30 (s, 3H), 2.39-2.70 (m, 4H), 3.70 (s, 3H), 4.18 (mc, 2H) | |
| I-c-62 | OCH₃ | CH₃ | CH₃ | CH₂= | O | CH₃ | 2.38-2.70 (m, 4H), 3.70 and 3.75 (in each case s, in each case 1H), 4.89 (mc, 2H) | |
| I-c-62 | OCH₃ | CH₃ | CH₃ | O= | O | C₂H₅ | 1.25 (mc, 3H), 2.30 (s, 3H), 2.40-2.85 (m, 4H), 3.50 (mc, 1H), 4.10 (mc, 2H) | |
| I-c-63 | OCH₃ | CH₃ | CH₃ | —O—(CH₂)₃—O— | O | C₂H₅ | 1.22 (t, 3H), 2.09 and 2.29 (in each case s, in each case 3H), 2.76-2.80 (m, 1H), 3.18 (mc, 1H), 3.70 (s, 3H) | |
| I-c-64 | OCH₃ | CH₃ | CH₃ | —O—(CH₂)₂—O— | O | C₂H₅ | 21.12 and 2.30 (in each case s, in each case 3H), 3.70 (s, 3H), 3.85 (mc, 4H), 4.18 (q, 2H) | |
| I-c-65 | OCH₃ | CH₃ | CH₃ | —O—CH₂—CH=CH—CH₂—O— | O | C₂H₅ | 1.25 (t, 3H), 3.70 (s, 3H), 3.86-430 (m, 7H), 5.64 (mc, 2H) | |
| I-c-66 | OCH₃ | CH₃ | CH₃ | —O—(CH₂)₄—O— | O | C₂H₅ | 1.22 (t, 3H), 2.22 and 2.30 (in each case s, in each case 3H), 3.12 (mc, 1H), 3.70 (s, 3H), 4.16 (q, 2H) | |
| I-c-67 | OCH₃ | CH₃ | C₂H₅ | CH₂= | O | C₂H₅ | 0.99 and 1.08 (in each case t, Σ 3H), 1.26 (mc, 3H), 3.61 and 3.68 (in each case s, Σ 3H), 4.89 (mc, 2H). | |
| I-c-68 | OCH₃ | CH₃ | C₂H₅ | O= | O | C₂H₅ | 1.05 and 1.11 (in each case t, Σ 3H), 1.26 (mc, 3H), 2.25-2.83 (m, 4H), 2.30 (s, 3H), 4.20 (mc, 2H) | |

-continued

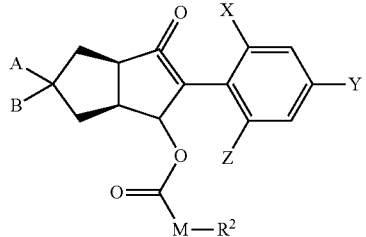

(I-c)

| Ex. No. | X | Y | Z | A B | M | R² | M.p. [° C.] or ¹H-NMR (400 MHz, CDCl₃, δ in ppm) | Isomerism |
|---|---|---|---|---|---|---|---|---|
| I-c-69 | OCH₃ | CH₃ | C₂H₅ | —O—(CH₂)₂—O— | O | C₂H₅ | 1.09 (t, 3H), 1.24 (t, 3H), 2.31 (s, 3H), 3.70 (s, 3H), 3.88 (mc, 4H), 4.19 (q, 2H) | |
| I-c-70 | OCH₃ | CH₃ | C₂H₅ | —O—(CH₂)₃—O— | O | C₂H₅ | 1.10 and 1.15 (in each case t, in each case 3H), 3.70 (s, 3H), 3.70-4.00 (m, 4H), 4.18 (q, 2H) | |
| I-c-71 | C₂H₅ | CH₃ | CH₃ | —O—(CH₂)₂—O— | O | C₂H₅ | 1.08 and 1.22 (in each case t, in each case 3H), 3.88 (mc, 4H), 3.96 (mc, 1H), 4.15 (mc, 2H) | |
| I-c-72 | C₂H₅ | CH₃ | CH₃ | —O—CH₂—CH=CH—CH₂—O— | O | C₂H₅ | 124-125 | |
| I-c-73 | C₂H₅ | CH₃ | CH₃ | —O—CH₂—CH=CH—CH₂—O— | O | CH₃ | 1.08 (t, 3H), 3.18 (mc, 1H), 3.71 (s, 3H), 3.95-4.31 (m, 5H), 5.65 (mc, 2H) | |
| I-c-74 | C₂H₅ | CH₃ | CH₃ | —O—CH₂—CH=CH—CH₂—O— | O | i-C₃H₇ | 1.20 (mc, 6H), 3.91-4.32 (m, 5H), 4.79 (hept, 1H), 5.64 (mc, 2H) | |
| I-c-75 | C₂H₅ | CH₃ | CH₃ | —O—(CH₂)₄—O— | O | C₂H₅ | 102 | |
| I-c-76 | C₂H₅ | CH₃ | CH₃ | CH₂= | O | C₂H₅ | 0.96 and 1.08 (in each case t, Σ 3H), 1.22 (t, 3H), 2.26 (s, 3H), 4.15 (mc, 2H), 4.91 (mc, 1H) | |
| I-c-77 | C₂H₅ | CH₃ | CH₃ | CH₂= | O | CH₃ | 0.97 and 1.05 (in each case t, Σ 3H), 3.75 (s, 3H), 4.92 (mc, 2H) | |
| I-c-78 | C₂H₅ | CH₃ | CH₃ | —O—C(CH₃)₂—O—CH₂— | O | i-C₃H₇ | 116-117 | syn/anti mixture |
| I-c-79 | C₂H₅ | CH₃ | CH₃ | —O—C(CH₃)₂—O—CH₂— | O | CH₃ | 1.02-1.11 (m, 3H), 1.38 (s, 6H), 3.74 (s, 3H), 3.85 and 3.88 (in each case d, in each case 1H) | syn/anti mixture |
| I-c-80 | C₂H₅ | CH₃ | CH₃ | —O—C(CH₃)₂—O—CH₂— | O | C₂H₅ | 1.20 (t, 3H), 1.38 (s, 6H), 2.30 (s, 3H), 3.86 and 4.00 (in each case d, in each case 1H), 4.15 (mc, 2H) | syn/anti mixture |
| I-c-81 | C₂H₅ | C₂H₅ | C₂H₅ | CH₂= | O | C₂H₅ | 0.98 and 1.07 (in each case t, in each case 3H), 1.22-1.29 (m, 6H), 4.20 (mc, 2H), 4.92 (mc, 2H) | |
| I-c-82 | C₂H₅ | C₂H₅ | C₂H₅ | O= | O | C₂H₅ | 103 | |
| I-c-83 | C₂H₅ | C₂H₅ | C₂H₅ | —O—(CH₂)₃—O— | O | C₂H₅ | 122 | |
| I-c-84 | C₂H₅ | C₂H₅ | C₂H₅ | —O—(CH₂)₂—O— | O | C₂H₅ | 98 | |
| I-c-85 | C₂H₅ | CH₃ | H | —O—(CH₂)₃—O— | O | C₂H₅ | | |
| I-c-86 | C₂H₅ | CH₃ | H | —O—(CH₂)₃—O— | O | CH₃ | | |
| 1-c-87 | C₂H₅ | CH₃ | H | —O—(CH₂)₄—O— | O | C₂H₅ | | |
| I-c-88 | C₂H₅ | CH₃ | H | —O—(CH₂)₂—O— | O | C₂H₅ | | |
| I-c-89 | C₂H₅ | CH₃ | C₂H₅ | —O—CH(CH₃)—CH₂—CH₂—O— | O | C₂H₅ | 1.05-1.28 (m, 12H), 2.32 (s, 3H), 3.70-4.05 (m, 4H), 4.18 (mc, 2H) | syn/anti mixture |

Example I-d-1

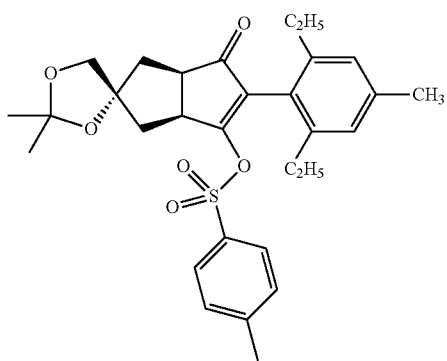

(I-d-1)

At room temperature, 57 mg (0.29 mmol) of p-toluenesulphonyl chloride and 0.1 ml of triethylamine are added to 100 mg (0.27 mmol) of the compound (I-a-1) in 5 ml of dichlormethane. After 1 h of stirring, the mixture is diluted with water and the organic phase is separated off and washed twice with 1 N hydrochloric acid. Drying with magnesium sulphate and distillative removal of the solvent affords 120 mg (87%) of the desired substance as a colourless oil.

¹H-NMR (400 MHz, CDCl₃): δ=0.98 and 1.03 (in each case t, in each case 3H), 2.30 and 2.39 (in each case s, in each case 1H), 3.15 and 3.90 (in each case mc, in each case 1H), 3.98-4.35 (m, 4H), 5.65 (s, 2H) ppm.

The following compounds of the formula (I-d) are obtained analogously to Example (I-d-1) and in accordance with the general statements on the preparation:

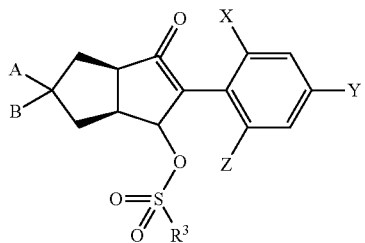

(I-d)

| Ex. No. | X | Y | Z | A B | R³ | M.p. [° C.] or ¹H-NMR (400 MHz, d₆-DMSO, δ in ppm) | Isomerism |
|---|---|---|---|---|---|---|---|
| I-d-2 | $C_2H_5$ | $CH_3$ | $C_2H_5$ | —O—C(CH₃)₂—O—CH₂— | $C_6H_5$ | 1.40 (s, 6H), 3.85 and 3.88 (in each case d, in each case 1H), 7.39 (mc, 2H), 7.61 (mc, 3H) | anti |
| I-d-3 | $C_2H_5$ | $CH_3$ | $C_2H_5$ | —O—C(CH₃)₂—O—CH₂— | $CH_3$ | 1.12 (t, 3H), 1.40 (s, 6H), 2.78 (s, 3H), 3.41 (mc, 1H), 3.88 and 3.91 (in each case d, in each case 1H), 3.93 (mc, 1H) | anti |
| I-d-4 | $CH_3$ | $CH_3$ | $CH_3$ | —O—C(CH₃)₂—O—CH₂— | $CH_3$ | 54-55 | syn/anti mixture |
| I-d-5 | $CH_3$ | $CH_3$ | $CH_3$ | —O—C(CH₃)₂—O—CH₂— | $C_6H_5$ | 140 | syn/anti mixture |
| I-d-6 | $CH_3$ | $CH_3$ | $CH_3$ | —O—C(CH₃)₂—O—CH₂— | $pCH_3C_6H_5$ | 144-145 | syn/anti mixture |
| I-d-7 | $C_2H_5$ | $CH_3$ | $C_2H_5$ | —O—CH₂—CH=CH—CH₂—O— | $CH_3$ | 133-134 | |
| I-d-8 | $C_2H_5$ | $CH_3$ | $C_2H_5$ | —O—CH₂—CH=CH—CH₂—O— | $C_6H_5$ | 129-130 | |
| I-d-9 | $C_2H_5$ | $CH_3$ | $C_2H_5$ | —O—CH₂—CH=CH—CH₂—O— | $pCH_3C_6H_5$ | 121-122 | |
| I-d-10 | $C_2H_5$ | $CH_3$ | $C_2H_5$ | —O—(CH₂)₂—O— | $CH_3$ | 146-147 | |
| I-d-11 | $C_2H_5$ | $CH_3$ | $C_2H_5$ | —O—(CH₂)₂—O— | $C_6H_5$ | 145-146 | |
| I-d-12 | $C_2H_5$ | $CH_3$ | $C_2H_5$ | —O—(CH₂)₂—O— | $pCH_3C_6H_5$ | 80 | |
| I-d-13 | $C_2H_5$ | $CH_3$ | $C_2H_5$ | =NOCH₂C≡CH | $CH_3$ | 143-144 | |
| I-d-14 | $C_2H_5$ | $CH_3$ | $C_2H_5$ | =NOCH₂C≡CH | $C_6H_5$ | | |
| I-d-15 | $C_2H_5$ | $CH_3$ | $C_2H_5$ | =NOCH₂C≡CH | $pCH_3C_6H_5$ | 2.30 and 2.42 (in each case s, in each case 3H), 2.45 (t, 1H), 3.99-4.08 (m, 1H), 4.60 (mc, 2H), 7.21 (d, 2H), 7.54 (d, 2H) | |

Example I-f-1

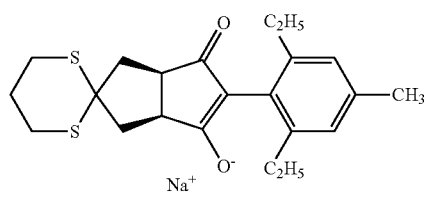

(I-f-1)

0.040 g (0.242 mmol) of sodium methoxide are added to 0.094 g (0.242 mmol) of the compound (I-a-17) in 3 ml of absolute methanol, and the mixture is stirred at room temperature for another 30 min.

Distillative removal of the solvent gives 0.096 g (96%) of the compound of the formula (I-f-1) according to the invention in the form of colourless crystals of melting point >300° C.

¹H-NMR (400 MHz, d₆-DMSO): δ=0.92 and 0.95 (in each case t, in each case 3H), 2.22 (s, 3H), 6.68 (mc, 2H) ppm The following compounds of the formula (I-f) are obtained analogously to Example (I-f-1) and in accordance with the general statements on the preparation:

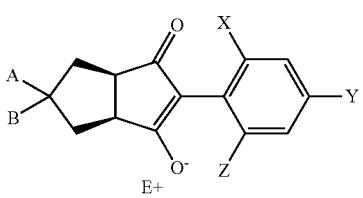

(I-f)

| Ex. No. | X | Y | Z | A B | E | M.p. [° C.] or ¹H-NMR (400 MHz, d₆-DMSO, δ in ppm) | Isomerism |
|---|---|---|---|---|---|---|---|
| I-f-2 | $C_2H_5$ | $CH_3$ | $C_2H_5$ | —O—CH(CH₃)—CH₂—CH(CH₃)—O— | Na⁺ | δ = 1.12 (d, 6H), 3.91 (mc, 2H), 6.68 (s, 2H) | (R,R)-Configuration of the CH₃-groups at the acetal ring |
| I-f-3 | $CH_3$ | $CH_3$ | $CH_3$ | —O—CH(CH₃)—CH₂—CH(CH₃)—O— | Na⁺ | 1.22 (s, 6H), 1.95, 2.00 and 2.12 (in each case s, in each case 3H) | (R,R)-Configuration of the CH₃-groups at the acetal ring |

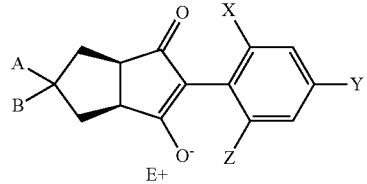

(I-f)

| Ex. No. | X | Y | Z | A B | E | M.p. [° C.] or $^1$H-NMR (400 MHz, $d_6$-DMSO, δ in ppm) | Isomerism |
|---|---|---|---|---|---|---|---|
| I-f-4 | OCH$_3$ | CH$_3$ | CH$_3$ | —O—(CH$_2$)$_3$—O— | Na$^+$ | 6.42 and 4.46 (in each case s, in each case 1H) | |
| I-f-5 | OCH$_3$ | CH$_3$ | CH$_3$ | —O—(CH$_2$)$_4$—O— | Na$^+$ | 6.42 (s, 1H), 6.48 (s, 1H) | |
| I-f-6 | OCH$_3$ | CH$_3$ | CH$_3$ | —O—(CH$_2$)$_2$—O— | Na$^+$ | 3.52 (s, 1H), 6.42 (s, 1H), 6.45 (s, 1H) | |
| I-f-7 | OCH$_3$ | CH$_3$ | CH$_3$ | —O—CH$_2$—CH=CH—CH$_2$—O— | Na$^+$ | 6.43 and 6.47 (in each case s, in each case 1H) | |
| I-f-8 | CH$_3$ | CH$_3$ | CH$_3$ | —O—CH$_2$—CH=CH—CH$_2$—O— | Na$^+$ | 5.61 (s, 2H), 6.62 (s, 2H) | |
| I-f-9 | CH$_3$ | CH$_3$ | CH$_3$ | —O—CH$_2$—CH(CH$_3$)—CH$_2$—O— | Na$^+$ | 0.70 (d, 3H), 3.61 and 3.72 (in each case mc, in each case 2H, 6.62 (s, 2H) | |
| I-f-10 | CH$_3$ | CH$_3$ | CH$_3$ | —O—(CH$_2$)$_4$—O— | Na$^+$ | 3.48 and 3.55 (in each case mc, in each case 2H), 6.62 (s, 2H) | |
| I-f-11 | CH$_3$ | CH$_3$ | CH$_3$ | —O—(CH$_2$)$_2$—O— | Na$^+$ | 2.00 (s, 6H), 2.15 (s, 3H), 3.75 (mc, 4H), 6.62 (s, 2H) | |
| I-f-12 | C$_2$H$_5$ | CH$_3$ | C$_2$H$_5$ | —O—CH$_2$—CH=CH—CH$_2$—O— | Na$^+$ | 0.93 (t, 6H), 2.33 (q, 4H), 5.62 (s, 2H), 6.68 (s, 2H) | |
| I-f-13 | C$_2$H$_5$ | CH$_3$ | C$_2$H$_5$ | —O—CH$_2$—CH(OCH$_3$)—CH$_2$—O— | Na$^+$ | 0.91 (t, 6H), 3.25 (s, 3H), 3.55 and 3.62 (in each case mc, in each case 1H), 6.66 (s, 2H) | |
| I-f-14 | C$_2$H$_5$ | CH$_3$ | C$_2$H$_5$ | —O—CH$_2$—CH(OC$_2$H$_5$)—CH$_2$—O— | Na$^+$ | 168-169 | |
| I-f-15 | C$_2$H$_5$ | CH$_3$ | C$_2$H$_5$ | —O—(CH$_2$)$_2$—O— | Na$^+$ | 0.95 (mc, 6H), 1.70 and 1.88 (in each case mc, in each case 2H), 3.78 (mc, 4H), 6.68 (mc, 2H) | |
| I-f-16 | C$_2$H$_5$ | CH$_3$ | C$_2$H$_5$ | —O—CH$_2$—CH(OCH$_2$C$_6$H$_5$)—CH$_2$—O— | Na$^+$ | 4.52 (s, 2H), 6.55 (s, 2H), 7.25-7.37 (m, 5H) | |
| I-f-17 | C$_2$H$_5$ | CH$_3$ | C$_2$H$_5$ | —O—(CH$_2$)$_4$—O— | Na$^+$ | 288-289 | |
| I-f-18 | C$_2$H$_5$ | CH$_3$ | C$_2$H$_5$ | —O—CH(CH$_3$)—CH$_2$—CH(CH$_3$)—O— | Na$^+$ | 1.12 (mc, 6H), 1.50 (mc, 2H), 1.61 (mc, 1H), 3.91 (mc, 2H), 6.68 (s, 2H) | (R,R)-Configuration of the CH$_3$-groups at the acetal ring |
| I-f-19 | C$_2$H$_5$ | CH$_3$ | C$_2$H$_5$ | —O—CH(CH$_3$)—CH$_2$—CH(CH$_3$)—O— | Na$^+$ | 1.03 and 1.12 (in each case d, Σ 6H), 1.50-1.71 (m, 3H), 3.79 and 3.91 (in each case mc, Σ 2H) | Isomer mixture with respect to the CH$_3$-groups at the acetal ring |
| I-f-20 | C$_2$H$_5$ | CH$_3$ | C$_2$H$_5$ | —O—CH$_2$—C(=CH$_2$)—CH$_2$—O— | Na$^+$ | 0.93 (t, 6H), 2.32 (q, 4H), 4.15, 4.22, 4.82 and 6.68 (in each case s, in each case 2H) | |
| I-f-21 | C$_2$H$_5$ | CH$_3$ | C$_2$H$_5$ | CH$_2$= | Na$^+$ | 117-118 | |
| I-f-22 | OCH$_3$ | CH$_3$ | CH$_3$ | CH$_2$= | Na$^+$ | 4.64 (s, 3H), 6.41 and 6.47 (in each case d, in each case 2H) | |
| I-f-23 | CH$_3$ | CH$_3$ | CH$_3$ | CH$_2$= | Na$^+$ | 1.90, 2.01 and 2.15 (in each case s, in each case 3H), 4.65 (s, 2H), 6.61 (mc, 2H) | |
| I-f-24 | OCH$_3$ | CH$_3$ | CH$_3$ | O= | Na$^+$ | 6.45 (mc, 2H) | |
| I-f-25 | C$_2$H$_5$ | CH$_3$ | C$_2$H$_5$ | —O—(CH$_2$)$_3$—O— | Na$^+$ | 6.62 (s, 2H) | |

Preparation of Starting Materials

2-[(2,6-diethyl-4-methylphenyl)acetyl]-4-methylidenecyclohexanecarboxylic acid

Example (XIII-1)

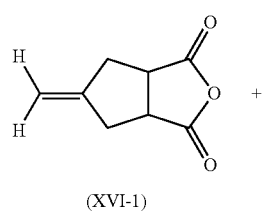

(XVI-1)

+

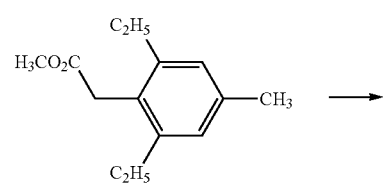

(XVII-1)

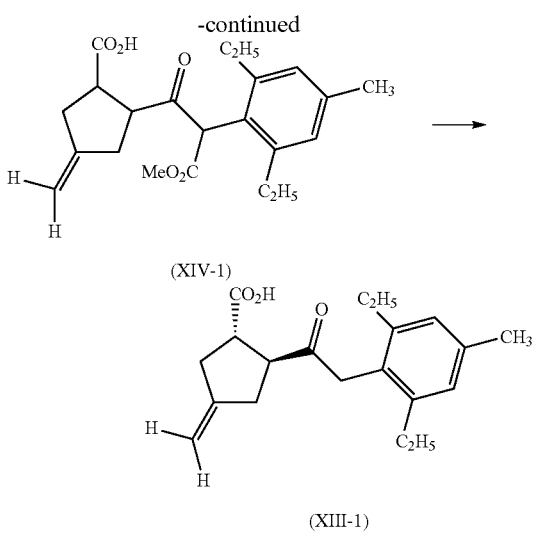

(XIV-1)

(XIII-1)

At −30° C., 14.48 g (65.7 mmol) of methyl 2-ethyl-4,6-dimethylphenyl acetate (XVII-1) are slowly added dropwise to a solution of lithium diisopropylamide in 250 ml of THF, prepared from 16.3 g (164 mmol) of diisopropylamine and the equimolar amount of a solution of n-butyllithium in hexane, and the mixture is stirred at room temperature for 45 min. At −20° C., 10.00 g (65.7 mmol) of 4-methylenecyclopentane-1,2-dicarboxylic anhydride (XVI-1), dissolved in 20 ml of THF, are then added, and the mixture is stirred at room temperature for around 12 h. For work-up, 100 ml of sat. ammonium chloride solution are added, a layer of ethyl acetate is added on top and the mixture is washed with water, dried (magnesium sulphate) and concentrated using a rotary evaporator. This gives 22.3 g of the compound (XIV-1) as a reddish oil which can be reacted without further purification.

$^1$H-NMR (400 MHz, CDCl$_3$): δ=1.11 and 1.12, in each case t, in each case 3H), 2.25-2.50 (m, 4H), 2.35 (s, 3H), 2.69 (mc, 2H), 2.72-2.90 (m, 4H), 3.66 (s, 3H), 4.85 (s, 2H) ppm 10 g of potassium hydroxide in 100 ml of water are added to 22.3 g of intermediate (XIV-1), and the mixture is heated at reflux for 24 h. The mixture is then allowed to cool to room temperature, acidified to pH 2 with 2N hydrochloric acid and stirred at room temperature for 1 h, and the precipitated solid is filtered off with suction. This gives 10.3 g (45%) of 2-[(2,6-diethyl-4-methyl-phenyl)acetyl]-4-methylidenecyclohexanecarboxylic acid (XIII-1) as a yellowish solid which can be used without further purification for the next reaction step.

$^1$H-NMR (400 MHz, CDCl$_3$): δ=1.12 (t, 6H), 2.45 (q, 4H), 3.90 (s, 2H), 4.91 (mc, 2H), 6.89 (s, 2H) ppm The following intermediates of the general formula (XIII) were prepared analogously:

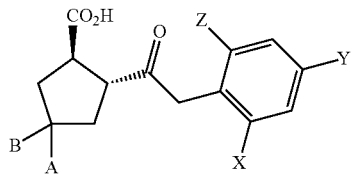

(XIII)

| Ex. No. | X | Y | Z | A B | M.p. [° C.] or $^1$H-NMR (400 MHz, CDCl$_3$, δ in ppm) |
|---|---|---|---|---|---|
| XIII-2 | OCH$_3$ | CH$_3$ | C$_2$H$_5$ | CH$_2$= | 3.28-3.40 (m, 2H), 3.78 (mc, 2H), 3.72 and 3.80 (s, in total 3H), 4.88 (mc, 2H) |
| XIII-3 | CH$_3$ | CH$_3$ | CH$_3$ | CH$_2$= | 2.15 (s, 6H), 2.25 (s, 3H), 3.83 (mc, 2H), 4.90 (mc, 2H) |
| XIII-4 | C$_2$H$_5$ | CH$_3$ | CH$_3$ | CH$_2$= | 1.20 (t, 3H), 2.12 (s, 3H), 2.22 (s, 6H), 3.70 (s, 2H), 4.90 (mc, 2H) |
| XIII-5 | OCH$_3$ | CH$_3$ | C$_2$H$_5$ | CH$_2$= | 1.17 (mc, 3H), 3.28-3.40 (m, 2H), 3.72 and 3.79 (in each case s, he 3H), 4.89 (mc, 2H) |
| XIII-6 | C$_2$H$_5$ | CH$_3$ | H | CH$_2$= | 96-100 |

The following intermediates of the general formula (XIV) were prepared analogously:

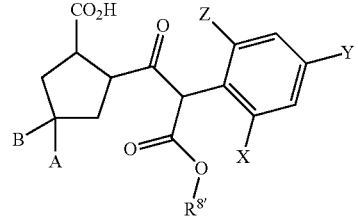

(XIV)

| Ex. No. | X | Y | Z | A B | R$^8$ | M.p.[° C.] or $^1$H-NMR (400 MHz, CDCl$_3$, δ in ppm) |
|---|---|---|---|---|---|---|
| XIV-2 | CH$_3$ | CH$_3$ | CH$_3$ | CH$_2$= | C$_2$H$_5$ | 118-119 |
| XIV-3 | C$_2$H$_5$ | CH$_3$ | CH$_3$ | CH$_2$= | CH$_3$ | 167-168 |

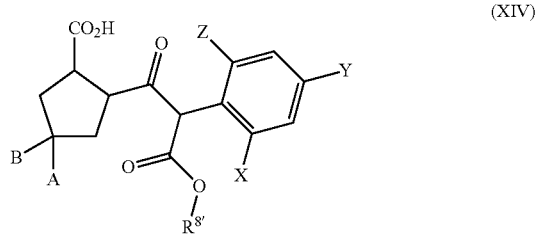

(XIV)

| Ex. No. | X | Y | Z | A B | R⁸ | M.p.[° C.] or $^1$H-NMR (400 MHz, CDCl$_3$, δ in ppm) |
|---|---|---|---|---|---|---|
| XIV-4 | OCH$_3$ | CH$_3$ | CH$_3$ | CH$_2$= | CH$_3$ | 2.20 and 2.31 (in each case s, in each case 3H), 3.13 and 3.58 (in each case s, in each case 3H), 4.85 (mc, 2H) |
| XIV-5 | OCH$_3$ | CH$_3$ | C$_2$H$_5$ | CH$_2$= | CH$_3$ | 1.08-1.18 (m, 3H), 2.69-3.00 (m, 4H), 4.88 (mc, 2H), 13.20 (s, br, 1H) |
| XIV-6 | C$_2$H$_5$ | CH$_3$ | H | CH$_2$= | CH$_3$ | 106-107 |

Methyl 2-[(2,6-diethyl-4-methylphenyl)acetyl]-4-methylidenecyclopentanecarboxylate Example (II-1)

Ethyl 2-[(2-ethyl-4,6-dimethylphenyl)acetyl]-4-oxo-cyclopentanecarboxylic

Example (II-2)

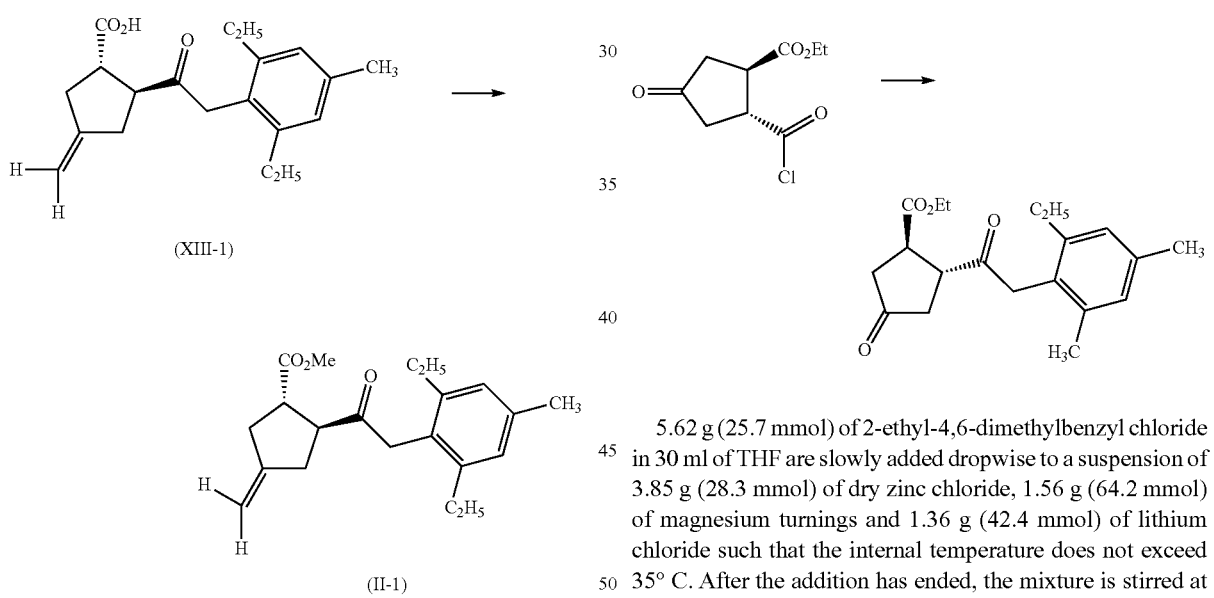

5.45 g (17.33 mmol) of 2-[(2,6-diethyl-4-methylphenyl) acetyl]-4-methylidenecyclohexane-carboxylic acid (XIII-1), together with 2.38 g of potassium carbonate and 2.62 g (20.8 mmol) of dimethylsulphate, are boiled at reflux in 50 ml of acetone for 5 h, and after cooling, the reaction mixture is taken up in ethyl acetate, extracted with water and dried (magnesium sulphate), and the solvent is distilled off. Chromatography on silica gel using ethyl acetate/hexane (v/v=30:70) gives 3.93 g (69%) of methyl 2-[(2,6-diethyl-4-methylphenyl)acetyl]-4-methylidenecyclohexane-carboxylate of the formula (II-1).

$^1$H-NMR (400 MHz, CDCl$_3$): δ=3.58 (s, 3H), 3.89 (s, 2H), 4.88 (s, 2H), 6.89 (s, 2H) ppm 5.62 g (25.7 mmol) of 2-ethyl-4,6-dimethylbenzyl chloride in 30 ml of THF are slowly added dropwise to a suspension of 3.85 g (28.3 mmol) of dry zinc chloride, 1.56 g (64.2 mmol) of magnesium turnings and 1.36 g (42.4 mmol) of lithium chloride such that the internal temperature does not exceed 35° C. After the addition has ended, the mixture is stirred at room temperature for another 2 h. At room temperature, the solution formed is slowly added dropwise to a mixture of 5.62 g (25.7 mmol) of ethyl 2-(chlorocarbonyl)-4-oxocyclopentanecarboxylate and 85 mg of bis(triphenylphosphine)palladium(II) chloride in 40 ml of THF, and the mixture is then stirred at room temperature for another 3 h.

The mixture is added to water, extracted twice with in each case 50 ml of methyl tert-butyl ether and dried (magnesium sulphate), and the solvent is distilled off. Chromatography on silica gel using ethyl acetate/hexane (v/v=30:70) gives 4.89 g (57%) of the desired intermediate in the form of colourless crystals of M.p. 75° C.

$^1$H-NMR (400 MHz, CDCl$_3$): δ=1.14 and 1.27 (in each case t, in each case 3H), 3.42-3.58 (m, 2H), 3.90 (s, 2H), 4.19 (q, 2H) ppm Ethyl 2-[(2,4,6-trimethylphenyl)acetyl]-4-oxocyclo-
pentanecarboxylate Example (II-3)

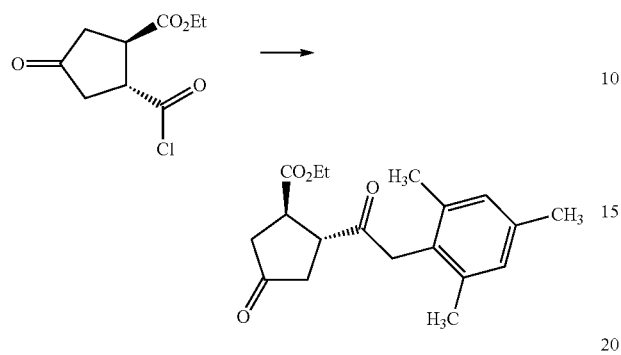

Over a period of 2 h, 4.08 g (17.4 mmol) of 2,4,6-trimeth-ylbenzylchloride in 40 ml of THF are added dropwise to 1.70 g (26.1 mmol) of zinc dust, activated with hydrochloric acid and dried under reduced pressure, and 0.50 g of trimethylsilyl chloride in 30 ml of THF, and the mixture is stirred at room temperature for another 2 h.

Under reduced pressure, 1.56 g (17.4 mmol) of copper(I) cyanide and 1.65 g (38.8 mmol) of lithium chloride are heated at 150° C. for 8 h and, after cooling, vented with argon and taken up in 25 ml of THF. At −25° C., the solution of 2,4,6-trimethylbenzylzinc chloride prepared above is added dropwise over a period of 20 min, and the mixture is stirred at this temperature for a further 20 min.

The mixture is cooled to −40° C., and a solution of 3.77 g (17.3 mmol) of ethyl 2-(chlorocarbonyl)-4-oxocyclopentan-ecarboxylate in 20 ml of THF is added over a period of 30 min, and the mixture is allowed to warm to room temperature and stirred for another 3 h.

For work-up, 100 ml of water are added, the mixture is extracted with ethyl acetate and the extract is dried (magnesium sulphate) and concentrated using a rotary evaporator. Chromatography on silica gel (ethyl acetate/hexane v/v=30:70) gives 1.98 g (27%) of the desired product.

$^1$H-NMR (400 MHz, CDCl$_3$): δ=2.18 (s, 6H), 2.23 (s, 3H), 3.48 (mc, 2H), 3.82 and 3.88 (in each case d, in each case 1H), 4.18 (q, 2H) ppm Methyl 2-[(2,6-diethyl-4-methylphenyl)acetyl]-4-
hydroxy-4-(hydroxymethyl)cyclopentanecarboxylate Example (II-4)

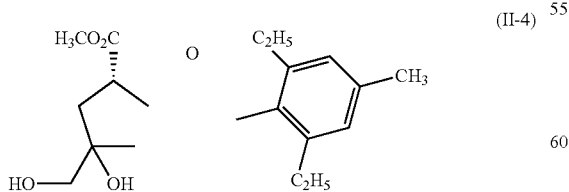

2.39 g (7.27 mmol) of methyl 2-[(2,6-diethyl-4-meth-ylphenyl)acetyl]-4-methylidenecyclohexane-carboxylate according to Example (II-2) are added to 1.37 ml of osmium tetroxide solution (2.5% strength solution in n-butanol) and 1.02 g (8.7 mmol) of N-methylmorpholine N-oxide in 25 ml of acetone/water (v/v=5:1), and the mixture is stirred at room temperature for 14 h. 0.745 g (3.64 mmol) of sodium dithionite is then added, the mixture is stirred at room temperature for 10 min and the solvent is then removed under reduced pressure. The residue is taken up in ethyl acetate, and the mixture is extracted with water, dried (magnesium sulphate) and then concentrated using a rotary evaporator. This gives 2.45 g (92%) of a yellowish viscose oil which can be reacted further without further purification.

$^1$H-NMR (400 MHz, CDCl$_3$): δ=1.70-2.25 (m, 4H), 3.34 (mc, 1H), 3.89 (dd, 2H) ppm Methyl 8-[(2,6-diethyl-4-methylphenyl)acetyl]-2,2-
dimethyl-1,3-dioxaspiro[4.4]nonane-7-carboxylate (Example II-5)

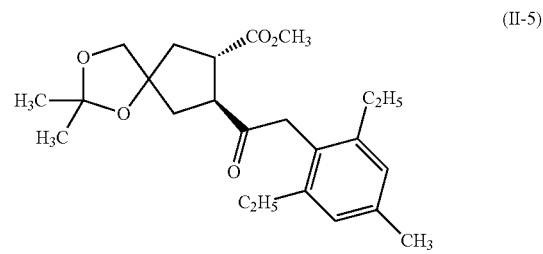

1.16 g (3.19 mmol) of methyl 2-[(2,6-diethyl-4-meth-ylphenyl)acetyl]-4-hydroxy-4-(hydroxymethyl)cyclopen-tanecarboxylate, 10 ml of 2,2-dimethoxypropane and 30 mg of p-toluene sulphonic acid are heated at reflux for 1 h. After cooling, the mixture is added to ice-water and extracted with ethyl acetate, the extract is washed successively with 1 N sodium bicarbonate solution and water and dried (magnesium sulphate) and the solvent is distilled off under reduced pressure. Chromatography on silica gel (mobile phase ethyl acetate/hexane v/v=35:65) gives 0.92 g (71%) of a colourless oil. According to $^1$H-NMR, an endo/exo isomer mixture of the compound of the formula (II-5) is present.

$^1$H-NMR (400 MHz, CDCl$_3$): δ=1.33-1.37 (Singlets split, in total 6H), 2.26 (s, 3H), 3.22 (mc, 1H), 3.80-3.90 (m, 4H), 6.89 (s, 2H) ppm Ethyl 8-[(2-ethyl-4,6-dimethylphenyl)acetyl]-1,4-
dioxaspiro[4.4]nonane-7-carboxylate (Example II-16)

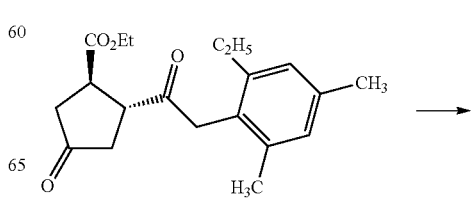

-continued

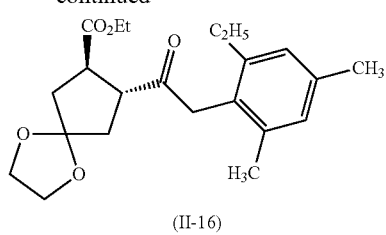

(II-16)

1.20 g (3.63 mmol) of ethyl 2-[(2-ethyl-4,6-dimethylphenyl)acetyl]-4-oxocyclopentane-carboxylate according to Example (II-2), 338 mg (5.4 mmol) of ethanediol, 578 mg (5.4 mmol) of trimethyl orthoformate and 20 mg of p-toluene sulphonic acid in 30 ml of toluene are stirred at room temperature for 24 h. The solvent is then distilled off and the residue is chromatographed on silica gel (mobile phase ethyl acetate/hexane v/v=15:85). This gives 819 mg (60%) of the desired compound in the form of colourless crystals of m.p. 72-73° C.

The following intermediates of the general formula (II) were prepared analogously

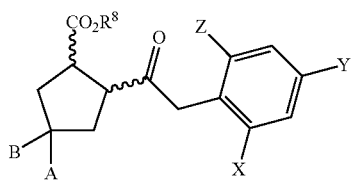

(II)

| Ex. No. | X | Y | Z | A B | $R^8$ | $^1$H-NMR (400 MHz, CDCl$_3$, δ in ppm) | Isomerism |
|---|---|---|---|---|---|---|---|
| II-6 | OCH$_3$ | CH$_3$ | C$_2$H$_5$ | CH$_2$= | CH$_3$ | 3.38 and 3.59 (in each case q, in each case 1H), 3.67 (s, 3H), 3.71 (mc, 2H), 3.75 (s, 3H), 4.86 (mc, 2H) | trans |
| II-7 | CH$_3$ | CH$_3$ | CH$_3$ | CH$_2$= | CH$_3$ | 2.15 (s, 6H), 2.27 (s, 3H), 3.40 (mc, 2H), 3.74 (mc, 2H), 4.90 (mc, 2H) | trans |
| II-8 | CH$_3$ | CH$_3$ | C$_2$H$_5$ | CH$_2$= | CH$_3$ | 1.15 (t, 3H), 3.28-3.40 (m, 2H), 3.67 (s, 2H), 3.85 (s, 3H), 4.88 (mc, 2H) | trans |
| II-9 | CH$_3$ | CH$_3$ | CH$_3$ | CH$_2$= | CH$_3$ | 3.10 and 3.40 (in each case mc, in each case 1H), 3.62 (s, 3H), 3.78 and 3.90 (in each case q, in each case 1H) | cis |
| II-10 | C$_2$H$_5$ | CH$_3$ | C$_2$H$_5$ | CH$_2$= | t-C$_4$H$_9$ | 1.42 (s, 9H), 3.16 and 3.38 (in each case q, in each case 1H), 3.88 (s, 2H), 4.86 (mc, 1H) | cis |
| II-11 | C$_2$H$_5$ | CH$_3$ | C$_2$H$_5$ | —OCH$_2$CH=CHCH$_2$O— | C$_2$H$_5$ | 2.29 (s, 3H), 2.45 (q, 4H), 3.88 (s, 2H), 4.14-4.25 (m, 6H), 5.68 (mc, 2H) | trans |
| II-12 | C$_2$H$_5$ | CH$_3$ | C$_2$H$_5$ | —O(CH$_2$)$_2$O— | C$_2$H$_5$ | 1.12 (mc, 6H), 1.24 (t, 3H), 3.39 and 3.49 (in each case mc, in each case 1H), 3.90 (mc, 4H), 4.14 (q, 2H) | trans |
| II-13 | C$_2$H$_5$ | CH$_3$ | CH$_3$ | —O(CH$_2$)$_4$O— | C$_2$H$_5$ | 1.12 and 1.23 (in each case t, in each case 3H), 2.49 (q, 2H), 3.61 (mc, 4H), 3.82 (s, 2H), 4.12 (q, 2H) | trans |
| II-14 | C$_2$H$_5$ | CH$_3$ | CH$_3$ | —OCH$_2$CH=CHCH$_2$O— | C$_2$H$_5$ | 3.35-3.50 (m, 2H), 3.85 (s, 2H), 4.10-4.25 (m, 6H), 5.68 (s, 2H) | trans |
| II-15 | C$_2$H$_5$ | CH$_3$ | CH$_3$ | —O(CH$_2$)$_3$O— | C$_2$H$_5$ | 2.24 and 2.28 (in each case s, in each case 3H), 3.35-3.48 (m, 2H), 3.80-3.95 (m, 6H) | trans |
| II-16 | C$_2$H$_5$ | CH$_3$ | CH$_3$ | —O(CH$_2$)$_2$O— | C$_2$H$_5$ | 72-73 | trans |
| II-17 | C$_2$H$_5$ | CH$_3$ | C$_2$H$_5$ | —O(CH$_2$)$_3$O— | C$_2$H$_5$ | 1.24 (t, 3H), 3.31-3.40 (m, 2H), 3.80-3.95 (m, 6H), 4.15 (q, 2H) | trans |
| II-18 | C$_2$H$_5$ | CH$_3$ | C$_2$H$_5$ | O= | C$_2$H$_5$ | 2.28 (s, 3H), 3.33-3.46 (m, 3H), 3.87 and 3.95 (in each case d, in each case 1H), 6.90 (s, 2H) | cis |
| II-19 | C$_2$H$_5$ | CH$_3$ | C$_2$H$_5$ | CH$_2$= | C$_2$H$_5$ | 3.35-3.51 (m, 2H), 3.89 (s, 2H), 4.20-4.48 (m, 4H), 4.90 (s, 2H) | trans |
| II-20 | C$_2$H$_5$ | CH$_3$ | C$_2$H$_5$ | —O—CH(CH$_3$)—CH$_2$—CH(CH$_3$)—O— mixture with respect to the CH$_3$-groups at the acetal | C$_2$H$_5$ | 1.10-1.28 (m, 15H), 3.35-3.58 (m, 2H), 3.70-4.00 (m, 4H), 4.12 (mc, 2H) | trans |
| II-21 | C$_2$H$_5$ | CH$_3$ | C$_2$H$_5$ | —S(CH$_2$)$_3$O— | C$_2$H$_5$ | 3.40-3.63 (m, 2H), 3.82 (mc, 2H), 3.88 (mc, 2H), 4.14 (mc, 2H) 6.89 (s, 2H) | trans |
| II-22 | C$_2$H$_5$ | CH$_3$ | C$_2$H$_5$ | —OCH$_2$CH(CH$_3$)CH$_2$O— | C$_2$H$_5$ | 0.76 and 0.82 (in each case d, in total 3 H), 2.00 (mc, 1H), 3.28-3.50 (m, 3H), 3.75-3.90 (m, 2H) | trans |
| II-23 | C$_2$H$_5$ | CH$_3$ | C$_2$H$_5$ | —S(CH$_2$)O— | C$_2$H$_5$ | 3.05 (mc, 2H), 3.87 and 3.91 (in each case d, in each case 2H), 4.05 (mc, 2H), 4.12 (q, 2H) | trans |
| II-24 | C$_2$H$_5$ | CH$_3$ | C$_2$H$_5$ | —O—CH$_2$—C(=CH$_2$)—CH$_2$—O— | C$_2$H$_5$ | 3.38-3.50 (m, 2H), 3.89 (s, 2H), 4.20-4.39 (m, 4H), 4.90 (s, 2H) | trans |
| II-25 | OCH$_3$ | CH$_3$ | C$_2$H$_5$ | CH$_2$= | CH$_3$ | 1.14 (t, 3H), 2.31 (s, 3H), 3.68 (s, 3H), 3.72 (s, 3H, 4.85 (mc, 2H), 6.52 and 6.65 (in each case s, in each case 1H) | trans |

-continued

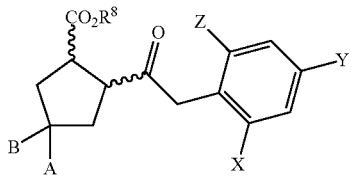

(II)

| Ex. No. | X | Y | Z | A B | R⁸ | ¹H-NMR (400 MHz, CDCl₃, δ in ppm) | Isomerism |
|---|---|---|---|---|---|---|---|
| 11-26 | $C_2H_5$ | $CH_3$ | H | $CH_2=$ | $CH_3$ | 1.14 (t, 3H), 2.31 (s, 3H), 3.68 (s, 3H), 3.72 (s, 3H), 4.85 (mc, 2H), 6.52 and 6.65 (in each case s, in each case 1H) | trans |

2,6-Diethyl-4-methylbenzyl chloride

Example (XIX-1)

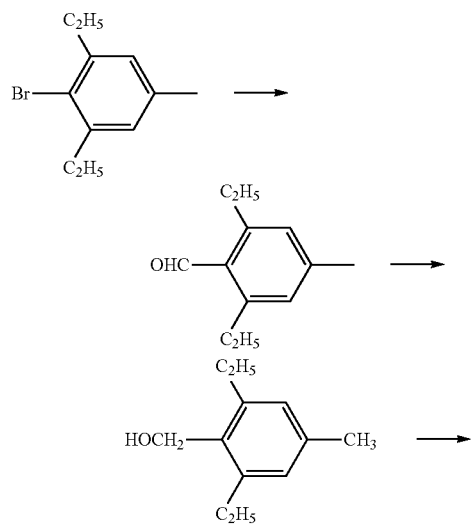

(XIX-1)

With ice-cooling, 48.0 g (3 equivalent) of N,N-dimethylformamide, dissolved in 50 ml of THF, are slowly added dropwise to a solution of 2,6-diethyl-4-methylphenylmagnesium bromide, prepared from 6.00 g of magnesium turnings and 50 g of 1-bromo-2,6-diethyl-4-methylbenzene in 220 ml of THF, and the mixture is stirred at room temperature for another 3 h. The mixture is poured onto a sat. ammonium chloride solution and extracted with ethyl acetate, and the extract is dried (magnesium sulphate) giving, after distillative removal of the solvent, 38.70 g (99%) of 2,6-diethyl-4-methylbenzaldehyde as a colourless oil, ¹H-NMR (400 MHz, CDCl₃): δ=1.22 (t, 6H), 2.32 (s, 3H), 2.93 (q, 4H), 6.91 (s, 2H), 10.52 (s, 1H)

The following compounds were prepared analogously:

2-ethyl-4,6-dimethylbenzaldehyde:

¹H-NMR (400 MHz, CDCl₃): 1.22 (t, 3H), 2.32 (s, 3H), 2.57 (s, 3H), 2.95 (q, 2H), 6.92 (mc, 2H), 10.55 (s, 1H) ppm 2-methoxy-4,6-dimethylbenzaldehyde 2-methoxy-6-ethyl-4-methylbenzaldehyde 2-cyclopropyl-6-ethyl-4-methylbenzaldehyde 2,6-cyclopropyl-4-methylbenzaldehyde A solution of 35.5 g (201.4 mmol) of 2,6-diethyl-4-methylbenzaldehyde, dissolved in 80 ml of diethyl ether is added dropwise to a suspension of 2.10 g (55.4 mmol) of lithium aluminium hydride in 200 ml of diethyl ether. The mixture is then heated at reflux for another 1 h. After cooling, the mixture is hydrolyzed with water and 10% strength sulphuric acid, the phases are separated and the aqueous phase is extracted two more times with diethyl ether. Drying (magnesium sulphate), distillative removal of the solvent and chromatography of the resulting crude product on silica gel (ethyl acetate/hexane=30:70) gives 33.10 g (92%) of 2,6-diethyl-4-methylbenzyl alcohol in the form of colourless crystals of m.p. 71-72° C. ¹H-NMR (400 MHz, CDCl₃): δ=1.22 (t, 6H), 2.30 (s, 3H), 2.74 (q, 4H), 4.71 (s, 2H), 6.90 (s, 2H).

Direct preparation of 2,6-diethyl-4-methylbenzyl alcohol from 1-bromo-2,6-diethyl-4-methylbenzene

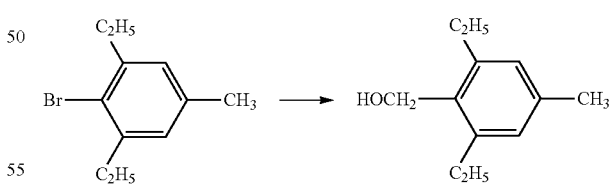

Over a period of 30 min, gaseous formaldehyde (generated from 5.56 g of paraformaldehyde) is introduced with stirring into a solution of 2,6-diethyl-4-methylphenylmagnesium bromide, prepared from 12.40 g (54.6 mmol) of 1-bromo-2,6-diethyl-4-methylbenzene and 1.47 g (60.65 mmol) of magnesium turnings in 50 ml of THF, and the mixture is then stirred at room temperature for another 2 h. Distillative removal of the solvent and chromatography on silica gel (see above) gives 6.88 g (71%) of 2,6-diethyl-4-methylbenzyl alcohol.

The following compounds are prepared analogously:
2-ethyl-4,6-dimethylbenzyl alcohol: m.p. 40-41° C.
2-methoxy-4,6-dimethylbenzyl alcohol: m.p. 63-65° C.
2-cyclopropyl-6-ethyl-4-methylbenzyl alcohol
2,6-cyclopropyl-4-methylbenzyl alcohol 11.20 g (94.16 mmol) of thionyl chloride are slowly added dropwise to 15.26 g (85.6 mmol) of 2,6-diethyl-4-methylbenzyl alcohol in 200 ml of dichloromethane, and the mixture is then heated at reflux for 2 h. After cooling, the mixture is stirred with 50 ml of water for 10 min, and the organic phase is separated off, dried (magnesium sulphate), concentrated using a rotary evaporator and chromatographed in silica gel (ethyl acetate/hexane=15:85). This gives 16.18 g (96%) 2,6-diethyl-4-methylbenzyl chloride as a colourless oil. $^{1}$H-NMR (400 MHz, CDCl$_3$): δ=1.26 (t, 6H), 2.30 (s, 3H), 2.76 (q, 4H), 4.70 (s, 2H), 6.88 (s, 2H).

2,6-Diethyl-4-methylbenzyl bromide

Example (XIX-2)

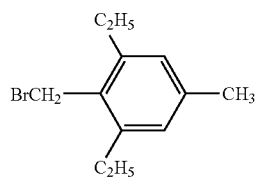

14.7 g (82.5 mmol) of 2,6-diethyl-4-methylbenzyl alcohol in 150 ml of hydrobromic acid are stirred at 100° C. for 4 h. After cooling, the mixture is extracted with dichloromethane and the extract is washed with water, dried (magnesium sulphate) and concentrated using a rotary evaporator. Distillation (110° C. bath temperature, 0.3 mbar) gives 17.82 g (89%) of 2,6-diethyl-4-methylbenzyl bromide as a colourless oil. $^{1}$H-NMR (400 MHz, CDCl$_3$): δ=1.28 (t, 6H), 2.30 (s, 3H), 2.73 (q, 4H), 4.61 (s, 2H), 6.90 (s, The following precursors and intermediates of the formula (XIX) were obtained in an analogous manner:

Example No. 1

1. Herbicidal Pre-Emergence Action

Seeds of monocotylidonous and dicotylidonous weed and crop plants are placed in sandy loam in wood fibre pots and covered with soil. The test compounds, formulated in the form of wettable powders (WP), are then, as an aqueous suspension with a water application rate of 600 l/ha (converted), with 0.2% of wetting agent added, applied to the surface of the covering soil in different amounts.

After the treatment, the pots are placed in a greenhouse and kept under good growth conditions for the test plants. The visual assessment of the emergence damage on the test plants is carried out after a trial period of three weeks by comparison with the untreated controls (herbicidal effect in percent: 100% effect=the plants have died, 0% effect=like control plants).

In addition to the compounds mentioned above, the following compounds, applied by the pre-emergence method at 320 g/ha a.i., show an effect of ≧80% against *Alopecurus myosuroides, Echinocloa crus-galli, Lolium multiflorum* and *Setaria viridis*: I-a-3, I-a-6, I-a-7, I-a-8, I-a-9, I-a-10, I-a-11, I-a-12, I-a-13, I-a-14, I-b-4, I-b-5, I-b-6, I-b-7, I-b-8, I-c-3, I-c-4, I-c-5, I-c-7, I-c-9, I-c-10, I-c-11, I-c-12, I-c-14

2. Herbicidal Post-Emergence Action

Seeds of monocotylidonous and dicotylidonous weed and crop plants are placed in sandy loam in wood fibre pots, covered with soil and cultivated in a greenhouse under good growth conditions. Two to three weeks after sowing, the test plants are treated at the one-leaf stage. The test compounds, formulated as wettable powders (WP), are then with a water application rate of 600 l/ha (converted), with 0.2% of wetting agent added, sprayed onto the green parts of the plants in different amounts. After the test plants have been kept in the greenhouse under optimum growth conditions for about three weeks, the effect of the preparations is assessed visually in comparison to untreated controls (herbicidal effect in percent: 100% effect=the plants have died, 0% effect=like control plants).

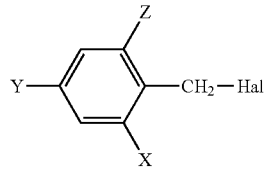

(XIX)

| Ex. No. | Hal | X | Y | Z | M.p. °C. or $^{1}$H-NMR (400 MHz, CDCl$_3$, δ in ppm) |
|---|---|---|---|---|---|
| XIX-3 | Cl | C$_2$H$_5$ | CH$_3$ | CH$_3$ | 1.26 (t, 3H), 2.28 (s, 3H), 2.41 (s, 3H), 2.72 (q, 2H), 4.69 (s, 2H) |
| XIX-4 | Br | C$_2$H$_5$ | CH$_3$ | CH$_3$ | 2.28 (s, 3H), 2.39 (s, 3H), 2.73 (q, 2H), 4.60 (s, 2H), 6.85 and 6.88 (in each case s, in each case 1H) |
| XIX-5 | Cl | OCH$_3$ | CH$_3$ | CH$_3$ | 2.21 and 2.38 (in each case s, in each case 3H), 3.75 (s, 3H), 4.72 (s, 2H), 6.59 and 6.62 (in each case s, in each case 1H) |
| XIX-6 | Cl | cyclopropyl | CH$_3$ | C$_2$H$_5$ | |
| XIX-7 | Br | cyclopropyl | CH$_3$ | C$_2$H$_5$ | |

In addition to the compounds mentioned above, the following compounds, applied by the pre-emergence method at 80 g/ha, show an effect of ≧80% against *Alopecurus myosuroides, Echinocloa crus-galli, Lolium multiflorum* and *Setaria viridis*: I-a-2, I-a-3, I-a-6, I-a-7, I-a-8, I-a-10, I-a-11, I-a-12, I-a-13, I-a-14, I-b-2, I-b-6, I-b-7, I-c-3, I-c-7, I-c-8, I-c-9, I-c-10, I-c-11, I-c-12, I-c-14, I-c-15, I-f-1

Use of Safeners:

If it is to be additionally tested as to whether safeners can improve the plant compatibility of test substances in the case of crop plants, the following options are used for applying the safeners:

- Seeds of the crop plants are, before sowing, dressed with safener substance (the amount of safener stated in percent, based on the weight of the seed)
- Before the application of the test substances, the crop plants are sprayed with the safener at a certain application rate per hectare (usually one day before the application of the test substances)
- The safener is applied together with the test substance as a tank mix (the amount of safener stated in g/ha or as a ratio, based on the herbicide).

Container Trials with Cereals in the Greenhouse

| Mefenpyr 1 day prior to herbicide application | | |
|---|---|---|
| 28 days after application | | |
| | Application rate g of a.i./ha | Summer wheat observed (%) |
| I-a-2 | 50 | 60 |
| | 25 | 50 |
| | 12.5 | 40 |
| I-a-2 + mefenpyr | 50 + 50 | 5 |
| | 25 + 50 | 5 |
| | 12.5 + 50 | 0 |
| 10 days after application | | |
| | Application rate g of a.i./ha | Summer wheat observed (%) |
| I-a-10 | 50 | 60 |
| | 25 | 50 |
| | 12.5 | 30 |
| I-a-10 + mefenpyr | 50 + 50 | 5 |
| | 25 + 50 | 3 |
| | 12.5 + 50 | 2 |
| I-c-7 | 50 | 60 |
| | 25 | 50 |
| | 12.5 | 40 |
| I-c-7 + mefenpyr | 50 + 50 | 5 |
| | 25 + 50 | 5 |
| | 12.5 + 50 | 3 |
| I-a-11 | 50 | 70 |
| | 25 | 50 |
| | 12.5 | 30 |
| I-a-11 + mefenpyr | 50 + 50 | 10 |
| | 25 + 50 | 10 |
| | 12.5 + 50 | 8 |
| I-a-14 | 50 | 60 |
| | 25 | 60 |
| | 12.5 | 50 |
| I-a-14 + mefenpyr | 50 + 50 | 10 |
| | 25 + 50 | 10 |
| | 12.5 + 50 | 5 |
| I-a-13 | 50 | 60 |
| | 25 | 50 |
| | 12.5 | 40 |

-continued

| Mefenpyr 1 day prior to herbicide application | | |
|---|---|---|
| I-a-13 + mefenpyr | 50 + 50 | 5 |
| | 25 + 50 | 2 |
| | 12.5 + 50 | 2 |
| 28 days after application | | |
| | Application rate g of a.i./ha | Summer wheat observed (%) |
| I-c-9 | 100 | 50 |
| | 50 | 40 |
| | 25 | 30 |
| I-c-9 + mefenpyr | 100 + 50 | 10 |
| | 50 + 50 | 5 |
| | 25 + 50 | 0 |
| | Application rate g of a.i./ha | Summer wheat observed (%) 10 days after application |
| I-a-8 | 100 | 60 |
| | 50 | 50 |
| | 25 | 40 |
| | 12.5 | 20 |
| I-a-8 + mefenpyr | 100 + 50 | 5 |
| | 50 + 50 | 5 |
| | 25 + 50 | 2 |
| | 12.5 + 50 | 0 |
| | Application rate g of a.i./ha | Summer barley observed (%) 10 days after application | Summer wheat observed (%) 10 days after application |
| I-a-8 | 100 | 20 | 30 |
| | 50 | 20 | 30 |
| | 25 | 10 | 20 |
| I-a-8 + mefenpyr | 100 + 50 | 10 | 5 |
| | 50 + 50 | 8 | 5 |
| | 25 + 50 | 5 | 3 |
| | Application rate g of a.i./ha | Summer barley observed (%) 28 days after application | Summer wheat observed (%) 28 days after application |
| I-c-14 | 100 | 20 | 70 |
| | 50 | 10 | 60 |
| | 25 | | 50 |
| | 12.5 | | 40 |
| I-c-14 + mefenpyr | 100 + 50 | 5 | 5 |
| | 50 + 50 | 0 | 5 |
| | 25 + 50 | | 5 |
| | 12.5 + 50 | | 0 |
| | Application rate g of a.i./ha | Summer wheat observed (%) 28 days after application |
| I-c-7 | 100 | 30 |
| | 50 | 30 |
| | 25 | 30 |
| | 12.5 | 10 |
| I-c-7 + mefenpyr | 100 + 50 | 2 |
| | 50 + 50 | 2 |
| | 25 + 50 | 0 |
| | 12.5 + 50 | 0 |
| | Application rate g of a.i./ha | Summer barley observed (%) 28 days after application | Summer wheat observed (%) 28 days after application |
| I-a-11 | 100 | 10 | 70 |
| | 50 | 8 | 60 |
| | 25 | | 50 |
| | 12.5 | | 10 |

-continued

| Mefenpyr 1 day prior to herbicide application | | | |
|---|---|---|---|
| I-a-11 + mefenpyr | 100 + 50 | 0 | 2 |
| | 50 + 50 | 0 | 0 |
| | 25 + 50 | | 0 |
| | 12.5 + 50 | | 0 |
| I-c-3 | 100 | 95 | 99 |
| | 50 | 30 | 60 |
| | 25 | 15 | 20 |
| | 12.5 | | 10 |
| I-c-3 + mefenpyr | 100 + 50 | 20 | 15 |
| | 50 + 50 | 15 | 10 |
| | 25 + 50 | 10 | 5 |
| | 12.5 + 50 | | 5 |
| I-a-3 | 100 | 70 | 85 |
| | 50 | 60 | 70 |
| | 25 | 20 | 60 |
| | 12.5 | | 10 |
| I-a-3 + mefenpyr | 100 + 50 | 20 | 20 |
| | 50 + 50 | 10 | 10 |
| | 25 + 50 | 10 | 8 |
| | 12.5 + 50 | | 5 |
| I-a-14 | 100 | 20 | 70 |
| | 50 | 10 | 30 |
| | 25 | 8 | 30 |
| | 12.5 | 5 | 10 |
| I-a-14 + mefenpyr | 100 + 50 | 8 | 8 |
| | 50 + 50 | 5 | 5 |
| | 25 + 50 | 0 | 5 |
| | 12.5 + 50 | 0 | 0 |
| I-c-10 | 100 | 95 | |
| | 50 | 50 | 95 |
| | 25 | | 50 |
| | 12.5 | | 15 |
| I-c-10 + mefenpyr | 100 + 50 | 30 | |
| | 50 + 50 | 20 | 40 |
| | 25 + 50 | | 20 |
| | 12.5 + 50 | | 10 |
| I-a-25 | 100 | 85 | 85 |
| | 50 | 60 | 70 |
| | 25 | | 30 |
| | 12.5 | | 10 |
| I-a-25 + mefenpyr | 100 + 50 | 20 | 10 |
| | 50 + 50 | 10 | 8 |
| | 25 + 50 | | 5 |
| | 12.5 + 50 | | 0 |
| I-b-13 | 100 | 50 | 85 |
| | 50 | 20 | 80 |
| | 25 | | 40 |
| | 12.5 | | 20 |
| I-b-13 + mefenpyr | 100 + 50 | 10 | 10 |
| | 50 + 50 | 5 | 10 |
| | 25 + 50 | | 5 |
| | 12.5 + 50 | | 0 |
| I-f-19 | 100 | 50 | 99 |
| | 50 | 20 | 97 |
| | 25 | 10 | 90 |
| | 12.5 | 10 | 20 |
| I-f-19 + mefenpyr | 100 + 50 | 10 | 20 |
| | 50 + 50 | 5 | 10 |
| | 25 + 50 | 0 | 10 |
| | 12.5 + 50 | 0 | 10 |
| I-a-58 | 100 | 15 | 60 |
| | 50 | 10 | 20 |
| | 25 | 5 | 15 |
| | 12.5 | | 10 |
| I-a-58 + mefenpyr | 100 + 50 | 5 | 5 |
| | 50 + 50 | 0 | 0 |
| | 25 + 50 | 0 | 0 |
| | 12.5 + 50 | | 0 |

Pre-Emergence Method

| | 80 g/ha | | | | |
|---|---|---|---|---|---|
| Example | ALOMY | AVEFA | ECHCG | LOLMU | SETVI |
| I-a-1 | 90 | 80 | 50 | 100 | 60 |
| I-a-2 | 90 | 50 | 90 | 100 | 50 |
| I-a-3 | 100 | 80 | 100 | 100 | 100 |
| I-a-5 | 60 | 60 | 80 | 90 | 70 |
| I-a-6 | 100 | 60 | 60 | 100 | 60 |
| I-a-7 | 100 | 80 | 70 | 90 | 70 |
| I-a-8 | 100 | 60 | 90 | 100 | 90 |
| I-a-9 | 90 | 70 | 100 | 100 | 90 |
| I-a-10 | 70 | 50 | 80 | 100 | 60 |
| I-a-11 | 90 | 50 | 100 | 100 | 70 |
| I-a-12 | 100 | 80 | 100 | 100 | 90 |
| I-a-13 | 90 | 80 | 100 | 100 | 90 |
| I-a-14 | 100 | 80 | 100 | 100 | 90 |
| I-a-15 | 80 | 40 | 70 | 100 | 70 |
| I-a-19 | 90 | 20 | 0 | 100 | 20 |
| I-a-25 | 100 | 70 | 90 | 100 | 90 |
| I-a-26 | 100 | 70 | 100 | 100 | 100 |
| I-a-27 | 90 | 80 | 100 | 100 | 90 |
| I-a-28 | 100 | 80 | 100 | 100 | 90 |
| I-a-29 | 90 | | 70 | 80 | 20 |
| I-a-30 | 80 | 0 | | 70 | 70 |
| I-a-31 | 80 | 40 | 100 | 100 | 90 |
| I-a-32 | 90 | 60 | 40 | 100 | 20 |
| I-a-35 | 80 | 80 | 70 | 100 | 70 |
| I-a-36 | 60 | 70 | 80 | 90 | 80 |
| I-a-38 | 100 | 40 | 40 | 100 | 90 |
| I-a-39 | 80 | 70 | 0 | 100 | 30 |
| I-a-40 | 50 | 40 | 80 | 100 | 50 |
| I-a-41 | 60 | 60 | 50 | 100 | |
| I-a-45 | 80 | 60 | 100 | 80 | 100 |
| I-a-48 | 80 | 60 | 40 | 80 | 70 |
| I-a-49 | 100 | 90 | 100 | 100 | 90 |
| I-a-50 | 100 | 60 | 80 | 100 | 70 |
| I-a-55 | 60 | 60 | 100 | 50 | 90 |
| I-a-57 | 80 | 60 | 100 | 100 | 90 |
| I-a-58 | 70 | 70 | 100 | 100 | 100 |
| I-a-61 | 70 | 60 | 80 | 100 | 60 |
| I-a-62 | 100 | 40 | 100 | 100 | 90 |
| I-a-68 | 40 | 40 | 50 | 80 | 0 |
| I-a-69 | 50 | 70 | 20 | 70 | 80 |
| I-a-70 | 80 | 60 | 80 | 80 | 60 |
| I-b-1 | 90 | 40 | 40 | 100 | 70 |
| I-b-2 | 90 | 50 | 30 | 100 | 40 |
| I-b-3 | 90 | 60 | 0 | 100 | 50 |
| I-b-4 | 90 | 50 | 70 | 100 | 60 |
| I-b-5 | 90 | | 10 | 100 | 60 |
| I-b-6 | 100 | 80 | 30 | 100 | 60 |
| I-b-7 | 100 | 80 | 60 | 100 | 70 |
| I-b-8 | 100 | 80 | 90 | 100 | 90 |
| I-b-12 | 100 | 70 | 100 | 100 | 90 |
| I-b-13 | 100 | 80 | 100 | 100 | 100 |
| I-b-14 | 100 | 70 | 100 | 100 | 100 |
| I-b-15 | 80 | 50 | 100 | | 80 |
| I-b-16 | 100 | 80 | 100 | 100 | 100 |
| I-b-17 | 90 | 80 | 100 | 100 | 90 |
| I-b-18 | 100 | 70 | 80 | 100 | 70 |
| I-b-19 | 100 | | 100 | 100 | 90 |
| I-b-20 | 100 | 90 | 80 | 100 | 90 |
| I-b-21 | 80 | 80 | 80 | 100 | 20 |
| I-b-22 | 100 | 70 | 100 | 100 | 80 |
| I-b-23 | 90 | 70 | 100 | 100 | 50 |
| I-b-24 | 70 | 70 | 100 | 100 | 40 |
| I-b-25 | 90 | 70 | 100 | 100 | 60 |
| I-b-27 | | 70 | 100 | 100 | 70 |
| I-b-28 | 90 | 50 | 100 | 100 | 70 |
| I-b-29 | | 70 | 100 | 100 | 80 |
| I-b-30 | 100 | 70 | 100 | 100 | 90 |
| I-b-37 | 90 | 40 | 70 | 70 | 70 |
| I-b-38 | 80 | 70 | 80 | 60 | 80 |
| I-b-39 | 60 | 50 | 10 | 80 | 0 |
| I-b-40 | 90 | 50 | 50 | 100 | 30 |
| I-b-41 | 50 | 40 | 0 | 100 | 50 |
| I-b-42 | | 70 | 60 | 100 | 90 |

-continued

| | | 80 g/ha | | | |
|---|---|---|---|---|---|
| Example | ALOMY | AVEFA | ECHCG | LOLMU | SETVI |
| I-b-43 | 90 | 40 | 20 | 90 | 60 |
| I-b-45 | 90 | 40 | 20 | 60 | 30 |
| I-b-46 | 90 | 60 | 0 | 100 | 0 |
| I-b-48 | 80 | 20 | 0 | 70 | 0 |
| I-b-49 | 90 | 70 | 50 | 70 | 0 |
| I-b-51 | 80 | 30 | 30 | 70 | 0 |
| I-b-62 | 50 | 40 | 70 | 70 | 80 |
| I-b-63 | 70 | | 100 | 100 | 70 |
| I-b-64 | 60 | 50 | 0 | 100 | 90 |
| I-b-65 | 60 | 70 | 90 | 100 | 70 |
| I-b-66 | 80 | 80 | 100 | 100 | 80 |
| I-b-67 | 90 | 90 | 100 | 100 | 90 |
| I-b-69 | 100 | 80 | 100 | 100 | 80 |
| I-b-70 | 100 | 80 | 100 | 100 | 90 |
| I-b-72 | 80 | 60 | 100 | 100 | 100 |
| I-b-73 | 80 | 80 | 90 | 100 | 100 |
| I-b-74 | 60 | 60 | 100 | 100 | 70 |
| I-b-75 | 60 | 60 | 100 | 100 | 70 |
| I-b-76 | 100 | 60 | 100 | 100 | 70 |
| I-b-77 | 60 | 40 | | 90 | 60 |
| I-b-78 | 100 | 60 | 100 | 100 | 60 |
| I-b-79 | 70 | 70 | 100 | 100 | 80 |
| I-c-2 | 90 | 50 | 40 | 100 | 60 |
| I-c-3 | 100 | 80 | 40 | 100 | 70 |
| I-c-4 | 90 | 80 | 60 | 90 | 50 |
| I-c-5 | 80 | 80 | 90 | 80 | 80 |
| I-c-6 | 50 | 10 | 90 | 80 | 60 |
| I-c-7 | 100 | 70 | 100 | 90 | 70 |
| I-c-8 | 60 | 40 | 60 | 100 | 50 |
| I-c-9 | 100 | 70 | 100 | 100 | 70 |
| I-c-10 | 100 | 80 | 100 | 100 | 90 |
| I-c-11 | 90 | 70 | 100 | 90 | 90 |
| I-c-12 | 100 | 80 | 100 | 100 | 100 |
| I-c-13 | 90 | 50 | 60 | 80 | 60 |
| I-c-14 | 90 | 70 | 90 | 100 | 70 |
| I-c-18 | 90 | 0 | 100 | 100 | 10 |
| I-c-19 | 100 | 70 | 50 | 90 | 90 |
| I-c-21 | 90 | 70 | 100 | 100 | 100 |
| I-c-22 | 100 | 70 | 100 | 100 | 100 |
| I-c-23 | 100 | 70 | 100 | 100 | 100 |
| I-c-24 | 90 | | 70 | 100 | 70 |
| I-c-25 | 100 | 90 | 100 | 100 | 80 |
| I-c-26 | 100 | 80 | 100 | 100 | 100 |
| I-c-27 | 100 | 80 | 100 | 100 | 90 |
| I-c-28 | 90 | 60 | 100 | | 50 |
| I-c-30 | 100 | 90 | 80 | 100 | 60 |
| I-c-31 | 90 | 80 | 60 | 0 | 60 |
| I-c-32 | 80 | 70 | 100 | 100 | 70 |
| I-c-33 | 90 | 90 | 90 | 100 | 60 |
| I-c-34 | 90 | 60 | 100 | 100 | 80 |
| I-c-35 | 80 | 70 | | 100 | 70 |
| I-c-39 | 100 | 70 | 80 | 60 | 70 |
| I-c-39 | 20 | 20 | 100 | 80 | 20 |
| I-c-40 | 80 | 60 | 0 | 80 | 40 |
| I-c-41 | 90 | 40 | 60 | 100 | 40 |
| I-c-43 | 80 | 40 | 80 | 80 | 0 |
| I-c-44 | 50 | 50 | 0 | 100 | 0 |
| I-c-45 | 60 | 80 | 80 | 80 | 80 |
| I-c-46 | 80 | 50 | 80 | 70 | 80 |
| I-c-50 | 30 | 0 | 0 | 100 | 0 |
| I-c-51 | 100 | 60 | 30 | 90 | 90 |
| I-c-52 | 60 | 70 | 50 | 100 | 70 |
| I-c-53 | 100 | 50 | 0 | 90 | 60 |
| I-c-54 | 90 | 40 | 0 | 90 | 0 |
| I-c-56 | 90 | 20 | 20 | 90 | 0 |
| I-c-61 | 70 | 60 | 90 | 50 | 90 |
| I-c-62 | 60 | 50 | 80 | 80 | 90 |
| I-c-63 | 80 | 70 | 50 | 100 | 50 |
| I-c-64 | 60 | 70 | 50 | 100 | 70 |
| I-c-65 | 100 | 60 | 80 | 100 | 90 |
| I-c-66 | 100 | 70 | 100 | 100 | 60 |
| I-c-71 | 70 | 70 | 100 | 100 | 90 |
| I-c-72 | 60 | 50 | 100 | 100 | 80 |
| I-c-73 | 70 | 40 | 50 | 100 | 60 |
| I-c-74 | 70 | 60 | 100 | 100 | 100 |
| I-c-75 | 70 | 60 | 100 | 100 | 60 |

-continued

| | | 80 g/ha | | | |
|---|---|---|---|---|---|
| Example | ALOMY | AVEFA | ECHCG | LOLMU | SETVI |
| I-c-76 | 80 | 20 | 100 | 90 | 90 |
| I-c-77 | 80 | 80 | 80 | 90 | 100 |
| I-c-78 | 100 | 90 | 100 | 100 | 80 |
| I-c-79 | 90 | 80 | 100 | 100 | 80 |
| I-c-80 | 100 | 60 | 100 | 100 | 60 |
| I-f-2 | 90 | 50 | 90 | 100 | 60 |
| I-f-4 | 0 | 50 | 90 | 100 | 50 |
| I-f-5 | 90 | 70 | 70 | 90 | 90 |
| I-f-6 | 60 | 90 | 70 | 90 | 70 |
| I-f-7 | 100 | 70 | 80 | 100 | 90 |
| I-f-8 | 30 | 40 | 0 | 100 | 70 |
| I-f-9 | 30 | 50 | 60 | 100 | 50 |
| I-f-11 | 40 | 50 | 0 | 100 | 20 |
| I-f-12 | 100 | 70 | 100 | 70 | 90 |
| I-f-13 | 100 | 0 | 100 | 100 | 90 |
| I-f-14 | 100 | 70 | 100 | 100 | 100 |
| I-f-15 | 100 | 60 | 100 | 100 | 90 |
| I-f-16 | 80 | 80 | 60 | 90 | 90 |
| I-f-17 | 80 | 60 | 90 | 100 | 90 |
| I-f-19 | 100 | 60 | 100 | 100 | 100 |
| I-f-20 | 100 | 70 | 100 | 100 | 100 |
| I-f-21 | 90 | 70 | 100 | 100 | 90 |
| I-f-22 | 80 | 70 | | 80 | 100 |

Post-Emergence Method

| | | 80 g/ha | | | |
|---|---|---|---|---|---|
| Example | ALOMY | AVEFA | ECHCG | LOLMU | SETVI |
| I-a-1 | 100 | 90 | 100 | 100 | |
| I-a-2 | 100 | 70 | 100 | 100 | 90 |
| I-a-3 | 90 | 90 | 100 | 100 | 100 |
| I-a-4 | 60 | 30 | 100 | 20 | 100 |
| I-a-5 | 60 | 50 | 100 | 90 | 100 |
| I-a-6 | 90 | 70 | 100 | 100 | 90 |
| I-a-7 | 90 | 60 | 100 | 100 | 90 |
| I-a-8 | 100 | 100 | 100 | 100 | 100 |
| I-a-9 | 60 | 60 | 100 | 90 | 90 |
| I-a-10 | 90 | 80 | 100 | 100 | 90 |
| I-a-11 | 90 | 90 | 100 | 100 | 100 |
| I-a-12 | 100 | 100 | 100 | 100 | 100 |
| I-a-13 | 90 | 90 | 100 | 100 | 90 |
| I-a-14 | 90 | 90 | 100 | 100 | 100 |
| I-a-15 | 90 | 90 | 100 | 100 | 90 |
| I-a-16 | 30 | 30 | 90 | 80 | 80 |
| I-a-17 | 30 | 40 | 90 | 90 | 80 |
| I-a-18 | 90 | 60 | 100 | 100 | 90 |
| I-a-19 | 80 | 0 | 90 | 100 | 50 |
| I-a-20 | 90 | 80 | 100 | 100 | 90 |
| I-a-25 | 100 | 100 | 100 | 100 | 100 |
| I-a-26 | 100 | 100 | 100 | 100 | 100 |
| I-a-27 | 100 | 100 | 100 | 100 | 90 |
| I-a-28 | 100 | 100 | 100 | 100 | 100 |
| I-a-29 | 100 | 100 | 100 | 100 | 80 |
| I-a-30 | 90 | 0 | 100 | 90 | 50 |
| I-a-31 | 100 | 80 | 100 | 100 | 100 |
| I-a-32 | 80 | 0 | 100 | 100 | 20 |
| I-a-33 | 100 | 0 | 100 | 100 | 90 |
| I-a-35 | 100 | 80 | 100 | 100 | 90 |
| I-a-36 | 50 | 0 | 90 | 90 | 90 |
| I-a-37 | 60 | 90 | 100 | 100 | 60 |
| I-a-38 | 100 | 90 | 80 | 100 | 90 |
| I-a-39 | 100 | 20 | 90 | 100 | 90 |
| I-a-40 | 80 | 60 | 90 | 90 | 80 |
| I-a-41 | 100 | 40 | 90 | 100 | 100 |
| I-a-43 | 20 | 0 | 90 | 40 | 40 |
| I-a-44 | 20 | 0 | 100 | 20 | 80 |
| I-a-45 | 0 | 0 | 80 | 0 | 80 |
| I-a-46 | 0 | 0 | 100 | 0 | 40 |
| I-a-47 | 20 | 80 | 100 | 100 | 100 |
| I-a-48 | 80 | 90 | 100 | 100 | 100 |

-continued 80 g/ha

| Example | ALOMY | AVEFA | ECHCG | LOLMU | SETVI |
|---|---|---|---|---|---|
| I-a-49 | 100 | 100 | 100 | 100 | 100 |
| I-a-50 | 100 | 100 | 100 | 100 | 100 |
| I-a-55 | 20 | 0 | 100 | 40 | 100 |
| I-a-56 | 0 | 0 | 100 | 0 | 100 |
| I-a-57 | 100 | 100 | 100 | 100 | 100 |
| I-a-58 | 100 |  | 100 | 100 | 100 |
| I-a-60 | 100 | 90 | 100 | 100 | 100 |
| I-a-61 | 90 | 90 | 100 | 100 | 90 |
| I-a-62 | 100 | 80 | 100 | 100 | 90 |
| I-a-68 | 90 | 0 | 100 | 100 | 40 |
| I-a-69 | 90 | 30 | 100 | 100 | 80 |
| I-a-70 | 90 | 0 | 100 | 100 | 60 |
| I-b-1 | 100 | 60 | 100 | 100 | 40 |
| I-b-2 | 100 | 60 | 90 | 100 | 80 |
| I-b-3 | 100 | 40 | 100 | 100 | 20 |
| I-b-4 | 100 | 90 | 100 | 100 | 60 |
| I-b-5 | 90 | 20 | 80 | 100 | 0 |
| I-b-6 | 90 | 100 | 100 | 100 | 90 |
| I-b-7 | 90 | 100 | 100 | 100 | 90 |
| I-b-8 | 90 | 70 | 80 | 100 | 60 |
| I-b-9 | 90 | 0 | 90 | 40 | 40 |
| I-b-10 | 90 | 20 | 90 | 70 | 70 |
| I-b-12 | 90 | 100 | 100 | 100 | 100 |
| I-b-13 | 100 | 100 | 100 | 100 | 100 |
| I-b-14 | 100 | 100 | 100 | 100 | 100 |
| I-b-15 | 100 | 90 | 100 | 100 | 100 |
| I-b-16 | 100 | 90 | 100 | 100 | 100 |
| I-b-17 | 90 | 90 | 100 | 100 | 90 |
| I-b-18 | 100 | 100 | 100 | 100 | 100 |
| I-b-19 | 20 | 30 | 100 | 40 | 80 |
| I-b-20 | 0 | 30 | 100 | 60 | 0 |
| I-b-21 | 90 | 90 | 100 | 100 | 90 |
| I-b-22 | 100 | 100 | 100 | 100 | 100 |
| I-b-23 | 100 | 100 | 100 | 100 | 100 |
| I-b-24 | 100 | 100 | 100 | 100 | 100 |
| I-b-25 | 100 | 100 | 100 | 100 | 100 |
| I-b-27 | 100 | 100 | 100 | 100 | 100 |
| I-b-28 | 100 | 100 | 100 | 100 | 100 |
| I-b-29 | 100 | 90 | 100 | 100 | 100 |
| I-b-30 | 20 | 100 | 100 | 100 | 90 |
| I-b-37 | 0 | 0 | 90 | 70 | 90 |
| I-b-38 | 40 | 0 | 90 | 70 | 90 |
| I-b-39 | 60 | 20 | 100 | 100 | 90 |
| I-b-40 | 40 | 20 | 90 | 100 | 80 |
| I-b-41 | 40 | 0 | 100 | 100 | 80 |
| I-b-42 | 100 | 80 | 100 | 100 | 100 |
| I-b-43 | 100 | 80 | 90 | 100 | 100 |
| I-b-44 | 80 | 80 | 80 | 100 | 60 |
| I-b-45 | 80 | 0 | 90 | 90 | 40 |
| I-b-46 | 90 | 40 | 90 | 100 | 80 |
| I-b-47 | 90 | 80 | 100 | 90 | 0 |
| I-b-48 | 90 | 40 | 90 | 90 | 80 |
| I-b-49 | 90 | 80 | 100 | 100 | 60 |
| I-b-50 | 100 | 0 | 90 | 100 | 80 |
| I-b-51 | 90 | 0 | 100 | 60 | 40 |
| I-b-52 | 0 | 0 | 100 | 0 | 90 |
| I-b-53 | 20 | 0 | 100 | 0 | 90 |
| I-b-54 | 20 | 0 | 100 | 0 | 100 |
| I-b-55 | 0 | 0 | 90 | 0 | 90 |
| I-b-56 | 20 | 0 | 100 | 0 | 100 |
| I-b-57 | 0 | 0 | 100 | 0 | 100 |
| I-b-58 | 0 | 0 | 80 | 60 | 20 |
| I-b-59 | 20 | 0 | 80 | 80 | 0 |
| I-b-60 | 0 | 0 | 100 | 0 | 80 |
| I-b-62 | 30 | 0 | 100 | 90 | 90 |
| I-b-63 | 100 | 100 | 100 | 100 | 100 |
| I-b-64 | 100 | 100 | 100 | 100 | 100 |
| I-b-65 | 90 | 90 | 100 | 100 | 100 |
| I-b-66 | 100 | 90 | 100 | 100 | 80 |
| I-b-67 | 100 | 70 | 100 | 100 | 90 |
| I-b-69 | 90 | 10 | 100 | 100 | 60 |
| I-b-70 | 70 | 0 | 100 | 100 | 40 |
| I-b-71 | 0 | 0 | 100 | 0 | 100 |
| I-b-72 | 0 | 0 | 100 | 0 | 90 |
| I-b-73 | 0 | 0 | 100 | 70 | 100 |
| I-b-74 | 80 | 80 | 100 | 100 | 80 |
| I-b-75 | 100 | 90 | 100 | 100 | 100 |
| I-b-76 | 90 | 90 | 100 | 100 | 100 |
| I-b-77 | 100 | 60 | 100 | 100 | 90 |
| I-b-78 | 100 | 70 | 100 | 100 | 70 |
| I-b-79 | 90 | 100 | 100 | 100 | 100 |
| I-c-1 | 100 | 60 | 60 | 100 | 40 |
| I-c-2 | 90 | 40 | 40 | 100 | 40 |
| I-c-3 | 90 | 80 | 90 | 100 | 80 |
| I-c-4 | 90 | 90 | 100 | 100 | 0 |
| I-c-5 | 20 | 30 | 100 | 90 | 90 |
| I-c-7 | 90 | 70 | 100 | 100 | 80 |
| I-c-8 | 90 | 60 | 100 | 100 | 90 |
| I-c-9 | 90 | 80 | 100 | 100 | 90 |
| I-c-10 | 90 | 100 | 100 | 100 | 90 |
| I-c-11 | 80 | 80 | 100 | 90 | 90 |
| I-c-12 | 90 | 90 | 100 | 100 | 100 |
| I-c-13 | 70 | 80 | 100 | 100 | 90 |
| I-c-14 | 90 | 70 | 100 | 100 | 100 |
| I-c-15 | 90 | 60 | 90 | 90 | 90 |
| I-c-16 | 0 | 30 | 90 | 80 | 30 |
| I-c-17 | 30 | 0 | 100 | 40 | 90 |
| I-c-18 | 60 | 0 | 80 | 90 | 0 |
| I-c-19 | 100 | 100 | 100 | 100 | 100 |
| I-c-20 | 90 | 90 | 100 | 100 | 100 |
| I-c-21 | 90 | 100 | 100 | 100 | 100 |
| I-c-22 | 100 | 100 | 100 | 100 | 100 |
| I-c-23 | 100 | 100 | 100 | 100 | 100 |
| I-c-24 | 100 | 80 | 100 | 100 | 100 |
| I-c-25 | 100 | 100 | 100 | 100 | 100 |
| I-c-26 | 100 | 100 | 100 | 100 | 100 |
| I-c-27 | 100 | 100 | 100 | 100 | 100 |
| I-c-28 | 100 | 100 | 100 | 100 | 100 |
| I-c-30 | 80 | 40 | 100 | 100 | 70 |
| I-c-31 | 70 | 90 | 100 | 100 | 90 |
| I-c-32 | 80 | 90 | 90 | 90 | 80 |
| I-c-33 | 80 | 90 | 100 | 90 | 80 |
| I-c-34 | 100 | 100 | 100 | 100 | 90 |
| I-c-35 | 100 | 100 | 100 | 100 | 100 |
| I-c-38 | 70 | 0 | 80 | 90 | 30 |
| I-c-39 | 90 | 0 | 100 | 100 | 70 |
| I-c-39 | 20 | 0 | 100 | 100 | 20 |
| I-c-40 | 100 | 0 | 100 | 100 | 100 |
| I-c-41 | 100 | 80 | 100 | 100 | 20 |
| I-c-42 | 0 | 0 | 100 | 0 | 100 |
| I-c-43 | 100 | 0 | 100 | 100 | 0 |
| I-c-44 | 40 | 80 | 100 | 100 | 90 |
| I-c-45 | 40 | 0 | 90 | 100 | 90 |
| I-c-46 | 40 | 0 | 80 | 90 | 90 |
| I-c-47 | 100 | 90 | 100 | 100 | 60 |
| I-c-48 | 20 | 20 | 90 | 100 | 80 |
| I-c-49 | 100 | 80 | 90 | 100 | 80 |
| I-c-50 | 60 | 0 | 80 | 100 | 80 |
| I-c-51 | 100 | 40 | 100 | 100 | 100 |
| I-c-52 | 100 | 80 | 90 | 100 | 100 |
| I-c-53 | 100 | 80 | 90 | 100 | 90 |
| I-c-54 | 90 | 0 | 90 | 80 | 40 |
| I-c-55 | 80 | 20 | 100 | 100 | 30 |
| I-c-56 | 90 | 20 | 80 | 80 | 40 |
| I-c-57 | 90 | 0 | 100 | 0 | 90 |
| I-c-58 | 0 | 0 | 100 | 0 | 100 |
| I-c-59 | 0 | 0 | 100 | 60 | 20 |
| I-c-60 | 20 | 0 | 100 | 80 | 0 |
| I-c-61 | 40 | 0 | 90 | 70 | 90 |
| I-c-62 | 0 | 50 | 100 | 90 | 100 |
| I-c-63 | 100 | 100 | 100 | 100 | 100 |
| I-c-64 | 80 | 80 | 100 | 100 | 100 |
| I-c-65 | 100 | 100 | 100 | 100 | 100 |
| I-c-66 | 100 | 100 | 100 | 100 | 100 |
| I-c-71 | 80 | 90 |  | 100 | 100 |
| I-c-72 | 100 | 70 | 100 | 100 | 100 |
| I-c-73 | 100 | 0 | 100 | 100 | 100 |
| I-c-74 | 60 | 70 | 100 | 100 | 100 |
| I-c-75 | 60 | 50 | 100 | 100 | 100 |
| I-c-76 | 10 | 0 | 100 | 90 | 100 |
| I-c-77 | 0 | 0 | 100 | 90 | 90 |
| I-c-78 | 100 | 0 | 90 | 100 | 80 |

-continued

80 g/ha

| Example | ALOMY | AVEFA | ECHCG | LOLMU | SETVI |
|---------|-------|-------|-------|-------|-------|
| I-c-79  | 100   | 70    | 100   | 100   | 90    |
| I-c-80  | 90    | 70    | 100   | 100   | 90    |
| I-f-1   | 80    | 40    | 90    | 90    | 80    |
| I-f-2   | 80    | 90    | 100   | 100   | 90    |
| I-f-3   | 90    | 0     | 90    | 90    | 80    |
| I-f-4   | 100   | 90    | 100   | 100   | 100   |
| I-f-5   | 100   | 100   | 100   | 100   | 100   |
| I-f-6   | 100   | 80    | 100   | 100   | 100   |
| I-f-7   | 100   | 100   | 100   | 100   | 100   |
| I-f-8   | 100   | 90    | 100   | 100   | 100   |
| I-f-9   | 80    | 90    | 80    | 100   | 100   |
| I-f-10  | 100   | 80    | 90    | 100   | 90    |
| I-f-11  | 60    | 40    | 90    | 100   | 80    |
| I-f-12  | 100   | 100   | 100   | 100   | 100   |
| I-f-13  | 100   | 100   | 100   | 100   | 100   |
| I-f-14  | 100   | 100   | 100   | 100   | 100   |
| I-f-15  | 80    | 90    | 100   | 100   | 100   |
| I-f-16  | 100   | 100   | 100   | 100   | 100   |
| I-f-17  | 100   | 100   | 100   | 100   | 100   |
| I-f-19  | 100   | 100   | 100   | 100   | 100   |
| I-f-20  | 100   | 100   | 100   | 100   | 100   |
| I-f-21  | 80    | 80    | 100   | 100   | 100   |
| I-f-22  | 30    | 40    | 100   | 80    | 100   |
| I-f-23  | 0     | 0     | 90    | 60    | 80    |

ALOMY: *Alopecurus myosuroide*
AVEFA: *Avena fatua*
ECHCG: *Echinochloa crus-galli*
LOLMU: *Lolium multiflorum*
SETVI: *Setaria viridis*

Example No. 3

Method crop compatibility small plot trial outdoors:

Customary sowing using a single seed seeder

Plot size: 11.25 m²/two repetitions

Treatment was carried out using a plot sprayer. The safener was applied together with the test substance as a tank mix using 300 l of water/ha (amounts of herbicide and safener are stated in g of ai/ha). Post-emergence application was carried out at the five-leaf stage of maize. Crop compatibility was assessed visually 14 and 27 days after the treatment (in percent compared to an untreated control), 100% damage=the plants have died, 0% damage=like control plants).

Outside trial with maize (Magixx Duo is cycloxidim-tolerant)

Post-Emergence Method

| Cultivar | Magixx Duo | Oldham | Magixx Duo | Oldham |
|----------|------------|--------|------------|--------|
|          | days after application/% damage | | | |
| g ai/ha  | 14 days    | 14 days | 27 days   | 27 days |
| Ex. I-a-8 SL 450 | 60 | 0% | 94% | 0% | 93% |
| Ex. I-a-8 + cyprosulphamide WP 50 | 60 + 60 | 0% | 23% | 0% | 13% |

Example No. 4

| Myzus test (MYZUPE spray treatment) | |
|---|---|
| Solvents: | 78.0 parts by weight of acetone |
|           | 1.5 parts by weight of dimethylformamide |
| Emulsifier: | 0.5 part by weight of alkylaryl polyglycol ether |

To produce a suitable preparation of active compound, one part by weight of active compound is mixed with the stated amounts of solvents and emulsifier, and the concentrate is diluted with emulsifier-containing water to the desired concentration.

Discs of Chinese cabbage leaves (*Brassica pekinensis*) which are infested by all stages of the green peach aphid (*Myzus persicae*) are sprayed with an active compound preparation of the desired concentration.

After six days, the effect in percent is determined. 100% means that all aphids have been killed; 0% means that none of the aphids have been killed.

In this test, for example, the following compounds of the Preparation Examples show an effect of ≧80% at an application rate of 500 g/ha:
Ex.: I-a-10, I-c-10, I-c-14

Example No. 5

| Heliothis virescens test - Treatment of transgenic plants | |
|---|---|
| Solvent: | 7 parts by weight of acetone |
| Emulsifier: | 1 part by weight of alkylaryl polyglycol ether |

To produce a suitable preparation of active compound, one part by weight of active compound is mixed with the stated amount of solvent and the stated amount of emulsifier, and the concentrate is diluted with water to the desired concentration.

Soya bean shoots (*Glycine max*) of the cultivar Roundup Ready (trademark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

Example No. 6

| Critical concentration test/Soil insects - Treatment of transgenic plants | |
|---|---|
| Test insect: | *Diabrotica balteata* - Larvae in the soil |
| Solvent: | 7 parts by weight of acetone |
| Emulsifier: | 1 part by weight of alkylaryl polyglycol ether |

To produce a suitable preparation of active compound, one part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l) matters. The soil is filled into 0.25 l pots, and these are allowed to stand at 20° C.

Immediately after the preparation, five pregerminated maize corns of the cultivar YIELD GUARD (trademark of Monsanto Comp., USA) are placed into each pot. After two days, the appropriate test insects are placed into the treated soil. After a further seven days, the efficacy of the active compound is determined by counting the maize plants that have emerged (1 plant=20% activity).

Example No. 7

Increase of penetration into the plant by ammonium or phosphonium salts and synergistic increase of penetration into the plant by ammonium/phosphonium salts in combination with penetrants.

In this test, the penetration of active compounds through enzymatically isolated cuticles of apple tree leaves was measured.

Use was made of leaves which, fully developed, were cut from apple trees of the cultivar Golden Delicious. The cuticles were isolated by initially filling leaf discs punched out and stained with dye on the underside by vacuum infiltration with a pectinase solution (0.2 to 2% strength) buffered to a pH between 3 and 4, then sodium azide was added and allowing the leaf discs treated in this manner to stand until the original leaf structure has dissolved and the non-cellular cuticles have detached.

Only the cuticles, free from hairs and stoma, of the upper sides of the leaves were then used. They were washed repeatedly alternating with water and a buffer solution of pH 7. The clean cuticles obtained were then mounted on Teflon plates and smoothed and dried with a gentle stream of air.

In the next step, the cuticle membranes obtained in this manner were placed into stainless steel diffusion cells (=transport chambers) for membrane transport studies. To this end, the cuticles were placed with a pincet into the centre of the edges, coated with silicone fat, of the diffusion cells and closed with a ring, which had also been treated with fat. The arrangement was chosen such that the morphological outside of the cuticles was facing outwards, i.e. exposed to air, whereas the original inside was facing the interior of the diffusion cells.

The diffusion cells were filled with a 30% strength ethylene glycol/water solution. To determine the penetration, in each case 10 μl of the spray liquor of the composition below were applied to the outside of the cuticles. The spray liquor was prepared using local tap water of medium hardness.

After the spray liquors had been applied, the water was allowed to evaporate and the chambers were inverted and placed into thermostatic taps in which temperature and atmospheric humidity over the cuticles could be adjusted using a gentle stream of air onto the cuticles with the spray coating (20° C., 60% rh). At regular intervals, an autosampler took aliquots and the active compound content was determined by HPLC.

The test results are shown in the table below. The stated numbers are average values of eight to ten measurements.

| | | | Penetration after 24 h/% | |
|---|---|---|---|---|
| Active compound | a.i. | a.i. + AS | a.i. + Edenor Me SU 500 EW | a.i. + Edenor ME SU 500 EW + AS |
| Example I-a-1 | 2.5 | 4 | 11.5 | 13 |
| Example I-a-14 | 0 | 3 | 5 | 16 |
| Example I-a-42 | 0 | 2 | 23 | 39 | a.i. (0.2 g/l)
AS = ammonium sulphate (0.7 g/l)
Edenor Me SU 500 EW (2 g/l)

The invention claimed is:
1. A compound of the formula (I)

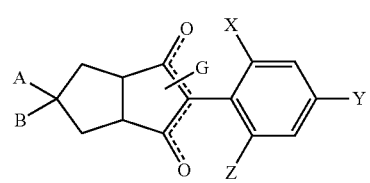

(I)

in which
X represents alkyl, cycloalkyl or alkoxy,
Y represents hydrogen, alkyl or alkoxy,
Z represents hydrogen, alkyl or cycloalkyl,
where
A and B together with the carbon atom to which they are attached represent a saturated or unsaturated unsubstituted or substituted cycle which optionally contains at least one heteroatom,
or
A and B together with the carbon atom to which they are attached represent a carbonyl group, a $C_1$-$C_4$-alkylene group or a =N—$OR^9$ group,
G represents hydrogen (a) or represents one of the groups

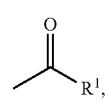

(b)

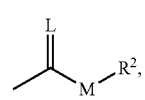

(c)

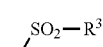

(d)

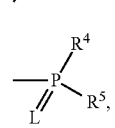

(e)

E or

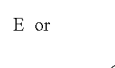

(f)

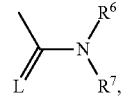

(g)

in which

E represents a metal ion equivalent or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulphur, $R^9$ represents hydrogen, represents in each case optionally substituted alkyl, cycloalkyl, $CH_2$-cycloalkyl, alkenyl, alkinyl, arylalkyl or hetarylalkyl.

2. The compound of the formula (I) according to claim 1 in which

X represents $C_1$-$C_4$-alkyl, $C_3$-$C_6$-cycloalkyl or $C_1$-$C_4$-alkoxy,

Y represents hydrogen, $C_1$-$C_4$-alkyl or $C_1$-$C_4$-alkoxy,

Z represents hydrogen, $C_1$-$C_4$-alkyl or $C_3$-$C_6$-cycloalkyl,

A, B and the carbon atom to which they are attached represent $C_3$-$C_8$-cycloalkyl or $C_5$-$C_8$-cycloalkenyl, in which optionally one or two ring members are replaced by oxygen and/or sulphur and which are optionally mono- to tetrasubstituted by $C_1$-$C_8$-alkyl, $C_1$-$C_8$-alkenyl, $C_1$-$C_4$-alkylene, $C_1$-$C_8$-halogenalkyl, $C_1$-$C_6$-alkoxy-$C_1$-$C_4$-alkyl, $C_1$-$C_6$-alkoxy, $C_1$-$C_6$-halogenalkoxy, hydroxyl, hydroxy-$C_1$-$C_4$-alkyl or benzyloxy, or a further fused-on $C_3$-$C_8$-cycloalkyl ring in which optionally one or two ring members are replaced by oxygen or sulphur, or which is optionally mono- or disubstituted by $C_1$-$C_8$-alkyl, or A, B and the carbon atom to which they are attached represent a carbonyl group, represent a $C_1$-$C_4$-alkylene group or represent a $=N-OR^9$ group, G represents hydrogen (a) or represents one of the groups (b)

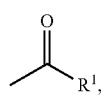

(c)

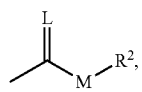

(d)

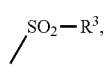

(e)

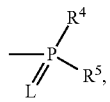

(f)

E or (g)

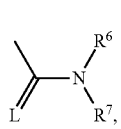

in which

E represents a metal ion equivalent or an ammonium ion,

L represents oxygen or sulphur, and

M represents oxygen or sulphur, $R^1$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$ alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-halogenalkyl-, $C_1$-$C_6$-halogenalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-halogenalkyl- or $C_1$-$C_6$-halogenalkoxy-substituted phenyl-$C_1$-$C_6$-alkyl, represents optionally halogen- or $C_1$-$C_6$-alkyl-substituted 5- or 6-membered heteroaryl, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered heteroaryloxy-$C_1$-$C_6$-alkyl, $R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-halogenalkyl- or $C_1$-$C_6$-halogenalkoxy-substituted phenyl or benzyl, $R^3$ represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-halogenalkyl-, $C_1$-$C_4$-halogenalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, Di-($C_1$-$C_8$-alkyl)amino, $C_1$-$C_8$-alkylthio, $C_2$-$C_8$-alkenylthio, $C_3$-$C_7$-Cycloalkylthio or represent in each case optionally halogen-, nitro-, cyano-, alkoxy-, $C_1$-$C_4$-halogenalkoxy-, $C_1$-$C_4$-alkylthio-, $C_1$-$C_4$-halogenalkylthio, $C_1$-$C_4$-alkyl- or $C_1$-$C_4$-halogenalkyl-substituted phenyl, phenoxy or phenylthio, $R^6$ and $R^7$ independently of one another represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-halogenalkyl-, $C_1$-$C_8$-alkyl- or $C_1$-$C_8$-alkoxy-substituted phenyl, optionally halogen-, $C_1$-$C_8$-alkyl-, $C_1$-$C_8$-halogenalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulphur, $R^9$ represents hydrogen, represents $C_1$-$C_6$-alkyl, $C_3$-$C_6$-cycloalkyl, $CH_2C_3$-$C_6$-cycloalkyl, $C_3$-$C_6$-alkenyl, $C_3$-$C_6$-alkynyl, each of which is optionally mono- to pentasubstituted by halogen, or represents phenyl-$C_1$-$C_2$-alkyl or heteroaryl-$C_1$-$C_2$-alkyl, each of which is optionally mono- to trisubstituted by alkyl, halogen, alkoxy, halogenalkyl or halogenalkoxy.

3. The compound of the formula (I) according to claim 1 in which

X represents methyl, ethyl, cyclopropyl, methoxy or ethoxy,

Y represents hydrogen, methyl or ethyl,

Z represents hydrogen, methyl, ethyl or cyclopropyl,

A, B and the carbon atom to which they are attached represent $C_3$-$C_8$-cycloalkyl or $C_5$-$C_8$-cycloalkenyl in which optionally one or two ring members are replaced by oxygen and/or sulphur and which is optionally mono- to tetrasubstituted by $C_1$-$C_4$-alkyl, $C_1$-$C_4$-alkenyl, a =$CH_2$ group, trifluoromethyl, $C_1$-$C_4$-alkoxy, $C_1$-$C_4$-alkoxy-$C_1$-$C_2$-alkyl or by one of the groups

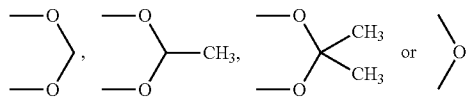

or

A, B and the carbon atom to which they are attached represent a carbonyl group, represent a $C_1$-$C_4$-alkylene group or represent a =N—$OR^9$ group, G represents hydrogen (a) or represents one of the groups (b)

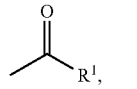

(c)

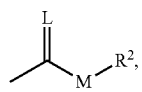

(d)

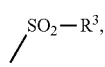

(e)

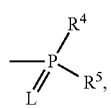

E or (f)

(g)

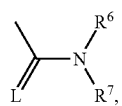

in which

E represents a metal ion equivalent or an ammonium ion,

L represents oxygen or sulphur and

M represents oxygen or sulphur, $R^1$ represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-alkyl or $C_1$-$C_2$-alkoxy or represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ represents $C_1$-$C_6$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ represents $C_1$-$C_6$-alkyl, $C_1$-$C_6$-alkoxy, $C_1$-$C_6$-alkylamino, Di-($C_1$-$C_6$-alkyl)amino, $C_1$-$C_6$-alkylthio, $C_3$-$C_4$-alkenylthio, $C_3$-$C_6$-cycloalkylthio, each of which is optionally mono- to trisubstituted by fluorine or chlorine, or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ represents $C_1$-$C_6$-alkylthio or $C_1$-$C_6$-alkoxy which is optionally monosubstituted by chlorine, $R^6$ represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ represents $C_1$-$C_6$-alkyl, $C_3$-$C_6$-alkenyl or $C_1$-$C_6$-alkoxy-$C_1$-$C_4$-alkyl, $R^6$ and $R^7$ together represent an optionally methyl- or ethyl-substituted $C_4$-$C_5$-alkylene radical in which optionally one methylene group is replaced by oxygen or sulphur, $R^9$ represents hydrogen, represents $C_1$-$C_4$-alkyl, $C_3$-$C_6$-cycloalkyl, $CH_2$—$C_3$-$C_6$-cycloalkyl, $C_3$-$C_4$-alkenyl, $C_3$-$C_4$-alkynyl, each of which is optionally mono- to trisubstituted by fluorine or chlorine, represents benzyl or pyridinylmethyl, each of which is optionally mono- or disubstituted by $C_1$-$C_2$-alkyl, $C_1$-$C_2$-alkoxy, fluorine, chlorine, bromine, trifluoromethyl or trifluoromethoxy.

4. The compound of the formula (I) according to claim 1 in which
X represents methyl, ethyl, cyclopropyl, methoxy or ethoxy,
Y represents hydrogen, methyl or ethyl,
Z represents hydrogen, methyl, ethyl or cyclopropyl,
A, B and the carbon atom to which they are attached represent $C_3$-$C_7$-cycloalkyl or $C_5$-$C_7$-cycloalkenyl in which optionally one or two ring members are replaced by oxygen and/or sulphur and which is optionally mono-, di-, tri- or tetrasubstituted by methyl, in each case monosubstituted by ethyl, a =$CH_2$ group, methoxy or ethoxy,
A, B and the carbon atom to which they are attached represent a carbonyl group, represent a =$CH_2$ group, represent a =$CH_2$—$CH_3$ group, represent a =$CH_2$—$C_2H_5$ group or represent a =N—$OR^9$ group,
G represents hydrogen (a) or represents one of the groups

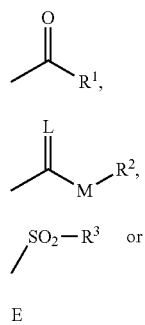

in which
E represents a metal ion equivalent,
L represents oxygen or sulphur and
M represents oxygen or sulphur,
represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or $C_3$-$C_6$-cyclopropyl which is optionally monosubstituted by fluorine, chlorine, methyl or methoxy or represents $C_1$-$C_4$-alkyl which is monosubstituted by chlorine,
represents phenyl which is optionally monosubstituted by fluorine, chlorine, bromine, cyano, nitro, methyl, methoxy, trifluoromethyl or trifluoromethoxy,
$R^2$ represents $C_1$-$C_8$-alkyl, $C_2$-$C_6$-alkenyl or $C_1$-$C_4$-alkoxy-$C_2$-$C_3$-alkyl, each of which is optionally mono- to trisubstituted by fluorine, represents phenyl or benzyl,
$R^3$ represents $C_1$-$C_6$-alkyl or represents phenyl which is optionally monosubstituted by chlorine or $C_1$-$C_4$-alkyl,
$R^9$ represents hydrogen, represents in each case optionally fluorine-substituted methyl, ethyl, propyl, n-butyl, isobutyl, s-butyl or tert-butyl, represents allyl, chloroallyl, propynyl, butynyl, chlorobenzyl, chloropyridylmethyl, $CH(CH_3)$—C≡CH, cyclopropyl, cyclobutyl, cyclopentyl, $CH_2$-cyclopropyl, $CH_2$-cyclobutyl or $CH_2$-cyclopentyl.

5. The compound of the formula (I) according to claim 1 in which
X represents methyl, ethyl or methoxy,
Y represents methyl or ethyl,
Z represents hydrogen, methyl or ethyl,
A, B and the carbon atom to which they are attached represent $C_5$-$C_7$-cycloalkyl or $C_7$-cycloalkenyl which optionally two ring members are replaced by oxygen and/or sulphur and which is optionally mono-, di- or tetrasubstituted by methyl, in each case monosubstituted by ethyl, a =$CH_2$ group, methoxy, ethoxy or benzyloxy,
A, B and the carbon atom to which they are attached represent a carbonyl group, represent a =$CH_2$ group or represent a =N—$OR^9$ group,
G represents hydrogen (a) or represents one of the groups

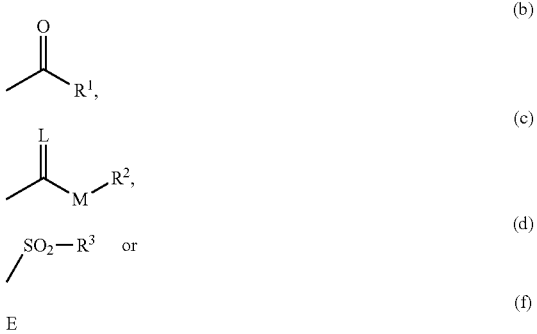

in which
E represents a metal ion equivalent,
L represents oxygen and
M represents oxygen,
$R^1$ represents $C_1$-$C_6$-alkyl or $C_1$-$C_2$-alkoxy-$C_1$-alkyl or $C_1$-$C_4$-alkyl which is monosubstituted by chlorine, represents phenyl which is optionally monosubstituted by chlorine, methyl or methoxy,
$R^2$ represents $C_1$-$C_8$-alkyl,
$R^3$ represents methyl, phenyl or p-methylphenyl,
$R^9$ represents hydrogen, methyl, isopropyl, isobutyl, tert-butyl, $CH_2CF_3$, $CH_2$—C≡CH, $CH(CH_3)$—C≡CH, cyclopropyl, cyclopentyl, $CH_2$-cyclopropyl, $CH_2$-cyclopentyl.

6. A composition for controlling pests and/or unwanted vegetation comprising at least one compound of the formula (I) according to claim 1.

7. A method for controlling animal pests and/or unwanted vegetation comprising administering a compound of the formula (I) according to claim 1 on the pests, unwanted vegetation and/or their habitat.

8. A process for preparing a composition for controlling pests and/or unwanted vegetation comprising mixing a compound of the formula (I) according to claim 1 with an extender and/or an surfactant.

9. A composition comprising an effective amount of an active compound combination comprising, as components,
(a') at least one compound of the formula (I) in which A, B, G, X, Y and Z have the meaning given in claim 1 and
(b') at least one crop plant compatibility-improving compound selected from the group consisting of
S1, a compound having the formula of

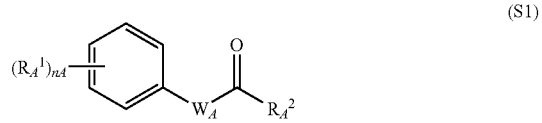

wherein
- $n_A$ is a natural number from 0 to 5;
- $R_A^1$ is halogen, $(C_1-C_4)$-alkyl, $(C_1-C_4)$-alkoxy, nitro or $(C_1-C_4)$-haloalkyl;
- $W_A$ is an unsubstituted or substituted divalent heterocyclic radical selected from the group consisting of partially unsaturated or aromatic five-membered heterocycles having 1 to 3 hetero ring atoms, wherein the hetero ring atom is selected from the group consisting of N and O, and wherein at least one nitrogen atom and at most one oxygen atom is present in the ring;

S2, a compound having the formula of

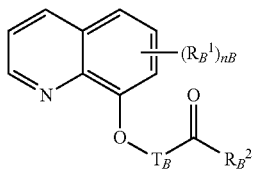

(S2)

wherein
- $R_B^1$ is halogen, $(C_1-C_4)$-alkyl, $(C_1-C_4)$-alkoxy, nitro or $(C_1-C_4)$-haloalkyl;
- $n_B$ is a natural number from 0 to 5, preferably from 0 to 3;
- $R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, which is attached via the nitrogen atom to the carbonyl group in (S2) and which is unsubstituted or substituted by a radical selected from the group consisting of $(C_1-C_4)$-alkyl, $(C_1-C_4)$-alkoxy and optionally substituted phenyl;
- $R_B^3$ is hydrogen, an unsubstituted or a substituted aliphatic hydrocarbon radical having a total of 1 to 18 carbon atoms;
- $R_B^4$ is hydrogen, $(C_1-C_6)$-alkyl, $(C_1-C_6)$-alkoxy or substituted or unsubstituted phenyl;
- $T_B$ is a $(C_1-$ or $C_2)$-alkanediyl chain which is unsubstituted or substituted by one or two $(C_1-C_4)$-alkyl radicals or by $[(C_1-C_3)$-alkoxy]carbonyl;

S3, a compound having the formula of

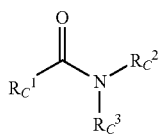

(S3)

wherein
- $R_C^1$ is $(C_1-C_4)$-alkyl, $(C_1-C_4)$-haloalkyl, $(C_2-C_4)$-alkenyl, $(C_2-C_4)$-haloalkenyl, or $(C_3-C_7)$-cycloalkyl;
- $R_C^2$, $R_C^3$ are identical or different and are hydrogen, $(C_1-C_4)$-alkyl, $(C_2-C_4)$-alkenyl, $(C_2-C_4)$-alkynyl $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring;

S4, a compound having the formula of

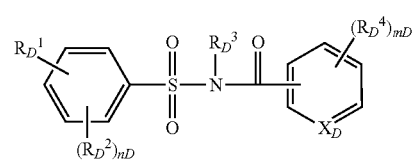

(S4)

wherein
- $X_D$ is CH or N;
- $R_D^1$ is $CO-NR_D^5R_D^6$ or $NHCO-R_D^7$;
- $R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;
- $R_D^3$ is hydrogen, $(C_1-C_4)$-alkyl, $(C_2-C_4)$-alkenyl or $(C_2-C_4)$-alkynyl;
- $R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;
- $R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains a $v_D$ heteroatom selected from the group consisting of nitrogen, oxygen and sulphur, wherein the $(C_2-C_6)$-alkenyl, $(C_2-C_6)$-alkynyl, or the phenyl or 3- to 6-membered heterocyclyl is substituted by a $v_D$ substituent selected from the group consisting of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl, and wherein the $(C_3-C_6)$-cycloalkyl, $(C_5-C_6)$-cycloalkenyl, or the phenyl or 3- to 6-membered heterocyclyl is substituted by a $v_D$ heteroatom selected from the group consisting of nitrogen, oxygen, sulphur, $(C_1-C_4)$-alkyl and $(C_1-C_4)$-haloalkyl;
- $R_D^6$ is hydrogen, $(C_1-C_6)$-alkyl, $(C_2-C_6)$-alkenyl or $(C_2-C_6)$-alkynyl, wherein the $(C_1-C_6)$-alkyl, $(C_2-C_6)$-alkenyl or $(C_2-C_6)$-alkynyl is substituted by a $v_D$ radical selected from the group consisting of halogen, hydroxy, $(C_1-C_4)$-alkyl, $(C_1-C_4)$-alkoxy and $(C_1-C_4)$-alkylthio, or
- $R_D^5$ and $R_D^6$ together with the nitrogen atom carrying them form a pyrrolidinyl or piperidinyl radical;
- $R_D^7$ is hydrogen, $(C_1-C_4)$-alkylamino, di-$(C_1-C_4)$-alkylamino, $(C_1-C_6)$-alkyl, or $(C_3-C_6)$-cycloalkyl; wherein the $(C_1-C_6)$-alkyl is substituted by a $v_D$ substituent selected from the group consisting of halogen, $(C_1-C_4)$-alkoxy, halo-$(C_1-C_6)$-alkoxy and $(C_1-C_4)$-alkylthio; and wherein the $(C_3-C_6)$-cycloalkyl is substituted by a $v_D$ substituent selected from the group consisting of halogen, $(C_1-C_4)$-alkoxy, halo-$(C_1-C_6)$-alkoxy, $(C_1-C_4)$-alkylthio, $(C_1-C_4)$-alkyl, and $(C_1-C_4)$-haloalkyl;
- $n_D$ is 0, 1 or 2;
- $m_D$ is 1 or 2;
- $v_D$ is 0, 1, 2 or 3;

S5, an active compound selected from the class of the hydroxyaromatics or aromatic-aliphatic carboxylic acid derivatives;

S6, an active compound selected from the class of the 1,2-dihydroquinoxalin-2-ones;

S7, a compound having the formula of

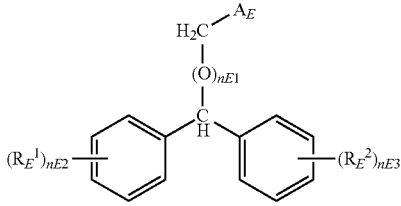

wherein
$R_E^1$, $R_E^2$ independently of one another are halogen, $(C_1$-$C_4)$-alkyl, $(C_1$-$C_4)$-alkoxy, $(C_1$-$C_4)$-haloalkyl, $(C_1$-$C_4)$-alkylamino, di-$(C_1$-$C_4)$-alkylamino, or nitro;
$A_E$ is $COOR_E^3$ or $COSR_E^4$
$R_E^3$, $R_E^4$ independently of one another are hydrogen, $(C_1$-$C_4)$-alkyl, $(C_7$-$C_6)$-alkenyl, $(C_2$-$C_4)$-alkynyl, cyanoalkyl, $(C_1$-$C_4)$-haloalkyl, phenyl, nitrophenyl, benzyl, halobenzyl, pyridinylalkyl or alkylammonium,
$n_E^1$ is 0 or 1;
$n_E^2$, $n_E^3$ independently of one another are 0, 1 or 2;

S8, a compound having the formula of

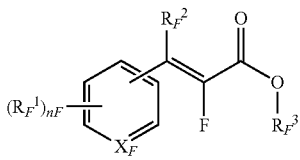

wherein
$X_F$ is CH or N,
$n_F$ is, if $X_F$=N, an integer from 0 to 4 and is, if $X_F$=CH, an integer from 0 to 5,
$R_F^1$ is halogen, $(C_1$-$C_4)$-alkyl, $(C_1$-$C_4)$-haloalkyl, $(C_1$-$C_4)$-alkoxy, $(C_1$-$C_4)$-haloalkoxy, nitro, $(C_1$-$C_4)$-alkylthio, $(C_1$-$C_4)$-alkylsulphonyl, or $(C_1$-$C_4)$-alkoxycarbonyl, or optionally substituted phenyl, or optionally substituted phenoxy,
$R_F^2$ is hydrogen or $(C_1$-$C_4)$-alkyl,
$R_F^3$ is hydrogen, $(C_1$-$C_8)$-alkyl, $(C_2$-$C_4)$-alkenyl, $(C_2$-$C_4)$-alkynyl or aryl, where each of the carbon-containing radicals mentioned above is unsubstituted or substituted by one or more, identical or different radicals selected from the group consisting of halogen and alkoxy and salts thereof;

S9, an active compound selected from the class of the 3-(5-tetrazolylcarbonyl)-2-quinolones;

S10, a compound having the formula of $(S10^a)$ or $(S10^b)$:

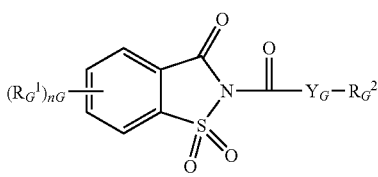

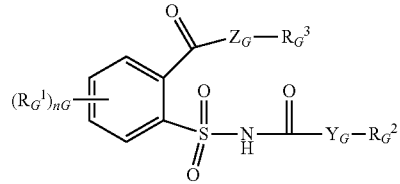

wherein
$R_G^1$ is halogen, $(C_1$-$C_4)$-alkyl, methoxy, nitro, cyano, $CF_3$, $OCF_3$
$Y_G$, $Z_G$ independently of one another are O or S,
$n_G$ is an integer from 0 to 4,
$R_G^2$ is $(C_1$-$C_{16})$-alkyl, $(C_2$-$C_6)$-alkenyl, $(C_3$-$C_6)$-cycloalkyl, aryl; benzyl, or halobenzyl,
$R_G^3$ is hydrogen or $(C_1$-$C_6)$-alkyl;

S11, an oxyimino compound;
S12, an isothiochromanone compound;
S13, at least one compound selected from the group consisting of naphthalic anhydride, fenclorim, flurazole, CL-304415 (CAS Reg. No.: 31541-57-8), MG-191 (CAS Reg. No.: 96420-72-3), MG-838 (CAS Reg. No.: 133993-74-5), disulfoton, dietholate and mephenate; and
S14, at least one compound selected from the group consisting of S-1-methyl-1-phenylethyl piperidine-1-carbothioate, 1-(1-methyl-1-phenylethyl)-3-p-tolylurea, 3-(2-chlorophenylmethyl)-1-(1-methyl-1-phenylethyl) urea, 3,3'-dimethyl-4-methoxybenzophenone and 1-bromo-4-(chloromethphonyl benzene.

10. A composition according to claim 9 in which the crop plant compatibility-improving compound is cloquintocet-mexyl.

11. A composition according to claim 9 in which the crop plant compatibility-improving compound is mefenpyr-diethyl.

12. A composition according to claim 9 in which the crop plant compatibility-improving compound is cyprosulfamide.

13. A method for controlling unwanted vegetation in plants or their surroundings, comprising administering a composition according to claim 9 to the plants or their surroundings.

14. A method for controlling unwanted vegetation in plants or their surroundings, comprising administering a compound of the formula (I) according to claim 1 and at least one crop plant compatibility-improving compound selected from the group consisting of S1, a compound having the formula of

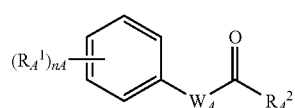

wherein
$n_A$ is a natural number from 0 to 5;
$R_A^1$ is halogen, $(C_1$-$C_4)$-alkyl, $(C_1$-$C_4)$-alkoxy, nitro or $(C_1$-$C_4)$-haloalkyl;
$W_A$ is an unsubstituted or substituted divalent heterocyclic radical selected from the group consisting of partially unsaturated or aromatic five-membered heterocycles having 1 to 3 hetero ring atoms, wherein the hetero ring atom is selected from the group consisting of N and O, and wherein at least one nitrogen atom and at most one oxygen atom is present in the ring;

S2, a compound having the formula of

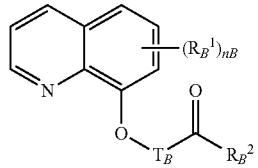

(S2)

wherein $R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, which is attached via the nitrogen atom to the carbonyl group in (S2) and which is unsubstituted or substituted by a radical selected from the group consisting of $(C_1-C_4)$-alkyl, $(C_1-C_4)$-alkoxy and optionally substituted phenyl;

$R_B^3$ is hydrogen, an unsubstituted or a substituted aliphatic hydrocarbon radical having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1-$ or $C_2)$-alkanediyl chain which is unsubstituted or substituted by one or two $(C_1-C_4)$-alkyl radicals or by $[(C_1-C_3)$-alkoxy]carbonyl;

S3, a compound having the formula of

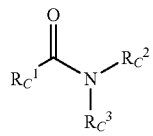

(S3)

wherein $R_C^1$ is $(C_1-C_4)$-alkyl, $(C_1-C_4)$-haloalkyl, $(C_2-C_4)$-alkenyl, $(C_2-C_4)$-haloalkenyl, or $(C_3-C_7)$-cycloalkyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring;

S4, a compound having the formula of

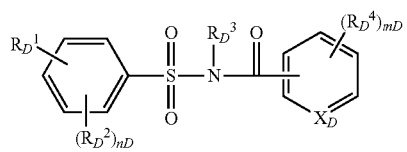

(S4)

wherein $X_D$ is CH or N;

$R_D^1$ is CO—$NR_D^5R_D^6$ or NHCO—$R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl which contains a $v_D$ heteroatom selected from the group consisting of nitrogen, oxygen and sulphur, wherein the $(C_2-C_6)$-alkenyl, $(C_2-C_6)$-alkynyl, or the phenyl or 3- to 6-membered heterocyclyl is substituted by a $v_D$ substituent selected from the group consisting of halogen, $(C_1-C_6)$-alkoxy, $(C_1-C_6)$-haloalkoxy, $(C_1-C_2)$-alkylsulphonyl, alkylsulphonyl, $(C_3-C_6)$-cycloalkyl, $(C_1-C_4)$-alkoxycarbonyl, alkylcarbonyl and phenyl, and wherein the $(C_3-C_6)$-cycloalkyl, $(C_5-C_6)$-cycloalkenyl, or the phenyl or 3- to 6-membered heterocyclyl is substituted by a $v_D$ heteroatom selected from the group consisting of nitrogen, oxygen, sulphur, $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, wherein the $(C_1-C_6)$-alkyl, $(C_2-C_6)$-alkenyl or $(C_2-C_6)$-alkynyl is substituted by a $v_D$ radical selected from the group consisting of halogen, hydroxy, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, or $(C_3-C_6)$-cycloalkyl; wherein the $(C_1-C_6)$-alkyl is substituted by a $v_D$ substituent selected from the group consisting of halogen, $(C_1-C_4)$-alkoxy, halo-$(C_1-C_6)$-alkoxy and $(C_1-C_4)$-alkylthio; and wherein the $(C_3-C_6)$-cycloalkyl is substituted by a $v_D$ substituent selected from the group consisting of halogen, $(C_1-C_4)$-alkoxy, halo-$(C_1-C_6)$-alkoxy, $(C_1-C_4)$-alkylthio, $(C_1-C_4)$-alkyl, and $(C_1-C_4)$-haloalkyl;

$n_D$ is 0, 1 or 2;

$m_D$ is 1 or 2;

$v_D$ is 0, 1, 2 or 3;

S5, an active compound selected from the class of the hydroxyaromatics or aromatic-aliphatic carboxylic acid derivatives;

S6, an active compound selected from the class of the 1,2-dihydroquinoxalin-2-ones;

S7, a compound having the formula of

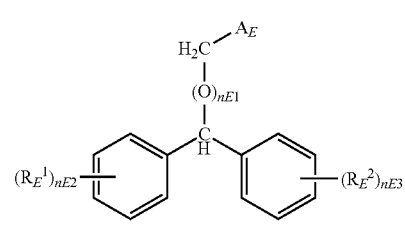

(S7)

wherein $R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, or nitro;

$A_E$ is $COOR_E^3$ or $COSR_E^4$ $R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ is 0 or 1;

$n_E^2$, $n_E^3$ independently of one another are 0, 1 or 2;

S8, a compound having the formula of

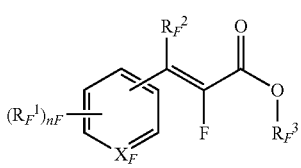

(S8)

wherein $X_F$ is CH or N, $n_F$ is, if $X_F$=N, an integer from 0 to 4 and is, if $X_F$=CH, an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, or $(C_1-C_4)$-alkoxycarbonyl, or optionally substituted phenyl, or optionally substituted phenoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, identical or different radicals selected from the group consisting of halogen and alkoxy and salts thereof;

S9, an active compound selected from the class of the 3-(5-tetrazolylcarbonyl)-2-quinolones;

S10, a compound having the formula of (S10$^a$) or (S10$^b$):

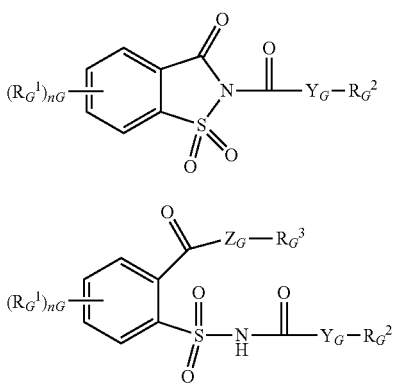

wherein $R_G^1$ is halogen, $(C_1-C_4)$-alkyl, methoxy, nitro, cyano, $CF_3$, $OCF_3$, $Y_G$, $Z_G$ independently of one another are 0 or 5, $n_G$ is an integer from 0 to 4, $R_G^2$ is $(C_1-C_{16})$-alkyl, $(C_2-C_6)$-alkenyl, $(C_3-C_6)$-cycloalkyl, aryl; benzyl, or halobenzyl, $R_G^3$ is hydrogen or $(C_1-C_6)$-alkyl;

S11, an oxyimino compound;

S12, an isothiochromanone compound;

S13, at least one compound selected from the group consisting of naphthalic anhydride, fenclorim, flurazole, CL-304415 (CAS Reg. No.: 31541-57-8), MG-191 (CAS Reg. No.: 96420-72-3), MG-838 (CAS Reg. No.: 133993-74-5), disulfoton, dietholate and mephenate; and S14, at least one compound selected from the group consisting of S-1-methyl-1-phenylethyl piperidine-1-carbothioate, 1-(1-methyl-1-phenylethyl)-3-p-tolylurea, 3-(2-chlorophenylmethyl)-1-(1-methyl-1-phenylethyl)urea, 3,3'-dimethyl-4-methoxybenzophenone and 1-bromo-4-(chloromethylsulphonyl)benzene, separately in close temporal succession to the plants or their surroundings.

15. A composition comprising
at least one compound of the formula (I) according to claim 1 or a composition according to claim 9 and
at least one salt of the formula (III')

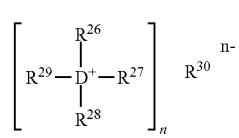

(III')

in which

D represents nitrogen or phosphorus, $R^{26}$, $R^{27}$, $R^{28}$ and $R^{29}$ independently of one another represent hydrogen or in each case optionally substituted $C_1-C_8$-alkyl or mono- or polyunsaturated, optionally substituted $C_1-C_8$-alkylene, the substituents being selectable from halogen, nitro and cyano, n represents 1, 2, 3 or 4, and $R^{30}$ represents an inorganic or organic anion.

16. A composition according to claim 15 further comprising at least one penetrant.

17. A method for increasing the activity of pesticides and/or herbicides comprising a ready-to-use composition that comprises an active compound of the formula (I) according to claim 1 or a composition according to claim 12, said method comprises preparing the ready-to-use composition further comprising a salt of the formula (III')

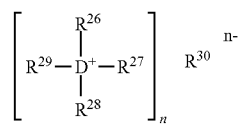

(III')

in which

D represents nitrogen or phosphorus, $R^{26}$, $R^{27}$, $R^{28}$ and $R^{29}$ independently of one another represent hydrogen or in each case optionally substituted $C_1-C_8$-alkyl or mono- or polyunsaturated, optionally substituted $C_1-C_8$-alkylene, the substituents being selectable from halogen, nitro and cyano, n represents 1, 2, 3 or 4, and $R^{30}$ represents an inorganic or organic anion.

18. The method according to claim 17, wherein said ready-to-use composition further comprises a penetrant.

* * * * *